US008685667B2

(12) United States Patent
Waldo et al.

(10) Patent No.: US 8,685,667 B2
(45) Date of Patent: Apr. 1, 2014

(54) NUCLEIC ACID ENCODING A SELF-ASSEMBLING SPLIT-FLUORESCENT PROTEIN SYSTEM

(75) Inventors: Geoffrey S. Waldo, Santa Fe, NM (US); Stephanie Cabantous, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 212 days.

(21) Appl. No.: 13/118,174

(22) Filed: May 27, 2011

(65) Prior Publication Data

US 2011/0256620 A1 Oct. 20, 2011

Related U.S. Application Data

(62) Division of application No. 10/973,696, filed on Oct. 25, 2004, now Pat. No. 7,955,821.

(60) Provisional application No. 60/514,363, filed on Oct. 24, 2003.

(51) Int. Cl.
*C12P 21/06* (2006.01)

(52) U.S. Cl.
USPC ......... 435/69.1; 435/252; 435/7.1; 435/320.1

(58) Field of Classification Search
None
See application file for complete search history.

(56) References Cited

U.S. PATENT DOCUMENTS

| | | | | |
|---|---|---|---|---|
| 6,379,670 | B1 | 4/2002 | Gaur et al. | |
| 6,414,119 | B1 | 7/2002 | Fisher | |
| 6,448,087 | B1 | 9/2002 | Waldo | |
| 6,780,599 | B2 | 8/2004 | Hamilton | |
| 7,271,241 | B2 | 9/2007 | Waldo | |
| 7,585,636 | B2 * | 9/2009 | Waldo et al. | 435/7.1 |
| 7,666,606 | B2 * | 2/2010 | Waldo et al. | 435/7.1 |
| 7,955,821 | B2 * | 6/2011 | Waldo et al. | 435/69.1 |
| 2002/0107362 | A1 | 8/2002 | Thastrup et al. | |
| 2002/0123113 | A1 | 9/2002 | Tsien et al. | |
| 2002/0177189 | A1 | 11/2002 | Bjorn et al. | |

FOREIGN PATENT DOCUMENTS

| | | |
|---|---|---|
| WO | WO 00/46233 | 8/2000 |
| WO | WO 01/13116 | 2/2001 |
| WO | WO 03/095610 | 11/2003 |

OTHER PUBLICATIONS

Ando et al., 2002, Proc. Natl. Acad. Sci. USA 99:12651-12656.
Bae et al., 2003, J. Mol. Biol. 328:1071-1081.
Baird et al., 1999, Proc. Natl. Acad. Sci. USA 96(20):11241-11246.
Baird et al., 2000, Proc. Natl. Acad. Sci. USA, 97:11984-11989.
Beddoe et al., 2003, Acta Cryst., D59:597-599.
Bulina et al., 2002, BMC Biochem., 3:7-8.
Campbell et al., 2002, Proc. Natl. Acad. Sci. USA, 99:7877-7882.
Cotlet et al., 2001, Proc. Natl. Acad. Sci. USA, 98:14398-14403.
Cove et al, 2001, Coral Reefs, 19:197-204.
Crameri et al., 1996, Nat. Biotechnol., 14(3):315-319.
Gurskaya et al., 2001, FEBS Letters, 507:16-20.
Hongbin et al., 2003, Biochem. Biophys. Res. Commun., 301:879-885.
Hu et al., 2002, Mol. Cell, 9:789-798.
Lukyanov et al., 2000, J. Biol. Chem., 275:25879-25882.
Lutz and Bujard, 1997, Nucleic Acids Res., 25(6):1203-1210.
Matz et al., 1999, Nat. Biotechnol., 17:969-973.
Nagai et al., 2001, Proc. Natl. Acad. Sci., USA 98:3197-3202.
Ormo et al., 1996, Science, 273(5280):1392-1395.
Ozawa et al., 2001, Anal. Chem., 72:5151-5157.
Ozawa et al., 2002, Anal. Chem., 73:5866-5874.
Pelletier et al., 1998, Proc. Natl. Acad. Sci. USA, 95(21):12141-12146.
Petersen et al., 2003, J. Biol. Chem., 278:44626-44631.
Rossi et al., 2000, Methods Enzymol., 328:231-251.
Smith and Matthews, 2001, Protein Sci., 10(1):116-128.
Terskikh et al., 2000, Science, 290:1685-1688.
Terwilliger, 2004, Nat. Struct. Mol. Biol., 11(4):296-297.
Tsien, 1998, Annu. Rev. Biochem., 67:509-544.
Umezawa, 2003, Chem Rec., 3:22-28.
Verkhusha et al., 2003, Protein Structures: Kaleidoscope of Structural Properties and Functions, 2003:405-439.
Waldo, 2003, Curr. Opin. Chem. Biol., 7(1): 33-38.
Waldo, 2003, Methods Mol. Biol., 230:343-359.
Waldo et al., 1999, Nature Biotechnology, 17(7):691-695.
Wehrman et al., 2002, Proc. Natl. Acad. Sci. USA, 99(6):3469-3474.
Wiedenmann et al., 2000, Proc. Natl. Acad. Sci. USA, 97:14091-14096.
Wiedenmann et al., 2002, Proc. Natl. Acad. Sci. USA, 99:11646-11651.
Wiehler et al., 2001, FEBS Letters, 487:384-389.
Wigley et al., 2001, Nat. Biotechnol., 19(2):131-136.
Yang et al., 1996 Nat. Biotechnol., 10:1246-1251.
Yarbrough et al., 2001, Proc. Natl. Acad. Sci. USA, 98:462-467.
Zhang et al., 2002, Nature Rev., 3:906-918.
Zhang et al., 2004, Cell, 119:137-144.
Zimmer et al., 2002, Chem. Rev., 102:759-781.

* cited by examiner

*Primary Examiner* — Hope Robinson
(74) *Attorney, Agent, or Firm* — Klarquist Sparkman, LLP

(57) ABSTRACT

The invention provides a protein labeling and detection system based on self-complementing fragments of fluorescent and chromophoric proteins. The system of the invention is exemplified with various combinations of self-complementing fragments derived from *Aequorea victoria* Green Fluorescent Protein (GFP), which are used to detect and quantify protein solubility in multiple assay formats, both in vitro and in vivo.

19 Claims, 25 Drawing Sheets
(9 of 25 Drawing Sheet(s) Filed in Color)

FIG. 1 B

TCGAGTCCCTATCAGTGATAGAGATTGACATCCCTATCAGTGATAGAGATACTGAGCACATCAGCAGGACGCACTGACCG
AGTTCATTAAAGAGGAGAAAGATACCCATGGCAGCAGCCATCATCATCATCATCACAGCAGCGGCCTGGTGCCGCGCGG
CAGCCATATGGGTGGCGGTTCTGGATCCGGAGGCACTAGTGGTGGCGGCTCAGGTACCTAACTCGAGCACCACCACCACC
ACCACTGAGATCCGGCTGCTAACAAAGCCCGAAAGGAAGCTGAGTTGGCTGCTGCCACCGCTGAGCAATAACTAGCATAA
CCTCTAGAGGCATCAAATAAAACGAAAGGCTCAGTCGAAAGACTGGGCCTTTCGTTTTATCTGTTGTTTGTCGGTGAACG
CTCTCCTGAGTAGGACAAATCCGCCGCCCTAGACCTAGGCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGCTCACGCTGTAGGTATCTC
AGTTCGGTGTAGGTCGTTCGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTTTTCTACGGGGT
CTGACGCTCAGTGGAACGAAAACTCACGTTAAGGGATTTTGGTCATGACTAGCGCTTGGATTCTCACCAATAAAAAACGC
CCGGCGGCAACCGAGCGTTCTGAACAAATCCAGATGGAGTTCTGAGGTCATTACTGGATCTATCAACAGGAGTCCAAGC
[illegible]
CTCTCGAACCCCAGAGTCCCGCA[illegible]
[illegible]GACGTCTAAGAAACCATTATTATCATGACATTAACCTATAAAAATAGGCGTATCACGAGGCCCTTTCGTCTT
CACC

Bold v1 cloning cassette for expressing genes under tet promoter, flanked by NcoI CCATGG, and KpnI GGTACC.

Features highlighted from top of sequence to bottom:

- TO transcription terminator for the SpecR-tetR cistron
- tetR repressor gene
- RBS controlling tetR translation
- spectinomycin (specR) gene
- Kanamycin Promoter element from PROLAR

| pmol Trace | Offset | Scale Factor |
|---|---|---|
| 50 | 0 | 1 |
| 25 | -222 | 1.962 |
| 12.5 | -120 | 4.015 |
| 6.25 | 8.76 | 8.147 |
| 3.13 | -40.4 | 15.64 |
| 1.56 | 52.5 | 36.52 |

FIG. 18 A

```
YTMDLPDNHYLSTQTILLKDLNGTGVGSGGGSHMGGGSGSGGGSGGGSTSEKRDHMVLLEYVTAAGITGAS*LEHHHHHH*DPAANK
YTMDLPDNHYLSTQTILLKDLNGTGVGSGGGSHMGGGSGSGGESGGGSTGEKRDHMVLLEYVTAAGITGAS*LEHHHHHH*DPAANK
YTMDLPDNHYLSTQTILLKDLNGTGVGSGGGSHMGGGSGSGGGSGGGSTSEKRDHMVLLEYVTAAGITGAS*LEHHHHHH*DPAANK
YTMDLPDNHYLSTQTILLKDLNGTDVGSGGGSHMGGGSGSDGGSGGGSTGEKRDHMVLLEYVTAAGITGAS*LEHHHHHH*DPAANK
YTMDLPDNHYLSTQTILLKDLNGTGVGSGGGSHMGGGSGSGGGSGGGSTSEKRDHMVLLEYVTAAGITGAS*LEHHHHHH*DPAANK
YTMDLPDNHYLSTQTILLKDLNGTGGGSGDGCHMDGGSGSGGGSGGGSTGEKRDHMVLLEYVTAAGITGAS*LEHHHHHH*DPAANK
YTMGLP[illegible]PNGTGGGSGGGSHMGGGSGSGGGSGGGSTSEK[illegible]ITGAS*LENS
```

FIG. 18 B

```
            195              200              205              210
G  P  V  L  L  P  [illegible]                                     P  N  E  K  *  G
GGCCCTGTCCTTTTACCANNNAACCATTACCTGTCGACA    03081301
  CCTGTCCTTTTACCAGACNNNCATTACCTGTCGACACAA    03081303
    GTCCTTTTACCAGACAACNNNTACCTGTCGACACAAACT    03081305
      CTTTTACCAGACAACCATNNNCTGTCGACACAAACTGTC    03081307
        TTACCAGACAACCATTACNNNTCGACACAAACTGTCCTT    03081309
          CCAGACAACCATTACCTGNNNACACAAACTGTCCTTTCG    03081311
            GACAACCATTACCTGTCGNNNCAAACTGTCCTTTCGAAA    03081313
              AACCATTACCTGTCGACANNNACTGTCCTTTCGAAAGAT    03081315
                CATTACCTGTCGACACAANNNGTCCTTTCGAAAGATCCC    03081317
                  TACCTGTCGACACAAACTNNNCTTTCGAAAGATCCCAAC    03081319
                    CTGTCGACACAAACTGTCNNNTCGAAAGATCCCAACGAA    03081321
                      TCGACACAAACTGTCCTTNNNAAAGATCCCAACGAAAAG    03081323
                        ACACAAACTGTCCTTTCGNNNGATCCCAACGAAAAGTAA    03081325
                          CAAACTGTCCTTTCGAAANNNCCCAACGAAAAGTAAGGT    03081327
GGCCCTGTCCTTTTACCAGACAACCATTACCTGTCGACACAAACTGTCCTTTCGAAAGATCCCAACGAAAAGTAAGGTACC
CCGGGACAGGAAAATGGTCTGTTGGTAATGGACAGCTGTGTTTGACAGGAAAGCTTTCTAGGGTTGCTTTTCATTCCATGG
                                                  GAAAGCTTTCTAGGGTTGCTTTTCATTCCATGG    03081336 (clone K * Kpn-1)
```

FIG. 19

```
YTMGLP            PNGTGGGSGGGSHMGGGSGSGGGSGGGSTSEK              ITGAS*LENS
YTMDLPDNHYLSTQTILLKDLNGTGVGSGGGSHMGGGSGSGGGSGGGSTSEKRDHMVLLEXVTIAAGITDAS*LEHHHHHH*DPAANK
  XDLXD XYLSTQTIL KDLNGT VGSGGGSHMKLQVALD       A10 (Most soluble with hexulose lyase)
 PXDLXD XYLSTQTIL KDLNGTGVGSGGGSHMKLQVALD       C10
 PXDLXD XYLSTQTIL KDLNGTGVGSGGGSHMKLQVALDL      E10
IPMDLPD HYLSTQTIL KDLNGTGVGSGGGSHMKLQVALDLVD    G10
   DLPD HYLSTQTIL KDLNGTGVGSDGGSHMKLQVALDLVD    A11
IPMDLPD HYLSTQTIL KDLNGT VGSGGGSHMKLQVALDLV     C11
IPMDLPD HYLSTQTIL KDLNGTGVGSGGGSHMKLQVALDLVDL   E11
IPMDLPD HYLSTQTIL KDLNGTGVGSGGGSHMKLQVALDLVD    G11
```

S: Soluble extract
U: Unbound fraction
E: Eluted fraction after 150mM imidazole elution

#2: sulfite reductase
#4: translation initiation factor
#5: ribosomal protein S9p
#13: tyrosine tRNA synthase
#17: phosphate cyclase

SEQUENCE LISTING

```
<160> NUMBER OF SEQ ID NOS: 81

<210> SEQ ID NO 1
<211> LENGTH: 646
<212> TYPE: DNA
<213> ORGANISM: Artificial
<220> FEATURE:
<223> OTHER INFORMATION: GFP variant; sequence encoding fragment
      corresponding to -strands 1-10

<400> SEQUENCE: 1

atgagcaaag gagaagaact tttcactgga gttgtcccaa ttcttgttga attagatggt      60

gatgttaatg ggcacaaatt ttctgtcaga ggagagggtg aaggtgatgc tacaaacgga     120

aaactcaccc ttaaatttat ttgcactact ggaaaactac ctgttccatg gccaacactt     180

gtcactactc tgacctatgg tgttcaatgc ttttcccgtt atccggatca catgaaacgg     240

catgactttt tcaagagtgc catgcccgaa ggttatgtac aggaacgcac tatatctttc     300

aaagatgacg ggacctacaa gacgcgtgct gaagtcaagt ttgaaggtga tacccttgtt     360

aatcgtatcg agttaaaagg tattgatttt aaagaagatg gaaacattct cggacacaaa     420

ctcgagtaca actttaactc acacaatgta tacatcacgg cagacaaaca aaagaatgga     480

atcaaagcta acttcaaaat tcgccacaac gttgaagatg gttccgttca actagcagac     540

cattatcaac aaaatactcc aattggcgat ggccctgtcc ttttaccaga caaccattac     600

ctgtcgacac aatctgtcct ttcgaaagat cccaacgaaa agctaa                    646


<210> SEQ ID NO 2
<211> LENGTH: 214
<212> TYPE: PRT
<213> ORGANISM: Artificial
<220> FEATURE:
<223> OTHER INFORMATION: GFP variant; fragment corresponding to -strands
      1-10

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110
```

-continued

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys
    210

<210> SEQ ID NO 3
<211> LENGTH: 651
<212> TYPE: DNA
<213> ORGANISM: Artificial
<220> FEATURE:
<223> OTHER INFORMATION: GFP variant; sequence encoding fragment corresponding to -strands 1-10 OPT

<400> SEQUENCE: 3
atgagcaaag gagaagaact tttcactgga gttgtcccaa ttcttgttga attagatggt 60
gatgttaatg ggcacaaatt ttctgtcaga ggagagggtg aaggtgatgc tacaatcgga 120
aaactcaccc ttaaatttat ttgcactact ggaaaactac ctgttccatg gccaacactt 180
gtcactactc tgacctatgg tgttcaatgc ttttcccgtt atccggatca catgaaaagg 240
catgactttt tcaagagtgc catgcccgaa ggttatgtac aggaacgcac tatatctttc 300
aaagatgacg ggaaatacaa gacgcgtgct gtagtcaagt ttgaaggtga tacccttgtt 360
aatcgtatcg agttaaaggg tactgatttt aaagaagatg gaaacattct cggacacaaa 420
ctcgagtaca actttaactc acacaatgta tacatcacgg cagacaaaca aaagaatgga 480
atcaaagcta acttcacagt tcgccacaac gttgaagatg gttccgttca actagcagac 540
cattatcaac aaaatactcc aattggcgat ggccctgtcc ttttaccaga caaccattac 600
ctgtcgacac aaactgtcct ttcgaaagat cccaacgaaa agggtaccta a 651

<210> SEQ ID NO 4
<211> LENGTH: 216
<212> TYPE: PRT
<213> ORGANISM: Artificial
<220> FEATURE:
<223> OTHER INFORMATION: GFP variant; fragment corresponding to -strands 1-10 OPT

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

```
His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215


<210> SEQ ID NO 5
<211> LENGTH: 651
<212> TYPE: DNA
<213> ORGANISM: Artificial
<220> FEATURE:
<223> OTHER INFORMATION: GFP variant; sequence encoding fragment
      corresponding to -strands 1-10 A4

<400> SEQUENCE: 5

atgagcaaag gagaagaact tttcactgga gttgtcccaa ttcttgttga attagatgga     60

gatgttaatg ggcacaaatt ttctgtcaga ggagagggtg aaggtgatgc tacaaacgga    120

aaactcaccc ttaaattcat ttgcactact ggaaaactac ctgttccatg gccaacgctt    180

gtcactactc tgacctatgg tgttcaatgc ttttcccgtt atccggatca catgaaacag    240

catgactttt tcaagagtgc catgcccgaa ggttatgtac aggaacgcac tatatatttc    300

aaagatgacg ggaactacaa gacgcgtgct gtagtcaagt ttgaaggtga tacccttgtt    360

aatcgtatcg agttaaaggg tactgatttt aaagaagatg gaaacattct cggacacaaa    420

ctcgagtaca actttaactc acacaatgta tatatcacgg cagacaaaca aaagaatgga    480

atcaaagcta acttcacaat tcgccacaac gttgtagatg gttccgttca actagcagac    540

cattatcaac aaaatactcc aattggcgat ggccctgtcc ttttaccaga caaccattac    600

ttgtcgacac aaactgtcct ttcgaaagat cccaacgaaa agggtaccta a             651


<210> SEQ ID NO 6
<211> LENGTH: 216
<212> TYPE: PRT
<213> ORGANISM: Artificial
<220> FEATURE:
<223> OTHER INFORMATION: GFP variant; fragment corresponding to -strands
      1-10 A4

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45
```

```
Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Tyr Phe Lys Asp Asp Gly Asn Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Val Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr
    210                 215


<210> SEQ ID NO 7
<211> LENGTH: 84
<212> TYPE: DNA
<213> ORGANISM: Artificial
<220> FEATURE:
<223> OTHER INFORMATION: GFP variant; sequence encoding fragment
      corresponding to -strand 11, amino acids 214-238

<400> SEQUENCE: 7

aagcgtgacc acatggtcct tcttgagttt gtaactgctg ctgggattac acatggcatg     60

gatgagctct acaaaggtac ctaa                                            84


<210> SEQ ID NO 8
<211> LENGTH: 27
<212> TYPE: PRT
<213> ORGANISM: Artificial
<220> FEATURE:
<223> OTHER INFORMATION: GFP variant; fragment corresponding to -strand
      11, amino acids 214-238

<400> SEQUENCE: 8

Lys Arg Asp His Met Val Leu Leu Glu Phe Val Thr Ala Ala Gly Ile
1               5                   10                  15

Thr His Gly Met Asp Glu Leu Tyr Lys Gly Thr
            20                  25


<210> SEQ ID NO 9
<211> LENGTH: 60
<212> TYPE: DNA
<213> ORGANISM: Artificial
<220> FEATURE:
<223> OTHER INFORMATION: GFP variant; sequence encoding fragment
      corresponding to -strand 11, amino acids 214-230

<400> SEQUENCE: 9

aagcgtgacc acatggtcct tcttgagttt gtaactgctg ctgggattac aggtacctaa     60
```

<210> SEQ ID NO 10
<211> LENGTH: 19
<212> TYPE: PRT
<213> ORGANISM: Artificial
<220> FEATURE:
<223> OTHER INFORMATION: GFP variant; fragment corresponding to -strand 11, amino acids 214-230

<400> SEQUENCE: 10

Lys Arg Asp His Met Val Leu Leu Glu Phe Val Thr Ala Ala Gly Ile
1 5 10 15

Thr Gly Thr

<210> SEQ ID NO 11
<211> LENGTH: 60
<212> TYPE: DNA
<213> ORGANISM: Artificial
<220> FEATURE:
<223> OTHER INFORMATION: GFP variant; sequence encoding fragment corresponding to -strand 11, M1 mutant

<400> SEQUENCE: 11
aagcgtgacc acatggtcct tcatgagttt gtaactgctg ctgggattac aggtacctaa 60

<210> SEQ ID NO 12
<211> LENGTH: 19
<212> TYPE: PRT
<213> ORGANISM: Artificial
<220> FEATURE:
<223> OTHER INFORMATION: GFP variant; fragment corresponding to -strand 11, M1 mutant

<400> SEQUENCE: 12

Lys Arg Asp His Met Val Leu His Glu Phe Val Thr Ala Ala Gly Ile
1 5 10 15

Thr Gly Thr

<210> SEQ ID NO 13
<211> LENGTH: 54
<212> TYPE: DNA
<213> ORGANISM: Artificial
<220> FEATURE:
<223> OTHER INFORMATION: GFP variant; sequence encoding fragment corresponding to -strand 11, M2 mutant

<400> SEQUENCE: 13
aagcgtgacc acatggtcct tcatgagtct gtaaatgctg ctgggggtac ctaa 54

<210> SEQ ID NO 14
<211> LENGTH: 17
<212> TYPE: PRT
<213> ORGANISM: Artificial
<220> FEATURE:
<223> OTHER INFORMATION: GFP variant; fragment corresponding to -strand 11, M2 mutant

<400> SEQUENCE: 14

Lys Arg Asp His Met Val Leu His Glu Ser Val Asn Ala Ala Gly Gly
1 5 10 15

Thr

<210> SEQ ID NO 15
<211> LENGTH: 51
<212> TYPE: DNA
<213> ORGANISM: Artificial
<220> FEATURE:
<223> OTHER INFORMATION: GFP variant; sequence encoding fragment corresponding to -strand 11, M3 mutant

<400> SEQUENCE: 15
cgtgaccaca tggtccttca tgagtctgta aatgctgctg ggattacata a 51

<210> SEQ ID NO 16
<211> LENGTH: 16
<212> TYPE: PRT
<213> ORGANISM: Artificial
<220> FEATURE:
<223> OTHER INFORMATION: GFP variant; fragment corresponding to -strand 11, M3 mutant

<400> SEQUENCE: 16

Arg Asp His Met Val Leu His Glu Tyr Val Asn Ala Ala Gly Ile Thr
1 5 10 15

<210> SEQ ID NO 17
<211> LENGTH: 54
<212> TYPE: DNA
<213> ORGANISM: Artificial
<220> FEATURE:
<223> OTHER INFORMATION: GFP variant; sequence encoding fragment corresponding to -strand 11, H7 HIS-tag

<400> SEQUENCE: 17
aagcatgacc acatgcacct tcatgagcat gtacatgctc atgggggtac ctaa 54

<210> SEQ ID NO 18
<211> LENGTH: 17
<212> TYPE: PRT
<213> ORGANISM: Artificial
<220> FEATURE:
<223> OTHER INFORMATION: GFP variant; fragment corresponding to -strand 11, H7 HIS-tag

<400> SEQUENCE: 18

Lys His Asp His Met His Leu His Glu His Val His Ala His Gly Gly
1 5 10 15

Thr

<210> SEQ ID NO 19
<211> LENGTH: 51
<212> TYPE: PRT
<213> ORGANISM: Artificial
<220> FEATURE:
<223> OTHER INFORMATION: GFP variant; sequence encoding fragment corresponding to -strand 11, H9 HIS-tag

<400> SEQUENCE: 19

Cys Ala Thr Gly Ala Cys Cys Ala Cys Ala Thr Gly Cys Ala Cys Cys
1 5 10 15

Thr Thr Cys Ala Thr Gly Ala Gly Cys Ala Thr Gly Thr Ala Cys Ala
20 25 30

Thr Gly Cys Thr Cys Ala Thr Cys Ala Cys Cys Ala Thr Ala Cys Cys
35 40 45

Thr Ala Ala
50

<210> SEQ ID NO 20
<211> LENGTH: 16
<212> TYPE: PRT
<213> ORGANISM: Artificial
<220> FEATURE:
<223> OTHER INFORMATION: GFP variant; fragment corresponding to -strand 11, H9 HIS-tag

<400> SEQUENCE: 20

His Asp His Met His Leu His Glu His Val His Ala His His His Thr
1 5 10 15

<210> SEQ ID NO 21
<211> LENGTH: 1775
<212> TYPE: DNA
<213> ORGANISM: Artificial
<220> FEATURE:
<223> OTHER INFORMATION: Unique genetic elements of pTET-SpecR expression vector of SEQ ID NO: 22; elements from T0 to AatII:tet repressor protein tetR and Spectinomycin gene under control of kanamycin promoter and RBS controlling expression of tet repressor

<400> SEQUENCE: 21
ttaagaccca ctttcacatt taagttgttt ttctaatccg tatatgatca attcaaggcc 60
gaataagaag gctggctctg caccttggtg atcaaataat tcgatagctt gtcgtaataa 120
tggcggcata ctatcagtag taggtgtttc cctttcttct ttagcgactt gatgctcttg 180
atcttccaat acgcaaccta aagtaaaatg ccccacagcg ctgagtgcat ataatgcatt 240
ctctagtgaa aaaccttgtt ggcataaaaa ggctaattga ttttcgagag tttcatactg 300
tttttctgta ggccgtgtac ctaaatgtac ttttgctcca tcgcgatgac ttagtaaagc 360
acatctaaaa cttttagcgt tattacgtaa aaaatcttgc cagctttccc cttctaaagg 420
gcaaaagtga gtatggtgcc tatctaacat ctcaatggct aaggcgtcga gcaaagcccg 480
cttatttttt acatgccaat acaatgtagg ctgctctaca cctagcttct gggcgagttt 540
acgggttgtt aaaccttcga ttccgacctc attaagcagc tctaatgcgc tgttaatcac 600
tttactttta tctaatctgg acatcattaa tgtttattga gctctcgaac cccagagtcc 660
cgcattattt gccgactacc ttggtgatct cgcctttcac gtagtggaca aattcttcca 720
actgatctgc gcgcgaggcc aagcgatctt cttcttgtcc aagataagcc tgtctagctt 780
caagtatgac gggctgatac tgggccggca ggcgctccat tgcccagtcg gcagcgacat 840
ccttcggcgc gattttgccg gttactgcgc tgtaccaaat gcgggacaac gtaagcacta 900
catttcgctc atcgccagcc cagtcgggcg gcgagttcca tagcgttaag gtttcattta 960
gcgcctcaaa tagatcctgt tcaggaaccg gatcaaagag ttcctccgcc gctggaccta 1020
ccaaggcaac gctatgttct cttgcttttg tcagcaagat agccagatca atgtcgatcg 1080
tggctggctc gaagatacct gcaagaatgt cattgcgctg ccattctcca aattgcagtt 1140
cgcgcttagc tggataacgc cacggaatga tgtcgtcgtg cacaacaatg gtgacttcta 1200
cagcgcggag aatctcgctc tctccagggg aagccgaagt ttccaaaagg tcgttgatca 1260
aagctcgccg cgttgtttca tcaagcctta cggtcaccgt aaccagcaaa tcaatatcac 1320
tgtgtggctt caggccgcca tccactgcgg agccgtacaa atgtacggcc agcaacgtcg 1380
gttcgagatg gcgctcgatg acgccaacta cctctgatag ttgagtcgat acttcggcga 1440
tcaccgcttc cctcatgatg tttaactttg ttttagggcg actgccctgc tgcgtaacat 1500
cgttgctgct ccataacatc aaacatcgac ccacggcgta acgcgcttgc tgcttggatg 1560
cccgaggcat agactgtacc ccaaaaaaac atgtcataac aagccatgaa aaccgccact 1620
gcgccgttac catgcgaaac gatcctcatc ctgtctcttg atcagatctt gatcccctgc 1680
gccatcagat ccttggcggc aagaaagcca tccagtttac tttgcagggc ttcccaacct 1740
taccagaggg cgccccagct ggcaattccg acgtc 1775

<210> SEQ ID NO 22
<211> LENGTH: 3204
<212> TYPE: DNA
<213> ORGANISM: Artificial
<220> FEATURE:
<223> OTHER INFORMATION: Complete sequence of pTET-SpecR expression vector

<400> SEQUENCE: 22

```
tcgagtccct atcagtgata gagattgaca tccctatcag tgatagagat actgagcaca     60

tcagcaggac gcactgaccg agttcattaa agaggagaaa gatacccatg ggcagcagcc    120

atcatcatca tcatcacagc agcggcctgg tgccgcgcgg cagccatatg ggtggcggtt    180

ctggatccgg aggcactagt ggtggcggct caggtaccta actcgagcac caccaccacc    240

accactgaga tccggctgct aacaaagccc gaaaggaagc tgagttggct gctgccaccg    300

ctgagcaata actagcataa cctctagagg catcaaataa aacgaaaggc tcagtcgaaa    360

gactgggcct ttcgttttat ctgttgtttg tcggtgaacg ctctcctgag taggacaaat    420

ccgccgccct agacctaggc gttcggctgc ggcgagcggt atcagctcac tcaaaggcgg    480

taatacggtt atccacagaa tcaggggata acgcaggaaa gaacatgtga gcaaaaggcc    540

agcaaaaggc caggaaccgt aaaaaggccg cgttgctggc gtttttccat aggctccgcc    600

cccctgacga gcatcacaaa aatcgacgct caagtcagag gtggcgaaac ccgacaggac    660

tataaagata ccaggcgttt ccccctggaa gctccctcgt gcgctctcct gttccgaccc    720

tgccgcttac cggatacctg tccgcctttc tcccttcggg aagcgtggcg ctttctcaat    780

gctcacgctg taggtatctc agttcggtgt aggtcgttcg ctccaagctg ggctgtgtgc    840

acgaaccccc cgttcagccc gaccgctgcg ccttatccgg taactatcgt cttgagtcca    900

acccggtaag acacgactta tcgccactgg cagcagccac tggtaacagg attagcagag    960

cgaggtatgt aggcggtgct acagagttct tgaagtggtg gcctaactac ggctacacta   1020

gaaggacagt atttggtatc tgcgctctgc tgaagccagt taccttcgga aaaagagttg   1080

gtagctcttg atccggcaaa caaaccaccg ctggtagcgg tggttttttt gtttgcaagc   1140

agcagattac gcgcagaaaa aaaggatctc aagaagatcc tttgatcttt tctacggggt   1200

ctgacgctca gtggaacgaa aactcacgtt aagggatttt ggtcatgact agcgcttgga   1260

ttctcaccaa taaaaaacgc ccggcggcaa ccgagcgttc tgaacaaatc cagatggagt   1320

tctgaggtca ttactggatc tatcaacagg agtccaagct taagacccac tttcacattt   1380

aagttgtttt tctaatccgt atatgatcaa ttcaaggccg aataagaagg ctggctctgc   1440

accttggtga tcaaataatt cgatagcttg tcgtaataat ggcggcatac tatcagtagt   1500

aggtgtttcc ctttcttctt tagcgacttg atgctcttga tcttccaata cgcaacctaa   1560

agtaaaatgc cccacagcgc tgagtgcata taatgcattc tctagtgaaa aaccttgttg   1620

gcataaaaag gctaattgat tttcgagagt ttcatactgt ttttctgtag gccgtgtacc   1680

taaatgtact tttgctccat cgcgatgact tagtaaagca catctaaaac ttttagcgtt   1740

attacgtaaa aaatcttgcc agctttcccc ttctaaaggg caaaagtgag tatggtgcct   1800

atctaacatc tcaatggcta aggcgtcgag caaagcccgc ttattttttta catgccaata   1860

caatgtaggc tgctctacac ctagcttctg ggcgagttta cgggttgtta aaccttcgat   1920

tccgacctca ttaagcagct ctaatgcgct gttaatcact ttacttttat ctaatctgga   1980

catcattaat gtttattgag ctctcgaacc ccagagtccc gcattatttg ccgactacct   2040

tggtgatctc gcctttcacg tagtggacaa attcttccaa ctgatctgcg cgcgaggcca   2100
```

agcgatcttc ttcttgtcca agataagcct gtctagcttc aagtatgacg ggctgatact 2160
gggccggcag gcgctccatt gcccagtcgg cagcgacatc cttcggcgcg attttgccgg 2220
ttactgcgct gtaccaaatg cgggacaacg taagcactac atttcgctca tcgccagccc 2280
agtcgggcgg cgagttccat agcgttaagg tttcatttag cgcctcaaat agatcctgtt 2340
caggaaccgg atcaaagagt tcctccgccg ctggacctac caaggcaacg ctatgttctc 2400
ttgcttttgt cagcaagata gccagatcaa tgtcgatcgt ggctggctcg aagatacctg 2460
caagaatgtc attgcgctgc cattctccaa attgcagttc gcgcttagct ggataacgcc 2520
acggaatgat gtcgtcgtgc acaacaatgg tgacttctac agcgcggaga atctcgctct 2580
ctccagggga agccgaagtt tccaaaaggt cgttgatcaa agctcgccgc gttgtttcat 2640
caagccttac ggtcaccgta accagcaaat caatatcact gtgtggcttc aggccgccat 2700
ccactgcgga gccgtacaaa tgtacggcca gcaacgtcgg ttcgagatgg cgctcgatga 2760
cgccaactac ctctgatagt tgagtcgata cttcggcgat caccgcttcc ctcatgatgt 2820
ttaactttgt tttagggcga ctgccctgct gcgtaacatc gttgctgctc cataacatca 2880
aacatcgacc cacggcgtaa cgcgcttgct gcttggatgc ccgaggcata gactgtaccc 2940
caaaaaaaca tgtcataaca agccatgaaa accgccactg cgccgttacc atgcgaaacg 3000
atcctcatcc tgtctcttga tcagatcttg atcccctgcg ccatcagatc cttggcggca 3060
agaaagccat ccagtttact ttgcagggct tcccaacctt accagagggc gccccagctg 3120
gcaattccga cgtctaagaa accattatta tcatgacatt aacctataaa aataggcgta 3180
tcacgaggcc ctttcgtctt cacc 3204

<210> SEQ ID NO 23
<211> LENGTH: 113
<212> TYPE: DNA
<213> ORGANISM: Artificial
<220> FEATURE:
<223> OTHER INFORMATION: Sequence encoding cloning cassette

<400> SEQUENCE: 23
ccatgggcag cagccatcat catcatcatc acagcagcgg cctggtgccg cgcggcagcc 60
atatgggtgg cggttctgga tccggaggca ctagtggtgg cggctcaggt acc 113

<210> SEQ ID NO 24
<211> LENGTH: 26
<212> TYPE: DNA
<213> ORGANISM: Artificial
<220> FEATURE:
<223> OTHER INFORMATION: synthetic oligonucleotide frame-shift stuffer

<400> SEQUENCE: 24
catatgtgtt aactgagtag gatccg 26

<210> SEQ ID NO 25
<211> LENGTH: 26
<212> TYPE: DNA
<213> ORGANISM: Artificial
<220> FEATURE:
<223> OTHER INFORMATION: synthetic oligonucleotide frame-shift stuffer

<400> SEQUENCE: 25
catatgtaat taattaattg gatccg 26

<210> SEQ ID NO 26
<211> LENGTH: 40
<212> TYPE: DNA

<213> ORGANISM: Artificial
<220> FEATURE:
<223> OTHER INFORMATION: synthetic oligonucleotide primer

<400> SEQUENCE: 26
caggatgagg atcgtttcgc atggtaacgg cgcagtggcg 40

<210> SEQ ID NO 27
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 27
cgccactgcg ccgttaccat gcgaaacgat cctcatcctg 40

<210> SEQ ID NO 28
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 28
gcattatttg ccgactacct tggtgatctc gcc 33

<210> SEQ ID NO 29
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 29
accccagagt cccgcattat ttgccgacta cctt 34

<210> SEQ ID NO 30
<211> LENGTH: 63
<212> TYPE: DNA
<213> ORGANISM: Artificial
<220> FEATURE:
<223> OTHER INFORMATION: synthetic oligonucleotide stuffer

<400> SEQUENCE: 30
catatgggtg gcggttctgg atccggaggc actagtggtg gcggctcagg tacctaactc 60
gag 63

<210> SEQ ID NO 31
<211> LENGTH: 45
<212> TYPE: DNA
<213> ORGANISM: Artificial
<220> FEATURE:
<223> OTHER INFORMATION: synthetic oligonucleotide stuffer

<400> SEQUENCE: 31
catatgggtg gcactagtgg tggcggctca ggtacctaac tcgag 45

<210> SEQ ID NO 32
<211> LENGTH: 14
<212> TYPE: DNA
<213> ORGANISM: Artificial
<220> FEATURE:
<223> OTHER INFORMATION: modified Shine-Delgarno sequence

<400> SEQUENCE: 32

-continued aataaacatt aatg 14

<210> SEQ ID NO 33
<211> LENGTH: 596
<212> TYPE: DNA
<213> ORGANISM: Artificial
<220> FEATURE:
<223> OTHER INFORMATION: GFP variant; sequence encoding fragment corresponding to -strands 1-9 OPT

<400> SEQUENCE: 33

```
atgcgcaaag gagaagaact tttcactgga gttgtcccaa ttcttgttga attagatggt     60

gatgttaatg ggcacaaatt ttctgtccgt ggagagggtg aaggtgatgc tacaaacgga    120

aaactcagcc ttaaatttat ttgcactact ggaaaactac ctgttccatg gccaacactt    180

gtcactactc tgacctatgg tgttcaatgc ttttcccgtt atccggatca catgaaacgg    240

catgactttt tcaagagtgt catgcccgaa ggttatgtac aggaacgcac tatatctttc    300

aaagatgacg ggacctacaa gacgcgtgct gaagtcaagt ctgaaggtga tacccttgtt    360

aatcgtatcg agttaaaagg tattgatttt aaagaagatg gaaacattct cggacacaaa    420

ctcgagtaca actttaactc acacaatgta tacatcacgg cagacaaaca aaagaatgga    480

atcaaagcta acttcacaat tcgccacaac gttgaagatg gttccgttca actagcagac    540

cattatcaac aaaatactcc aattggcgat ggccctgtcc ttttaccaga caataa        596
```

<210> SEQ ID NO 34
<211> LENGTH: 197
<212> TYPE: PRT
<213> ORGANISM: Artificial
<220> FEATURE:
<223> OTHER INFORMATION: GFP variant; fragment corresponding to -strands 1-9 OPT

<400> SEQUENCE: 34

```
Met Arg Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Val Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Ser Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190
```

Val Leu Leu Pro Asp
195

<210> SEQ ID NO 35
<211> LENGTH: 41
<212> TYPE: PRT
<213> ORGANISM: Artificial
<220> FEATURE:
<223> OTHER INFORMATION: GFP variant; fragment corresponding to -strands 10-11

<400> SEQUENCE: 35

Asn His Tyr Leu Ser Thr Gln Ser Val Leu Ser Lys Asp Pro Asn Glu
1 5 10 15

Lys Arg Asp His Met Val Leu Leu Glu Phe Val Thr Ala Ala Gly Ile
20 25 30

Thr His Gly Met Asp Glu Leu Tyr Lys
35 40

<210> SEQ ID NO 36
<211> LENGTH: 41
<212> TYPE: PRT
<213> ORGANISM: Artificial
<220> FEATURE:
<223> OTHER INFORMATION: GFP variant; fragment corresponding to -strands 10-11, optimized

<400> SEQUENCE: 36

Asp His Tyr Leu Ser Thr Gln Thr Ile Leu Ser Lys Asp Pro Asn Glu
1 5 10 15

Glu Arg Asp His Met Val Leu Leu Glu Ser Val Thr Ala Ala Gly Ile
20 25 30

Thr His Gly Met Asp Glu Leu Tyr Lys
35 40

<210> SEQ ID NO 37
<211> LENGTH: 8
<212> TYPE: PRT
<213> ORGANISM: Artificial
<220> FEATURE:
<223> OTHER INFORMATION: polypeptide linker sequence

<400> SEQUENCE: 37

Gly Gly Gly Ser Gly Ser Gly Gly
1 5

<210> SEQ ID NO 38
<211> LENGTH: 71
<212> TYPE: PRT
<213> ORGANISM: Artificial
<220> FEATURE:
<223> OTHER INFORMATION: GFP variant; fragment corresponding to -strands 10-11 with intervening polypeptide linker sequences

<400> SEQUENCE: 38

Tyr Thr Met Asp Leu Pro Asp Asn His Tyr Leu Ser Thr Gln Thr Ile
1 5 10 15

Leu Leu Lys Asp Leu Asn Gly Thr Gly Val Gly Ser Gly Gly Gly Ser
20 25 30

His Met Gly Gly Gly Ser Gly Ser Gly Gly Gly Ser Gly Gly Gly Ser
35 40 45

Thr Ser Glu Lys Arg Asp His Met Val Leu Leu Glu Tyr Val Thr Ala
50 55 60

Ala Gly Ile Thr Asp Ala Ser 65 70

<210> SEQ ID NO 39
<211> LENGTH: 71
<212> TYPE: PRT
<213> ORGANISM: Artificial
<220> FEATURE:
<223> OTHER INFORMATION: Sequence of "10-X-11 sandwich optimum" fragment

<400> SEQUENCE: 39

Tyr Thr Met Asp Leu Pro Asp Asp His Tyr Leu Ser Thr Gln Thr Ile
1 5 10 15

Leu Ser Lys Asp Leu Asn Gly Thr Asp Val Gly Ser Gly Gly Gly Ser
20 25 30

His Met Gly Gly Gly Ser Gly Ser Gly Gly Gly Ser Gly Gly Gly Ser
35 40 45

Thr Ser Glu Lys Arg Asp His Met Val Leu Leu Glu Tyr Val Thr Ala
50 55 60

Ala Gly Ile Thr Asp Ala Ser
65 70

<210> SEQ ID NO 40
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 40
gatataacta gtcatgacca catgcacctt catgag 36

<210> SEQ ID NO 41
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 41
cacatgcacc ttcatgagca tgtacatgct cat 33

<210> SEQ ID NO 42
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 42
gatataggta cccccatgag catgtacatg ctcatgaagg tgca 44

<210> SEQ ID NO 43
<211> LENGTH: 693
<212> TYPE: DNA
<213> ORGANISM: Artificial
<220> FEATURE:
<223> OTHER INFORMATION: GFP variant; Sequence encoding GFP 1-10 OPT+GFP
S11M2

<400> SEQUENCE: 43
atgagcaaag gagaagaact tttcactgga gttgtcccaa ttcttgttga attagatggt 60
gatgttaatg ggcacaaatt ttctgtcaga ggagagggtg aaggtgatgc tacaatcgga 120
aaactcaccc ttaaatttat ttgcactact ggaaaactac ctgttccatg gccaacactt 180

```
gtcactactc tgacctatgg tgttcaatgc ttttcccgtt atccggatca catgaaaagg    240

catgactttt tcaagagtgc catgcccgaa ggttatgtac aggaacgcac tatatctttc    300

aaagatgacg ggaaatacaa gacgcgtgct gtagtcaagt ttgaaggtga tacccttgtt    360

aatcgtatcg agttaaaggg tactgatttt aaagaagatg gaaacattct cggacacaaa    420

ctcgagtaca actttaactc acacaatgta tacatcacgg cagacaaaca aaagaatgga    480

atcaaagcta acttcacagt tcgccacaac gttgaagatg gttccgttca actagcagac    540

cattatcaac aaaatactcc aattggcgat ggccctgtcc ttttaccaga caaccattac    600

ctgtcgacac aaactgtcct ttcgaaagat cccaacgaaa agcgtgacca catggtcctt    660

catgagtctg taaatgctgc tgggattaca taa                                 693
```

<210> SEQ ID NO 44
<211> LENGTH: 230
<212> TYPE: PRT
<213> ORGANISM: Artificial
<220> FEATURE:
<223> OTHER INFORMATION: GFP variant; GFP 1-10 OPT + GFP S11 M2 amino acid sequence

<400> SEQUENCE: 44

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Arg Asp His Met Val Leu His Glu Ser Val
    210                 215                 220

Asn Ala Ala Gly Ile Thr
225                 230
```

<210> SEQ ID NO 45
<211> LENGTH: 717
<212> TYPE: DNA
<213> ORGANISM: Artificial
<220> FEATURE:

<223> OTHER INFORMATION: GFP variant; Sequence encoding GFP 1-10 OPT +
GFP S11 M2+ GFP tail

<400> SEQUENCE: 45
atgagcaaag gagaagaact tttcactgga gttgtcccaa ttcttgttga attagatggt 60
gatgttaatg ggcacaaatt ttctgtcaga ggagagggtg aaggtgatgc tacaatcgga 120
aaactcaccc ttaaatttat ttgcactact ggaaaactac ctgttccatg gccaacactt 180
gtcactactc tgacctatgg tgttcaatgc ttttcccgtt atccggatca catgaaaagg 240
catgactttt tcaagagtgc catgcccgaa ggttatgtac aggaacgcac tatatctttc 300
aaagatgacg ggaaatacaa gacgcgtgct gtagtcaagt ttgaaggtga tacccttgtt 360
aatcgtatcg agttaaaggg tactgatttt aaagaagatg gaaacattct cggacacaaa 420
ctcgagtaca actttaactc acacaatgta tacatcacgg cagacaaaca aaagaatgga 480
atcaaagcta acttcacagt tcgccacaac gttgaagatg gttccgttca actagcagac 540
cattatcaac aaaatactcc aattggcgat ggccctgtcc ttttaccaga caaccattac 600
ctgtcgacac aaactgtcct ttcgaaagat cccaacgaaa agcgtgacca catggtcctt 660
catgagtctg taaatgctgc tgggattaca catggcatgg atgagctcta caaataa 717

<210> SEQ ID NO 46
<211> LENGTH: 238
<212> TYPE: PRT
<213> ORGANISM: Artificial
<220> FEATURE:
<223> OTHER INFORMATION: GFP variant; GFP 1-10 OPT + GFP S11 M2 + GFP
tail amino acid sequence

<400> SEQUENCE: 46

Met Ser Lys Gly Glu Glu Leu Phe Thr Gly Val Val Pro Ile Leu Val
1 5 10 15

Glu Leu Asp Gly Asp Val Asn Gly His Lys Phe Ser Val Arg Gly Glu
20 25 30

Gly Glu Gly Asp Ala Thr Ile Gly Lys Leu Thr Leu Lys Phe Ile Cys
35 40 45

Thr Thr Gly Lys Leu Pro Val Pro Trp Pro Thr Leu Val Thr Thr Leu
50 55 60

Thr Tyr Gly Val Gln Cys Phe Ser Arg Tyr Pro Asp His Met Lys Arg
65 70 75 80

His Asp Phe Phe Lys Ser Ala Met Pro Glu Gly Tyr Val Gln Glu Arg
85 90 95

Thr Ile Ser Phe Lys Asp Asp Gly Lys Tyr Lys Thr Arg Ala Val Val
100 105 110

Lys Phe Glu Gly Asp Thr Leu Val Asn Arg Ile Glu Leu Lys Gly Thr
115 120 125

Asp Phe Lys Glu Asp Gly Asn Ile Leu Gly His Lys Leu Glu Tyr Asn
130 135 140

Phe Asn Ser His Asn Val Tyr Ile Thr Ala Asp Lys Gln Lys Asn Gly
145 150 155 160

Ile Lys Ala Asn Phe Thr Val Arg His Asn Val Glu Asp Gly Ser Val
165 170 175

Gln Leu Ala Asp His Tyr Gln Gln Asn Thr Pro Ile Gly Asp Gly Pro
180 185 190

Val Leu Leu Pro Asp Asn His Tyr Leu Ser Thr Gln Thr Val Leu Ser
195 200 205

Lys Asp Pro Asn Glu Lys Arg Asp His Met Val Leu His Glu Ser Val

```
    210                 215                 220

Asn Ala Ala Gly Ile Thr His Gly Met Asp Glu Leu Tyr Lys
225                 230                 235


<210> SEQ ID NO 47
<211> LENGTH: 124
<212> TYPE: DNA
<213> ORGANISM: Artificial
<220> FEATURE:
<223> OTHER INFORMATION: GFP variant; Sequence encoding fragment
      corresponding to -strands 10-11 OPT

<400> SEQUENCE: 47

gaccattacc tgtcgacaca aactatcctt tcgaaagatc ccaacgaaga gcgtgaccac      60

atggtccttc ttgagtctgt aactgctgct gggattacac atggcatgga tgagctctac     120

aaat                                                                  124


<210> SEQ ID NO 48
<211> LENGTH: 230
<212> TYPE: DNA
<213> ORGANISM: Artificial
<220> FEATURE:
<223> OTHER INFORMATION: GFP variant; Sequence encoding "10-X-11
      sandwich optimum" fragment

<400> SEQUENCE: 48

gatataccat ggatttacca gacgaccatt acctgtcgac acaaactatc ctttcgaaag      60

atctcaacgg taccgacgtt gggtctggcg gtggctccca tatgggtggc ggttctggat     120

ccggtggagg gtctggtggc ggatcaacta gtgaaaagcg tgaccacatg gtccttcttg     180

agtatgtaac tgctgctggg attacaggtg ctagctaact cgagaatagc                230


<210> SEQ ID NO 49
<211> LENGTH: 71
<212> TYPE: PRT
<213> ORGANISM: Artificial
<220> FEATURE:
<223> OTHER INFORMATION: Synthetic polypeptide

<400> SEQUENCE: 49

Tyr Thr Met Gly Leu Pro Asp Asn His Tyr Leu Ser Thr Gln Ser Val
1               5                   10                  15

Leu Ser Lys Asp Pro Asn Gly Thr Gly Gly Gly Ser Gly Gly Gly Ser
            20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Phe Val Thr Ala
    50                  55                  60

Ala Gly Ile Thr Gly Ala Ser
65                  70


<210> SEQ ID NO 50
<211> LENGTH: 71
<212> TYPE: PRT
<213> ORGANISM: Artificial
<220> FEATURE:
<223> OTHER INFORMATION: Synthetic polypeptide

<400> SEQUENCE: 50

Tyr Thr Met Asp Leu Pro Asp Asn His Tyr Leu Ser Thr Gln Thr Ile
1               5                   10                  15

Leu Leu Lys Asp Leu Asn Gly Thr Gly Val Gly Ser Gly Gly Gly Ser
```

-continued

```
            20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Tyr Val Thr Ala
    50                  55                  60

Ala Gly Ile Thr Asp Ala Ser
65                  70


<210> SEQ ID NO 51
<211> LENGTH: 71
<212> TYPE: PRT
<213> ORGANISM: Artificial
<220> FEATURE:
<223> OTHER INFORMATION: Synthetic polypeptide

<400> SEQUENCE: 51

Tyr Thr Met Asp Leu Pro Asp Asn His Tyr Leu Ser Thr Gln Thr Ile
1               5                   10                  15

Leu Leu Lys Asp Leu Asn Gly Thr Gly Val Gly Ser Gly Gly Gly Ser
            20                  25                  30

His Met Gly Gly Gly Ser Gly Ser Gly Gly Glu Ser Gly Gly Gly Ser
        35                  40                  45

Thr Gly Glu Lys Arg Asp His Met Val Leu Leu Glu Tyr Val Thr Ala
    50                  55                  60

Ala Gly Ile Thr Gly Ala Ser
65                  70


<210> SEQ ID NO 52
<211> LENGTH: 71
<212> TYPE: PRT
<213> ORGANISM: Artificial
<220> FEATURE:
<223> OTHER INFORMATION: Synthetic polypeptide

<400> SEQUENCE: 52

Tyr Thr Met Asp Leu Pro Asp Asn His Tyr Leu Ser Thr Gln Thr Ile
1               5                   10                  15

Leu Leu Lys Asp Leu Asn Gly Thr Gly Val Gly Ser Gly Gly Gly Ser
            20                  25                  30

His Met Gly Gly Gly Ser Gly Ser Gly Gly Gly Ser Gly Gly Gly Ser
        35                  40                  45

Thr Ser Glu Lys Arg Asp His Met Val Leu Leu Glu Tyr Val Thr Ala
    50                  55                  60

Ala Gly Ile Thr Asp Ala Ser
65                  70


<210> SEQ ID NO 53
<211> LENGTH: 71
<212> TYPE: PRT
<213> ORGANISM: Artificial
<220> FEATURE:
<223> OTHER INFORMATION: Synthetic polypeptide

<400> SEQUENCE: 53

Tyr Thr Met Asp Leu Pro Asp Asn His Tyr Leu Ser Thr Gln Thr Ile
1               5                   10                  15

Leu Leu Lys Asp Leu Asn Gly Thr Asp Val Gly Ser Gly Gly Gly Ser
            20                  25                  30

His Met Gly Gly Gly Ser Gly Ser Asp Gly Gly Ser Gly Gly Gly Ser
        35                  40                  45
```

```
Thr Gly Glu Lys Arg Asp His Met Val Leu Leu Glu Tyr Val Thr Ala
    50                  55                  60

Ala Gly Ile Thr Gly Ala Ser
65                  70


<210> SEQ ID NO 54
<211> LENGTH: 71
<212> TYPE: PRT
<213> ORGANISM: Artificial
<220> FEATURE:
<223> OTHER INFORMATION: Synthetic polypeptide

<400> SEQUENCE: 54

Tyr Thr Met Asp Leu Pro Asp Asn His Tyr Leu Ser Thr Gln Thr Ile
1               5                   10                  15

Leu Leu Lys Asp Leu Asn Gly Thr Gly Gly Gly Ser Gly Asp Gly Cys
            20                  25                  30

His Met Asp Gly Gly Ser Gly Ser Gly Gly Gly Ser Gly Gly Gly Ser
        35                  40                  45

Thr Gly Glu Lys Arg Asp His Met Val Leu Leu Glu Tyr Val Thr Ala
    50                  55                  60

Ala Gly Ile Thr Gly Ala Ser
65                  70


<210> SEQ ID NO 55
<211> LENGTH: 25
<212> TYPE: PRT
<213> ORGANISM: Artificial
<220> FEATURE:
<223> OTHER INFORMATION: Synthetic polypeptide

<400> SEQUENCE: 55

Gly Pro Val Leu Leu Pro Asp Asn His Tyr Leu Ser Thr Gln Thr Val
1               5                   10                  15

Leu Ser Lys Asp Pro Asn Glu Lys Gly
            20                  25


<210> SEQ ID NO 56
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 56

ggccctgtcc ttttaccann naaccattac ctgtcgaca                            39


<210> SEQ ID NO 57
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 57

cctgtccttt taccagacnn ncattacctg tcgacacaa                            39
```

<210> SEQ ID NO 58
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 58
gtccttttac cagacaacnn ntacctgtcg acacaaact 39

<210> SEQ ID NO 59
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 59
cttttaccag acaaccatnn nctgtcgaca caaactgtc 39

<210> SEQ ID NO 60
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 60
ttaccagaca accattacnn ntcgacacaa actgtcctt 39

<210> SEQ ID NO 61
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 61
ccagacaacc attacctgnn nacacaaact gtcctttcg 39

<210> SEQ ID NO 62
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 62
gacaaccatt acctgtcgnn ncaaactgtc ctttcgaaa 39

<210> SEQ ID NO 63
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 63
aaccattacc tgtcgacann nactgtcctt tcgaaagat 39

<210> SEQ ID NO 64
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 64
cattacctgt cgacacaann ngtcctttcg aaagatccc 39

<210> SEQ ID NO 65
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 65
tacctgtcga cacaaactnn nctttcgaaa gatcccaac 39

<210> SEQ ID NO 66
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 66
ctgtcgacac aaactgtcnn ntcgaaagat cccaacgaa 39

<210> SEQ ID NO 67
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 67
tcgacacaaa ctgtccttnn naaagatccc aacgaaaag 39

<210> SEQ ID NO 68
<211> LENGTH: 38
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (18)..(20)
<223> OTHER INFORMATION: n is a, c, g, or t

<400> SEQUENCE: 68
acacaaactg tccttcgnnn gatcccaacg aaaagtaa 38

<210> SEQ ID NO 69
<211> LENGTH: 39
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (19)..(21)
<223> OTHER INFORMATION: n is a, c, g, or t

<400> SEQUENCE: 69
caaactgtcc tttcgaaann ncccaacgaa aagtaaggt 39

<210> SEQ ID NO 70
<211> LENGTH: 81
<212> TYPE: DNA
<213> ORGANISM: Artificial
<220> FEATURE:
<223> OTHER INFORMATION: Coding sequence for SEQ ID NO: 55

<400> SEQUENCE: 70
ggccctgtcc ttttaccaga caaccattac ctgtcgacac aaactgtcct ttcgaaagat 60
cccaacgaaa agtaaggtac c 81

<210> SEQ ID NO 71
<211> LENGTH: 81
<212> TYPE: DNA
<213> ORGANISM: Artificial
<220> FEATURE:
<223> OTHER INFORMATION: Complement strand of SEQ ID NO: 70

<400> SEQUENCE: 71
ccgggacagg aaaatggtct gttggtaatg gacagctgtg tttgacagga aagctttcta 60
gggttgcttt tcattccatg g 81

<210> SEQ ID NO 72
<211> LENGTH: 33
<212> TYPE: DNA
<213> ORGANISM: Artificial
<220> FEATURE:
<223> OTHER INFORMATION: Synthetic (reverse) Primer

<400> SEQUENCE: 72
gaaagctttc tagggttgct tttcattcca tgg 33

<210> SEQ ID NO 73
<211> LENGTH: 39
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 73

```
Xaa Asp Leu Xaa Asp Asp Xaa Tyr Leu Ser Thr Gln Thr Ile Leu Ser
1               5                   10                  15

Lys Asp Leu Asn Gly Thr Asp Val Gly Ser Gly Gly Gly Ser His Met
            20                  25                  30

Lys Leu Gln Val Ala Leu Asp
        35
```

<210> SEQ ID NO 74
<211> LENGTH: 40
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 74

```
Pro Xaa Asp Leu Xaa Asp Asp Xaa Tyr Leu Ser Thr Gln Thr Ile Leu
1               5                   10                  15

Ser Lys Asp Leu Asn Gly Thr Gly Val Gly Ser Gly Gly Gly Ser His
            20                  25                  30

Met Lys Leu Gln Val Ala Leu Asp
        35                  40
```

<210> SEQ ID NO 75
<211> LENGTH: 41
<212> TYPE: PRT
<213> ORGANISM: Artificial
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 75

```
Pro Xaa Asp Leu Xaa Asp Asp Xaa Tyr Leu Ser Thr Gln Thr Ile Leu
1               5                   10                  15

Ser Lys Asp Leu Asn Gly Thr Gly Val Gly Ser Gly Gly Gly Ser His
            20                  25                  30
```

Met Lys Leu Gln Val Ala Leu Asp Leu
35 40

<210> SEQ ID NO 76
<211> LENGTH: 44
<212> TYPE: PRT
<213> ORGANISM: Artificial
<220> FEATURE:
<223> OTHER INFORMATION: Synthetic polypeptide

<400> SEQUENCE: 76

Ile Pro Met Asp Leu Pro Asp Asp His Tyr Leu Ser Thr Gln Thr Ile
1 5 10 15

Leu Ser Lys Asp Leu Asn Gly Thr Gly Val Gly Ser Gly Gly Gly Ser
20 25 30

His Met Lys Leu Gln Val Ala Leu Asp Leu Val Asp
35 40

<210> SEQ ID NO 77
<211> LENGTH: 41
<212> TYPE: PRT
<213> ORGANISM: Artificial
<220> FEATURE:
<223> OTHER INFORMATION: Synthetic polypeptide

<400> SEQUENCE: 77

Asp Leu Pro Asp Asp His Tyr Leu Ser Thr Gln Thr Ile Leu Ser Lys
1 5 10 15

Asp Leu Asn Gly Thr Gly Val Gly Ser Asp Gly Gly Ser His Met Lys
20 25 30

Leu Gln Val Ala Leu Asp Leu Val Asp
35 40

<210> SEQ ID NO 78
<211> LENGTH: 43
<212> TYPE: PRT
<213> ORGANISM: Artificial
<220> FEATURE:
<223> OTHER INFORMATION: Synthetic polypeptide

<400> SEQUENCE: 78

Ile Pro Met Asp Leu Pro Asp Asp His Tyr Leu Ser Thr Gln Thr Ile
1 5 10 15

Leu Ser Lys Asp Leu Asn Gly Thr Asp Val Gly Ser Gly Gly Gly Ser
20 25 30

His Met Lys Leu Gln Val Ala Leu Asp Leu Val
35 40

<210> SEQ ID NO 79
<211> LENGTH: 45
<212> TYPE: PRT
<213> ORGANISM: Artificial
<220> FEATURE:
<223> OTHER INFORMATION: Synthetic polypeptide

<400> SEQUENCE: 79

Ile Pro Met Asp Leu Pro Asp Asp His Tyr Leu Ser Thr Gln Thr Ile
1 5 10 15

Leu Ser Lys Asp Leu Asn Gly Thr Gly Val Gly Ser Gly Gly Gly Ser
20 25 30

His Met Lys Leu Gln Val Ala Leu Asp Leu Val Asp Leu
35 40 45

-continued

```
<210> SEQ ID NO 80
<211> LENGTH: 44
<212> TYPE: PRT
<213> ORGANISM: Artificial
<220> FEATURE:
<223> OTHER INFORMATION: Synthetic polypeptide

<400> SEQUENCE: 80

Ile Pro Met Asp Leu Pro Asp Asp His Tyr Leu Ser Thr Gln Thr Ile
1               5                   10                  15

Leu Ser Lys Asp Leu Asn Gly Thr Gly Val Gly Ser Gly Gly Gly Ser
            20                  25                  30

His Met Lys Leu Gln Val Ala Leu Asp Leu Val Asp
        35                  40


<210> SEQ ID NO 81
<211> LENGTH: 7
<212> TYPE: PRT
<213> ORGANISM: Tobacco etch virus

<400> SEQUENCE: 81

Glu Asn Leu Tyr Phe Gln Gly
1               5
```

NUCLEIC ACID ENCODING A SELF-ASSEMBLING SPLIT-FLUORESCENT PROTEIN SYSTEM

RELATED APPLICATIONS

This is a Divisional of U.S. patent application No. 10/973,693, filed Oct. 25, 2004, which issued at U.S. Pat. No. 7,955,821 on Jun. 7, 2011, and which claims the benefit of U.S. Provisional Patent Application No. 60/514,363, filed Oct. 24, 2003. All of the prior applications are hereby incorporated by reference.

STATEMENT AS TO RIGHTS TO INVENTIONS MADE UNDER FEDERALLY SPONSORED RESEARCH OR DEVELOPMENT

This invention was made with government support under grant number DE -FG02-98ER62647 from the United States Department of Energy and Contract No. W-7405-ENG-36 awarded by the United States Department of Energy to The Regents of The University of California. The government has certain rights in this invention.

STATEMENT REGARDING COLOR DRAWINGS

This patent or application file contains at least one drawing executed in color. Copies of this patent or patent application publication with color drawings will be provided by the United States Patent and Trademark Office upon request and payment of the necessary fee.

BACKGROUND OF THE INVENTION

Obtaining sufficient amounts of soluble, well-folded recombinant proteins for downstream applications remains a significant bottleneck in many fields that apply protein expression technologies (Makrides 1996; Baneyx 1999; Fahnert, Lilie et al. 2004), including structural genomics projects (Yokoyama 2003; Goh, Lan et al. 2004; Terwilliger 2004). Current approaches for maximizing soluble protein include screening large numbers of protein variants (mutants, fragments, fusion tags, folding partners), and testing many expression or refolding conditions (Armstrong, de Lencastre et al. 1999; Fahnert, Lilie et al. 2004). Several methods have recently been developed to screen proteins for soluble expression (Waldo 2003), including antibody detection of polyhistidine-tagged proteins in dot-blots (Knaust and Nordlund 2001), but these approaches require multiple steps and do not work in vivo. Proteins tagged with the lacZα fragment can be detected after structural complementation with lacZΩ (Ullmann, Jacob et al. 1967; Nixon and Benkovic 2000; Wigley, Stidham et al. 2001; Wehrman, Kleaveland et al. 2002), but the lacZα fragment is relatively large (52 amino acids) (Wigley, Stidham et al. 2001), and there have been no detailed studies regarding its effects on fusion partner folding and solubility. Proteins tagged with the 15 amino acid S-peptide (Kim and Raines 1993) can be quantified in vitro using a sensitive fluorogenic substrate (Kelemen, Klink et al. 1999) (FretWorks®, Novagen, Madison, Wis.) after complementation with the S-protein (Richards and Vithayathil 1959), but the assay cannot be used to assess soluble protein expression in vivo in *E. coli.*

GFP and its numerous related fluorescent proteins are now in widespread use as protein tagging agents (for review, see Verkhusha et al., 2003, *GFP-like fluorescent proteins and chromoproteins of the class Anthozoa*. In: Protein Structures: Kaleidescope of Structural Properties and Functions, Ch. 18, pp. 405-439, Research Signpost, Kerala, India). In addition, GFP has been used as a solubility reporter of terminally fused test proteins (Waldo et al., 1999, *Nat. Biotechnol.* 17:691-695; U.S. Pat. No. 6,448,087, entitled 'Method for Determining and Modifying Protein/Peptide Solubility'). GFP-like proteins are an expanding family of homologous, 25-30 kDa polypeptides sharing a conserved 11 beta-strand "barrel" structure. The GFP-like protein family currently comprises some 100 members, cloned from various *Anthozoa* and *Hydrozoa* species, and includes red, yellow and green fluorescent proteins and a variety of non-fluorescent chromoproteins (Verkhusha et al., supra). A wide variety of fluorescent protein labeling assays and kits are commercially available, encompassing a broad spectrum of GFP spectral variants and GFP-like fluorescent proteins, including DsRed and other red fluorescent proteins (Clontech, Palo Alto, Calif.; Amersham, Piscataway, N.J.).

Various strategies for improving the solubility of GFP and related proteins have been documented, and have resulted in the generation of numerous mutants having improved folding, solubility and perturbation tolerance characteristics. Stemmer and coworkers applied directed evolution to screen for mutants or variants of GFP that exhibited increased fluorescence and folding yield in *E. coli* (see, e.g., Crameri et al., Nat. Biotechnol. 143:315-319, 1996). They identified a mutant that exhibited increased folding ability. This version of GFP, termed cycle-3 or GFP3 contains the mutations F99S, M153T and V163A. GFP3 is relatively insensitive to the expression environment and folds well in a wide variety of hosts, including *E. coli*. GFP3 folds equally well at 27° C. and 37° C. Thus, the GFP3 mutations also appear to eliminate potential temperature sensitive folding intermediates that occur during folding of wild type GFP.

GFP3 can be made to misfold by expression as a fusion protein with another poorly folded polypeptide. GFP3 has been used to report on the "folding robustness" of N-terminally fused proteins during expression in *E. coli* (Waldo et al., 1999, supra). In this method, the sequence of the reporter, e.g., GFP3 domain, remains constant and a poorly folded upstream domain is mutated. Better folded variants of domain X are identified by increased fluorescence.

Existing protein tagging and detection platforms are powerful but have drawbacks. Split protein tags can perturb protein solubility (Ullmann, Jacob et al. 1967; Nixon and Benkovic 2000; Fox, Kapust et al. 2001; Wigley, Stidham et al. 2001; Wehrman, Kleaveland et al. 2002) or may not work in living cells (Richards and Vithayathil 1959; Kim and Raines 1993; Kelemen, Klink et al. 1999). Green fluorescent protein fusions can misfold (Waldo, Standish et al. 1999) or exhibit altered processing (Bertens, Heijne et al. 2003). Fluorogenic biarsenical FLaSH or ReASH (Adams, Campbell et al. 2002) substrates overcome many of these limitations, but require a polycysteine tag motif, a reducing environment, and cell transfection or permeabilization (Adams, Campbell et al. 2002).

GFP fragment reconstitution systems have been described, mainly for detecting protein-protein interactions, but none are capable of unassisted self-assembly into a correctly-folded, soluble and fluorescent re-constituted GFP, and no general split GFP folding reporter system has emerged from these approaches. For example, Ghosh et al, 2000, reported that two GFP fragments, corresponding to amino acids 1-157 and 158-238 of the GFP structure, could be reconstituted to yield a fluorescent product, in vitro or by coexpression in *E. coli*, when the individual fragments were fused to coiled-coil sequences capable of forming an antiparallel leucine zipper (Ghosh et al., 2000, *Antiparallel leucine zipper-directed protein reassembly: application to the green fluorescent protein*. J. Am. Chem. Soc. 122: 5658-5659). Likewise, U.S. Pat. No. 6,780,599 describes the use of helical coils capable of forming anti-parallel leucine zippers to join split fragments of the GFP molecule. The patent specification establishes that reconstitution does not occur in the absence of complementary helical coils attached to the GFP fragments. In particular, the specification notes that control experiments in which GFP fragments without leucine zipper pairs "failed to show any green colonies, thus emphasizing the requirement for the presence of both NZ and CZ leucine zippers to mediate GFP assembly in vivo and in vitro."

Similarly, Hu et al., 2002, showed that the interacting proteins bZIP and Rel, when fused to two fragments of GFP, can mediate GFP reconstitution by their interaction (Hu et al., 2002, *Visualization of interactions among bZIP and Rel family proteins in living cells using bimolecular fluorescence complementation*. Mol. Cell. 9: 789-798). Nagai et al., 2001, showed that fragments of yellow fluorescent protein (YFP) fused to calmodulin and M13 could mediate the reconstitution of YFP in the presence of calcium (Nagai et al., 2001, *Circularly permuted green fluorescent proteins engineered to sense* $Ca^{2}$+. Proc. Natl. Acad. Sci. USA 98: 3197-3202). In a variation of this approach, Ozawa at al. fused calmodulin and M13 to two GFP fragments via self-splicing intein polypeptide sequences, thereby mediating the covalent reconstitution of the GFP fragments in the presence of calcium (Ozawa et al., 2001, *A fluorescent indicator for detecting protein-protein interactions in vivo based on protein splicing*. Anal. Chem. 72: 5151-5157; Ozawa et al., 2002, *Protein splicing-based reconstitution of split green fluorescent protein for monitoring protein-protein interactions in bacteria: improved sensitivity and reduced screening time*. Anal. Chem. 73: 5866-5874). One of these investigators subsequently reported application of this splicing-based GFP reconstitution system to cultured mammalian cells (Umezawa, 2003, Chem. Rec. 3: 22-28). More recently, Zhang et al., 2004, showed that the helical coil split GFP system of Ghosh et al., 2000, supra, could be used to reconstitute GFP (as well as YFP and CFP) fluorescence when coexpressed in *C. elegans*, and demonstrated the utility of this system in confirming coexpression in vivo (Zhang et al., 2004, *Combinatorial marking of cells and organelles with reconstituted fluorescent proteins*. Cell 119: 137-144).

Although the aforementioned GFP reconstitution systems provide advantages over the use of two spectrally distinct fluorescent protein tags, they are limited by the size of the fragments and correspondingly poor folding characteristics (Ghosh et al., Hu et al., supra), the requirement for a chemical ligation or fused interacting partner polypeptides to force reconstitution (Ghosh et al., 2000, supra; Ozawa et al., 2001, 2002 supra; Zhang et al., 2004, supra), and co-expression or co-refolding to produce detectable folded and fluorescent GFP (Ghosh et al., 2000; Hu et al., 2001, supra). Poor folding characteristics limit the use of these fragments to applications wherein the fragments are simultaneously expressed or simultaneously refolded together. Such fragments are not useful for in vitro assays requiring the long-term stability and solubility of the respective fragments prior to complementation. An example of an application for which such split protein fragments are not useful would be the quantification of polypeptides tagged with one member of the split protein pair, and subsequently detected by the addition of the complementary fragment.

An ideal protein tag would be genetically encoded, could work both in vivo and in vitro, provide a sensitive analytical signal, and would not require external chemical reagents or substrates. However, to date, a split fluorescent protein tagging system that does not rely upon the use of fused heterologous polypeptide domains to drive reconstitution of the fluorescent reporter activity has not been described. A split-fluorescent protein tagging system in which the fragments are capable of spontaneously self-associating without the need for fused interacting protein domains, remain soluble prior to association, and does not change the solubility of fused target proteins is needed and is addressed by this invention.

SUMMARY OF THE INVENTION

The invention provides a protein labeling and detection system based on self-complementing fragments of fluorescent and chromophoric proteins. The system of the invention is exemplified with various combinations of self-complementing fragments derived from *Aequorea victoria* Green Fluorescent Protein (GFP), which are used to detect and quantify protein solubility in multiple assay formats, both in vitro and in vivo.

In one particular embodiment, test proteins are fused to a sixteen amino acid fragment of GFP (β-strand 11, amino acids 215-230), engineered to not perturb fusion protein solubility. When the complementary GFP fragment (β-strands 1 through 10, amino acids 1-214) is added, spontaneous association of the GFP fragments results in structural complementation, folding, and concomitant GFP fluorescence.

The split-GFP system is very simple, requires no external reagents, provides a sensitive analytical signal directly proportional to the amount of tagged protein, quantifies amounts of proteins typically encountered at the bench in less than 15 minutes, can report either soluble or insoluble protein, and works both in vivo and in vitro. No other existing protein tagging and detection system combines these capabilities. As detailed in the Examples, infra, the split-GFP system has been used to quantify proteins in multiwell plates, and to monitor protein expression and solubility in living *Escherichia coli* cells.

The split GFP system of the invention will be particularly useful for assaying protein solubility, for quantifying protein, and as reporter assays for monitoring the success of directed evolution strategies aimed at improving the folding and solubility of a particular polypeptide or protein. Additionally, the systems of the invention may be used to assay for factors that inhibit and/or promote improper folding of proteins, specifically in high thoughput drug development formats.

Methods for generating self-complementing fragments of a reporter protein are also provided. These methods are exemplified by the generation of engineered fragments of GFP, and may be used to create self-complementing fragments of other GFP-like fluorescent and non-fluorescent proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
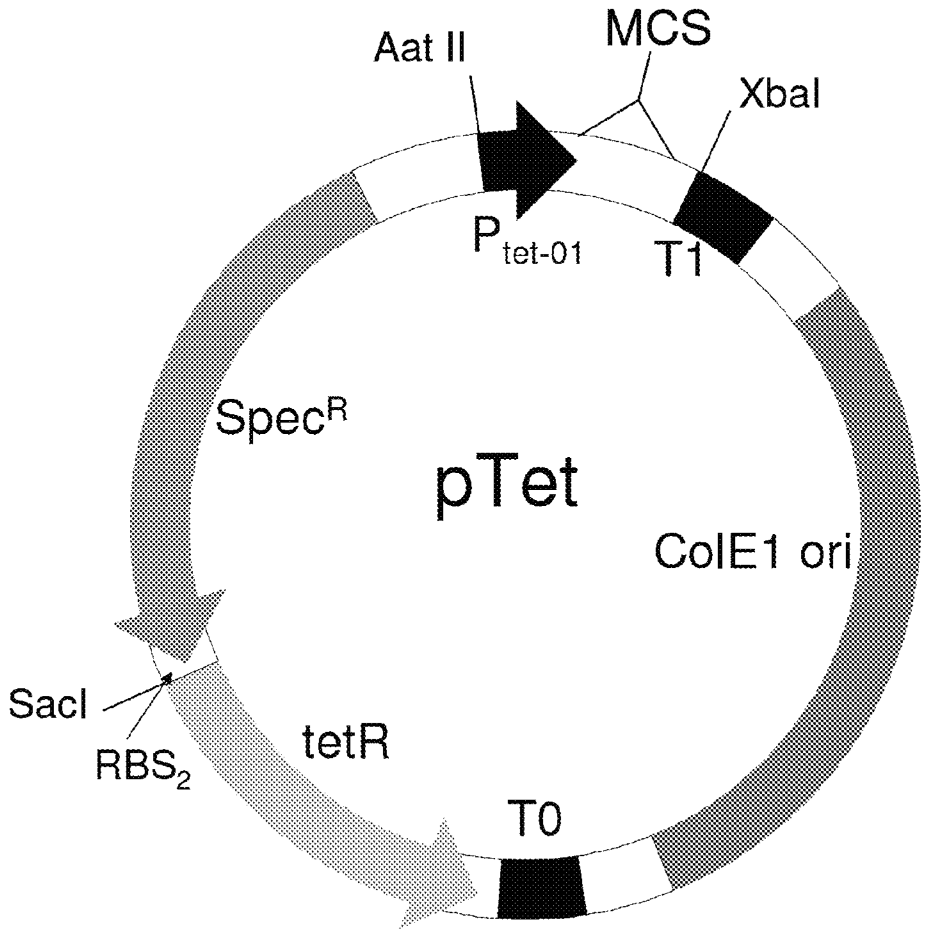
FIG. 1A shows a schematic diagram of the pTET-SpecR plasmid, which is a modified version of the pPROTet.6×HN vector available from Clontech (Palo Alto, Calif.). The chloramphenicol resistance gene was replaced by the spectinomycin resistance marker under the control of the kanamycin promoter of the pPROlar resistance marker (pPROlar plasmid from Clontech, Palo Alto, Calif.). On the same cistron is encoded the tetracycline repressor upstream of the T0 transcription termination sequence. The amount of translated repressor is regulated by a weak Shine-Delgarno sequence downstream of SacI.

FIG. 1 B shows the different elements of the engineered pTET-SpecR plasmid. [SEQ ID NO: 22] Sequence in bold=v1 cloning cassette for expressing genes under tet promoter, flanked by NcoI CCATGG, and KpnI GGTACC. Grey=T0 transcription terminator for the SpecR-tetR cistron; Green=tetR repressor gene; Yellow=RBS controlling tetR translation; Magenta=spectinomycin (specR) gene; Cyan=kanamycin promoter element from PROLAR vector (Clontech, Palo Alto, Calif.).

Figure 2:
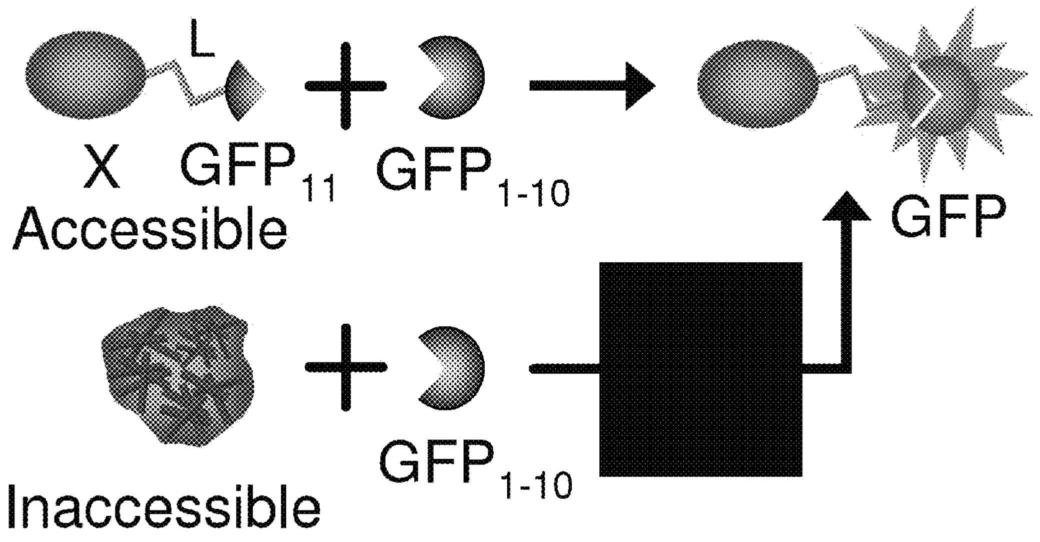

FIG. 2 shows principle of split GFP complementation. A protein of interest (X) is fused to a small GFP fragment (β-strand 11, residues 215-230) via a flexible linker (L). The complementary GFP fragment (β-strands 1-10, residues 1-214) is expressed separately. Neither fragment alone is fluorescent. When mixed, the small and large GFP fragments spontaneously associate, resulting in GFP folding and formation of the fluorophore. Processes that make the small GFP tag inaccessible, such as misfolding or aggregation, can prevent complementation.

Figure 3:
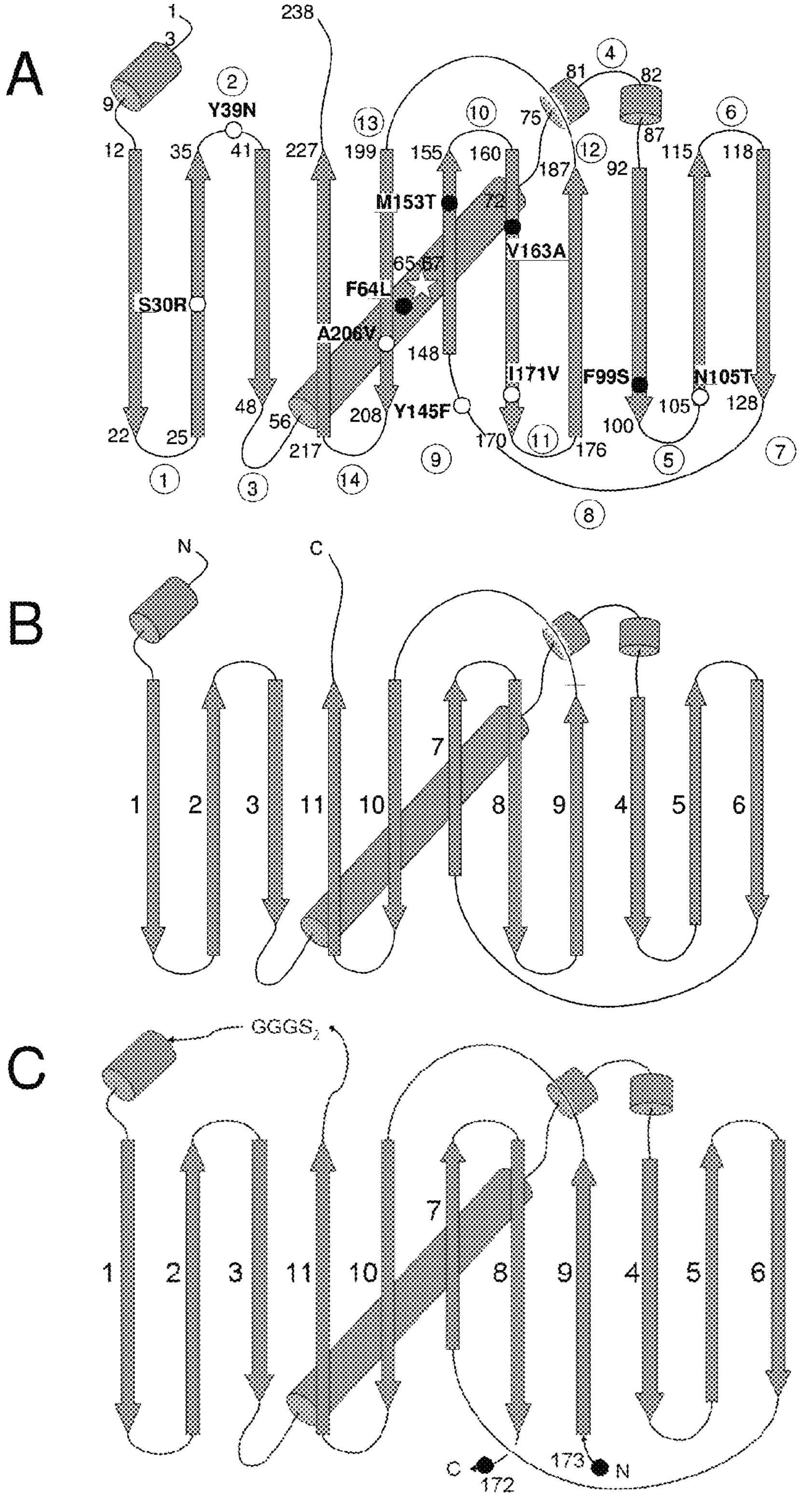

FIG. 3 shows the topological secondary structure diagram of the eleven beta-stranded GFP family members. (A) Strands and numbering of amino acids. Circled number corresponds to index of the turn between strands (and a preferred site for splitting the protein), dark circles are the folding reporter mutations, and white circles are the superfolder GFP mutations. (B) shows numbering convention of the eleven beta strands. (C) shows a circular permutant GFP made by connecting the N and C termini by a short flexible linker and providing a new start codon at amino acid 173, and stop codon after amino acid 172.

Figure 4:
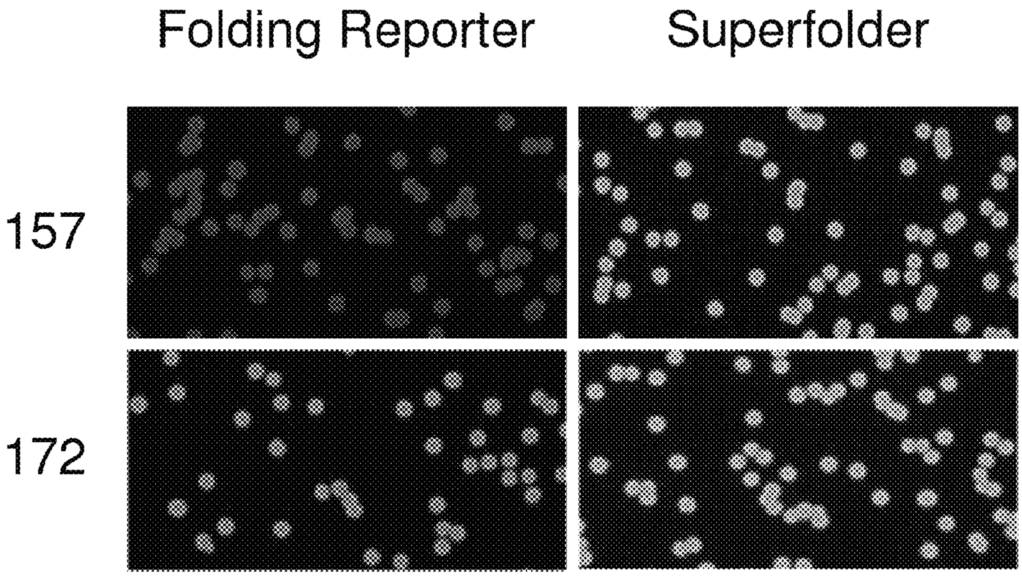

FIG. 4 shows fluorescence images of in vivo complementation by indicated GFP fragments at split position 157 or 172, (i.e. 1-156+157-238 and 1-171 +172-238), co-expressed from compatible plasmids in *E. coli* colonies on plates. Left column shows fragments derived from folding reporter GFP, right column shows same fragments derived from superfolder GFP. As expected, the superfolder fragments work betted and give brighter clones, consistent with the improved folding of superfolder GFP vs. folding reporter GFP.

Figure 5:
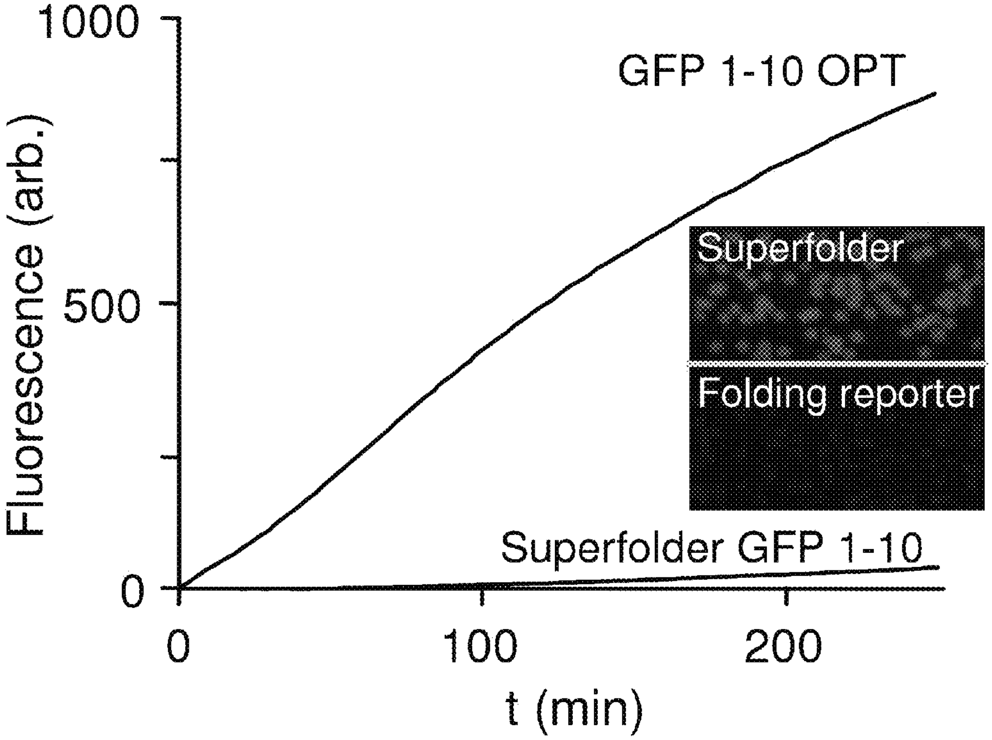

FIG. 5 shows in vitro complementation efficiency of GFP 1-10 variants. Fluorescence progress curves for complementation of 20 μl of 1 mg/ml refolded superfolder GFP 1-10 (lower trace) or an equal amount of soluble optimized GFP 1-10 OPT fragment (upper trace) after addition of 180 μl buffer containing 1 mg/ml soluble sulfite reductase fused to wild type GFP 11. Inset shows in vivo complementation of GFP 1-10 variants. Fluorescent images of *E. coli* BL21(DE3) colonies on nitrocellulose membranes co-expressing GFP 1-10 from superfolder GFP (top), or folding reporter GFP (bottom), along with sulfite reductase fused with wild type GFP S11.

Figure 6:
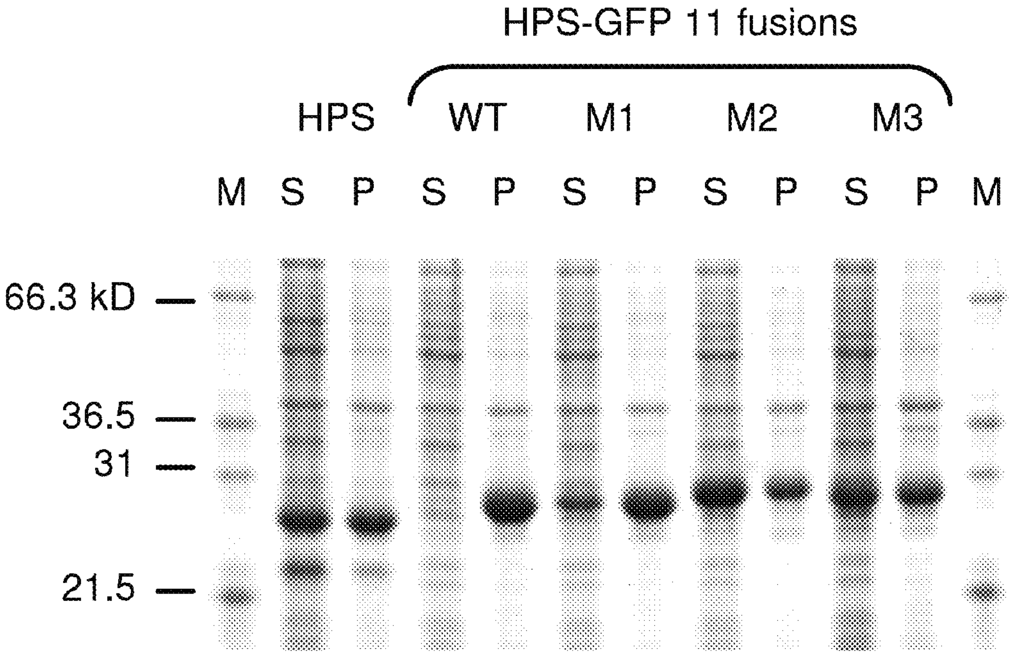

FIG. 6 shows SDS-PAGE gel of soluble (S) and pellet fractions (P) of *E. coli* BL21(DE3) cells expressing the protein hexulose phosphate synthase (HPS) alone or as N-terminal fusions to GFP S11 wild type (WT), or HPS fused to the three GFP S11 optima (M1, M2, M3). Note that the HPS-GFP S11 wild type fusion is insoluble, while HPS alone is ca. 60% soluble.

Figure 7:
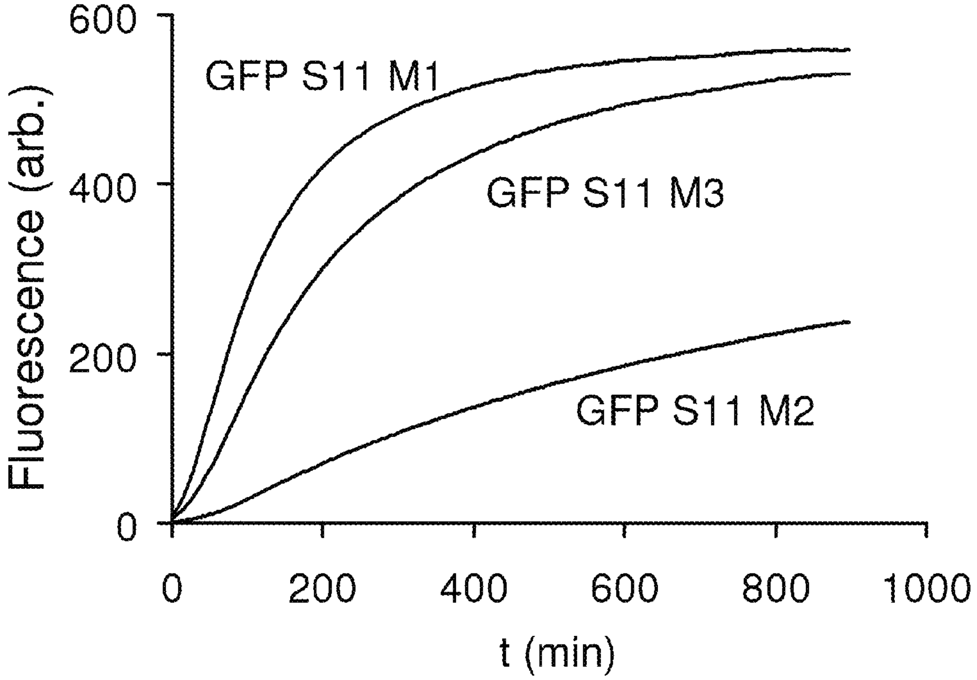

FIG. 7 shows fluorescence complementation kinetic traces for the three GFP S11 mutants M1, M2, and M3 fused to sulfite reductase (50 pmol) after the addition of excess GFP 1-10 OPT (800 pmol) in vitro in tissue culture plates. The final volume of each assay was 200 μl.

Figure 8:
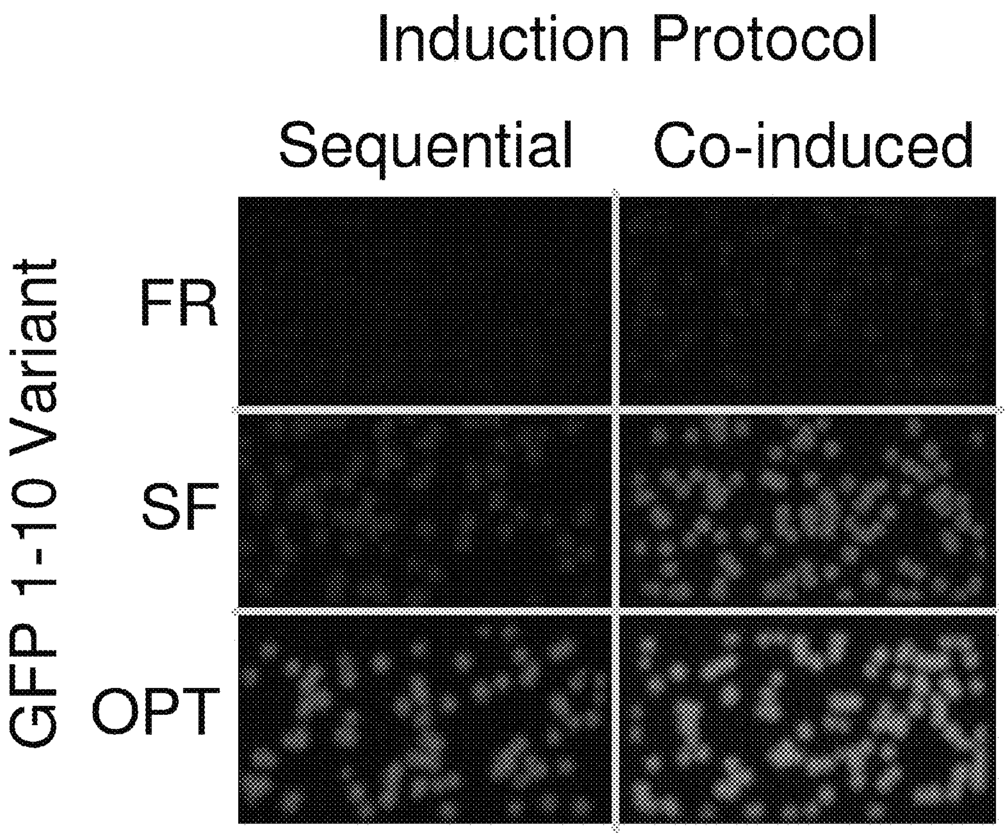

FIG. 8 shows effect of sequential (left column) or co-induction protocols (right column) using three different GFP 1-10 constructs. Fluorescence images of three rows of *E. coli* clones expressing GFP 1-10 constructs with progressively better performance and solubility: folding reporter (FR, first row), superfolder (SF, second row), or the optimized GFP 1-10 variant (OPT, third row). Superfolder GFP 1-10 is insoluble when expressed alone. First column: transient expression of GFP 1-10 followed by expression of sulfite reductase-GFP S11 fusion. Second column: co-expression of GFP 1-10 along with sulfite reductase-GFP S11 wild type. Superfolder GFP 1-10 is insoluble, and cells are faintly fluorescent following the transient induction protocol, likely because the superfolder GFP 1-10 can aggregate prior to the expression of the sulfite reductase-GFP S11 wild type fusion, reducing complementation efficiency. Co-expression gives bright cells likely because binding and complementation between the superfolder GFP 1-10 and sulfite reductase-GFP S11 can occur rapidly, rescuing GFP 1-10 from misfolding and aggregation. In contrast, cells expressing the partially soluble GFP 1-10 OPT are bright whether the constructs are sequentially expressed or co-expressed.

Figure 9:
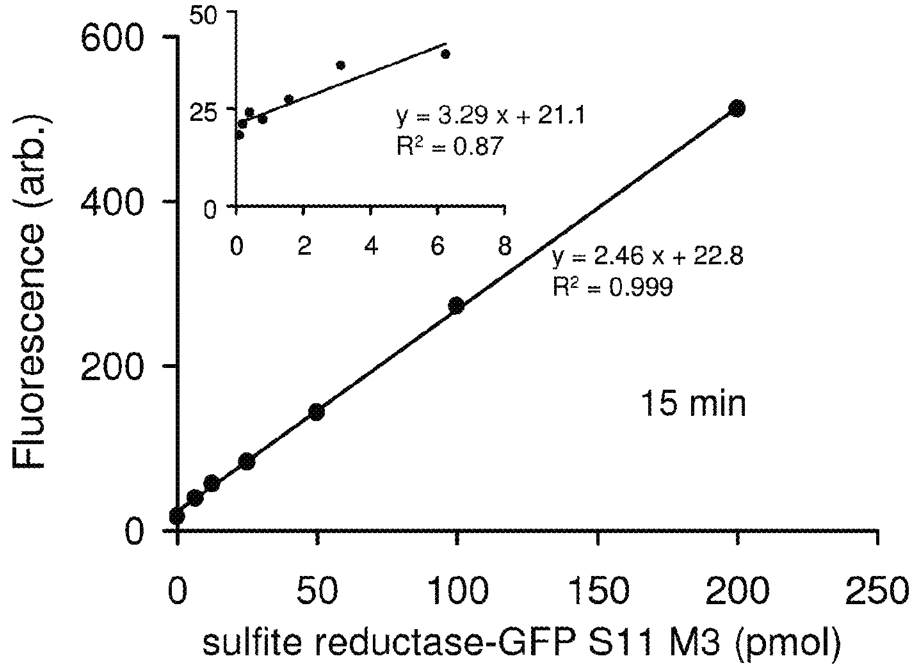
Figure 9:
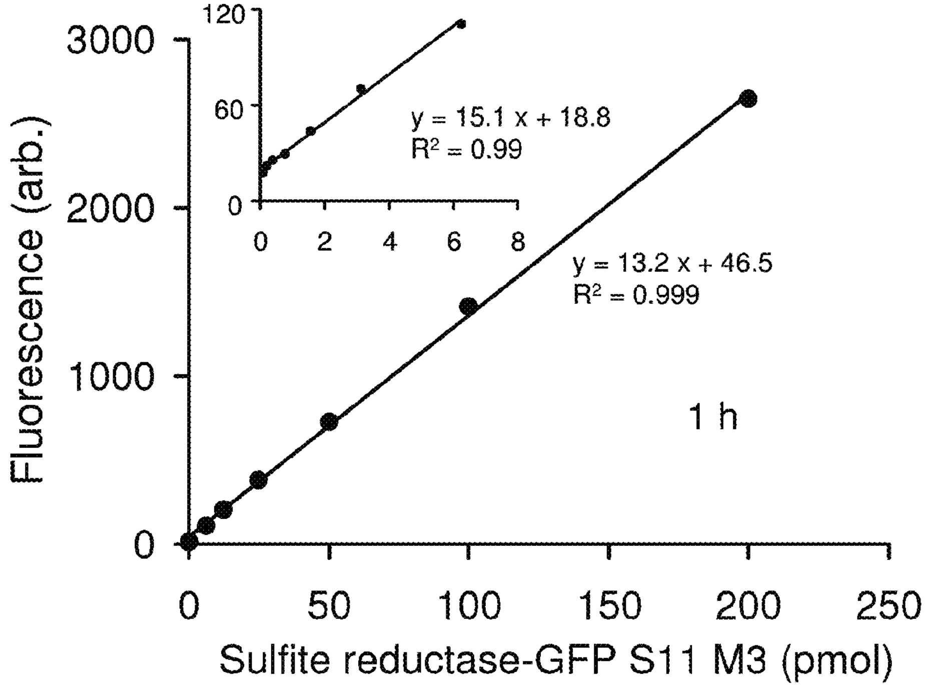

FIG. 9 shows sensitivity of split GFP complementation using GFP S11 M3 tag fragment and GFP 1-10 OPT assay fragment. 20 μl aliquots containing 0.1 to 200 pmol of sulfite reductase-GFP S11 M3 fusion protein were mixed with 180 μl aliquots containing 800 pmol GFP 1-10 OPT to start complementation. (A) Fluorescence measured for each solution 15 min after addition of GFP 1-10 OPT. (B) Fluorescence measured for each solution 1 h after addition of GFP 1-10 OPT.

Figure 10:
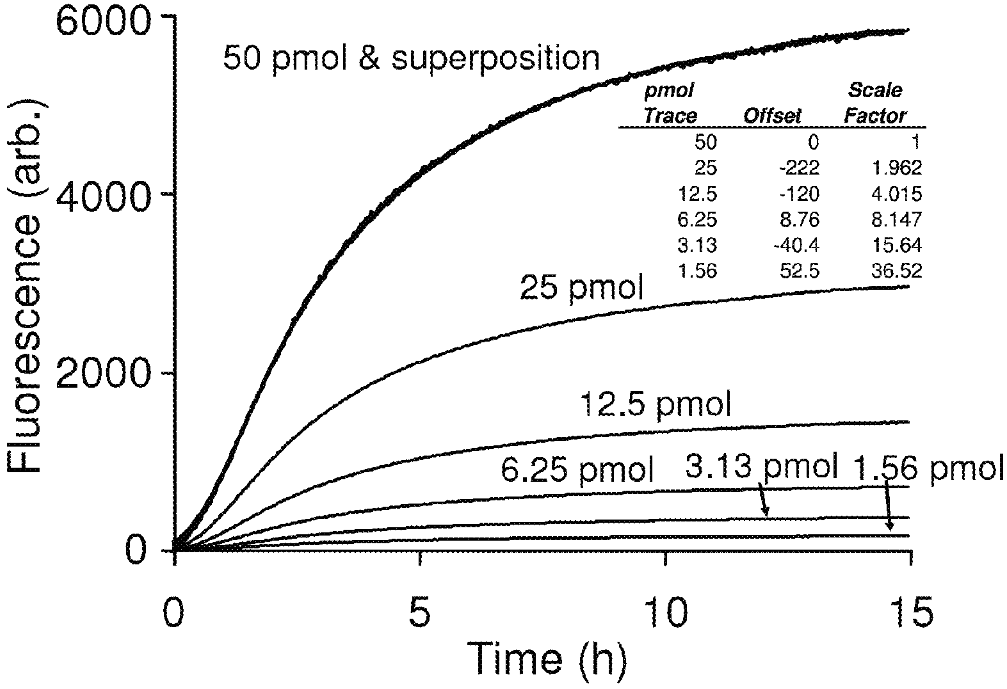

FIG. 10 shows progress curves for complementation of 50, 25, 12.5, 6.25, 3.13, and 1.56 pmol samples of sulfite reductase fused to GFP S11 M3. The data were fit to the 50 pmol progress curve by subtracting a small constant and applying a scaling factor (see inset table in FIG. 10), calculated by non-linear least-squares using the EXCEL data analysis tool Solver (Microsoft, Inc.). The excellent superposition indicates that the shape of the progress curve does not depend on the concentration of the tagged protein, or depletion of the pool of unbound GFP 1-10 OPT fragment.

Figure 11:
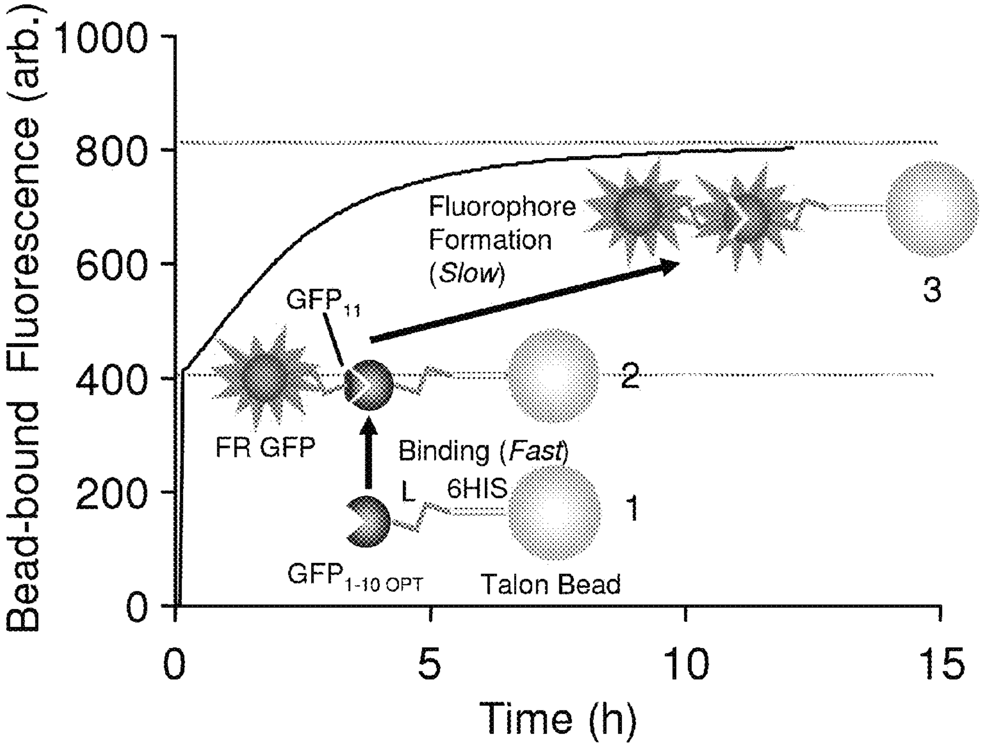

FIG. 11 shows binding to and complementation of TALON® resin-bound 6HIS GFP 1-10 OPT by folding reporter GFP tagged with C-terminal GFP S11 M3. (1) TALON® resin with bound 6HIS GFP 1-10 OPT, (2) rapid increase in bead-bound fluorescence by binding of folding reporter GFP via fused C-terminal GFP S11 M3, (3) slow fluorescence formation due to complementation.

Figure 12:
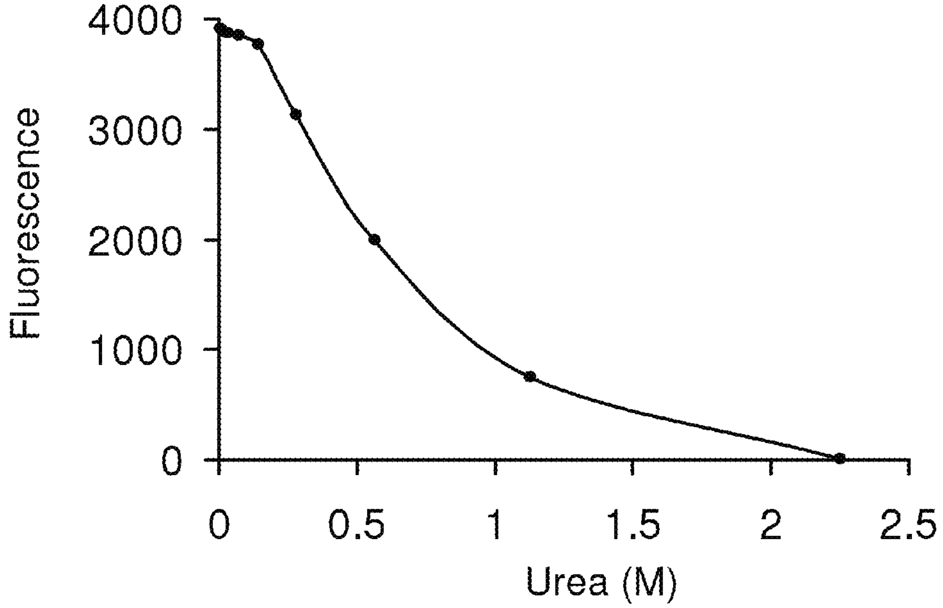

FIG. 12 shows effect of urea concentration on the complementation reaction. Reaction is quenched above 2 M urea.

Figure 13:
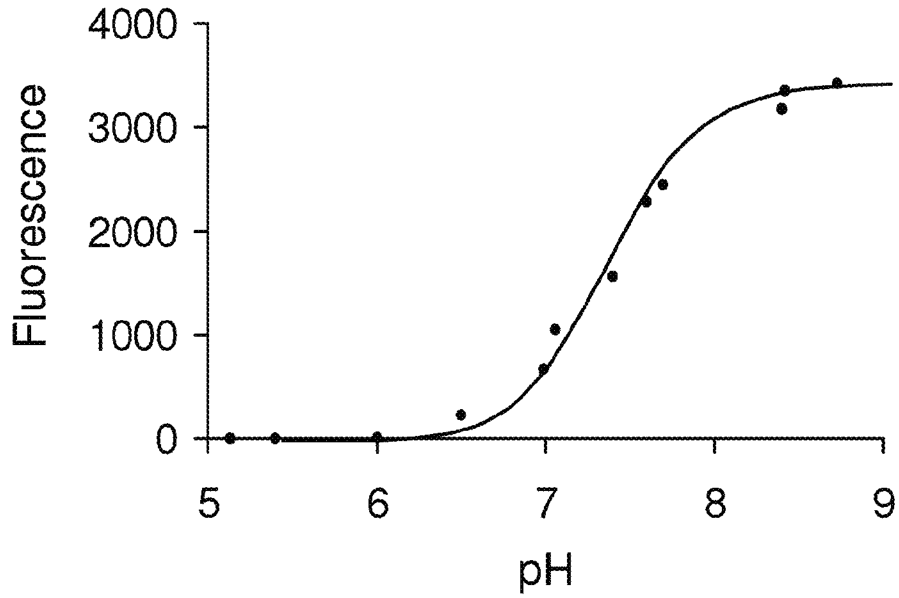
Figure 13:
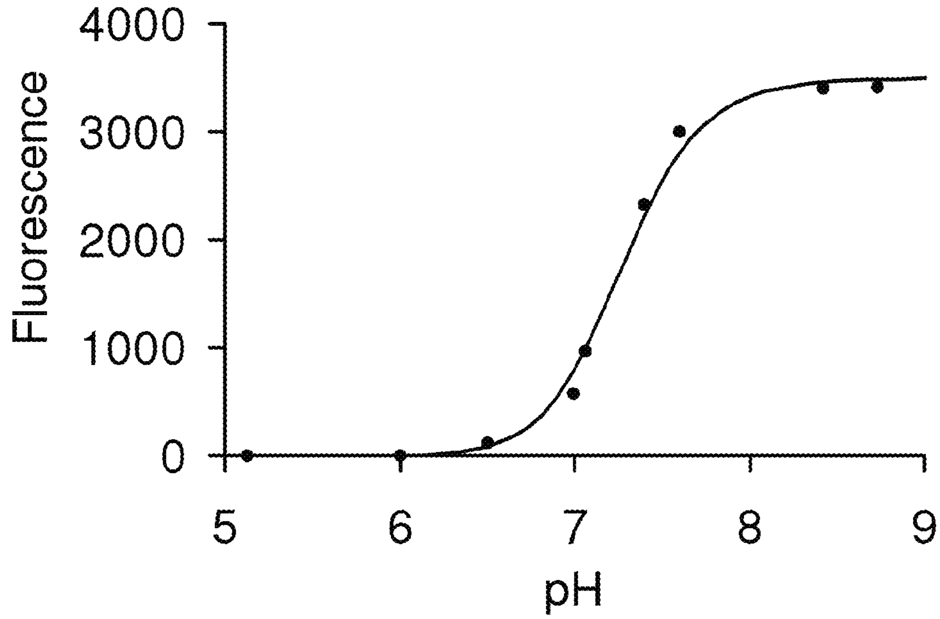

FIG. 13 shows effect of pH on the complementation reaction. (A) pH dependence of final fluorescence for sulfite reductase-GFP S11 M3 6 h after addition of GFP 1-10 OPT. (B) pH dependence of final fluorescence for synthetic peptide GFP S11 6 h after addition of GFP 1-10 OPT. Fluorescence complementation appears inefficient below pH 6.5.

Figure 14:
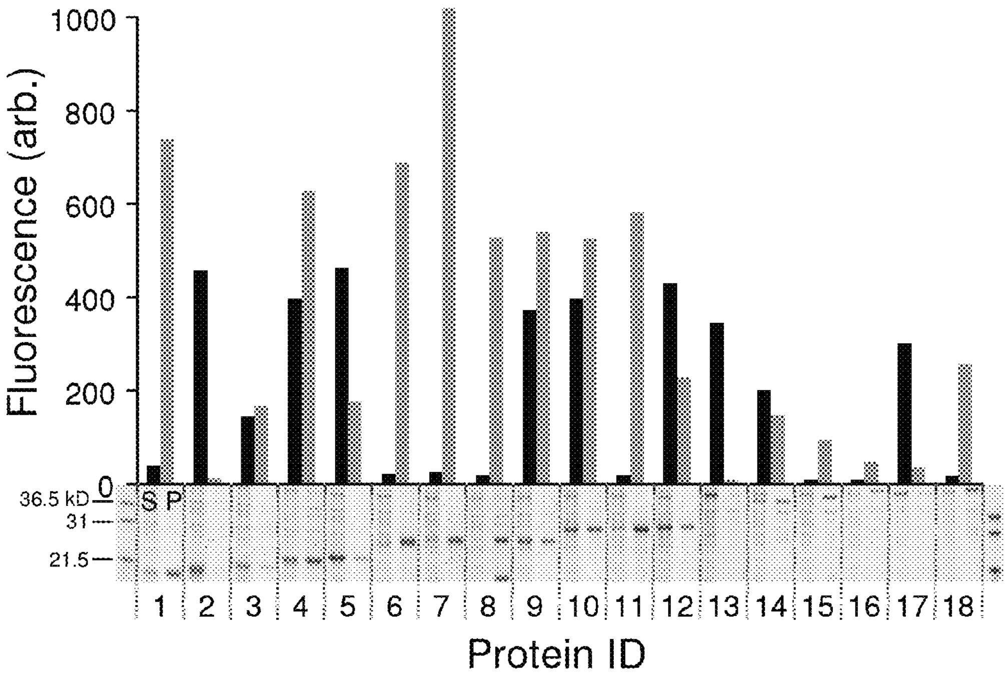

FIG. 14 bar graph shows in vitro protein quantification of eighteen *Pyrobaculum* test proteins (see supra, Table 3) with C-terminal GFP S11 M3 tags, using the split GFP system. The GFP fragment complementation assay fluorescence of soluble (black bars) and unfolded pellet fractions (grey bars) using GFP 1-10 OPT. SDS-PAGE gel shows the corresponding soluble (S), and pellet fractions (P). Note that protein #8, tartrate dehydratase β-subunit, shows a second lower band at ca. 13 kD.

Figure 15:
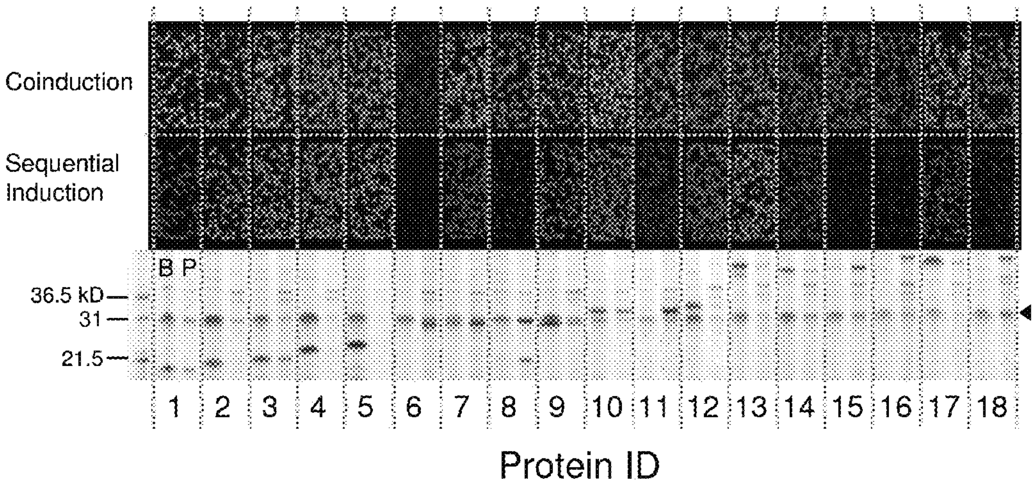

FIG. 15 shows in vivo solubility and expression screen using split GFP assay system. Eighteen *Pyrobaculum* test proteins (see Table 3, supra) expressed with an N-terminal 6HIS tag and a C-terminal GFP S11 M3 tag from a tet-promoter plasmid, were cloned into an *E. coli* BL21 (DE3) strain containing a pET plasmid expressing GFP 1-10 OPT. Fluorescence images of colonies on plates after co-induction of the tagged constructs and GFP 1-10 OPT (top), or transient expression of the tagged constructs followed by expression of the GFP 1-10 OPT (Sequential Induction, middle). SDS-PAGE of TALON® resin bead-bound soluble (B) and pellet fractions (P) from cells sequentially induced in liquid culture (bottom). Adventitiously-bound GFP 1-10 OPT (apparent molecular weight ca. 29 kD) is indicated by arrow. Note that nucleoside diphosphate kinase (protein #7) is partially soluble (see band slightly below band corresponding to GFP 1-10 OPT in TALON® resin-bound fraction). Polysulfide reductase-GFP S11 M3 fusions (see Table 3, supra) produced intensely red-colored colonies, absorbing the 488 nm excitation light and reducing whole-cell fluorescence during co-expression despite the good expression of the protein.

Figure 16:
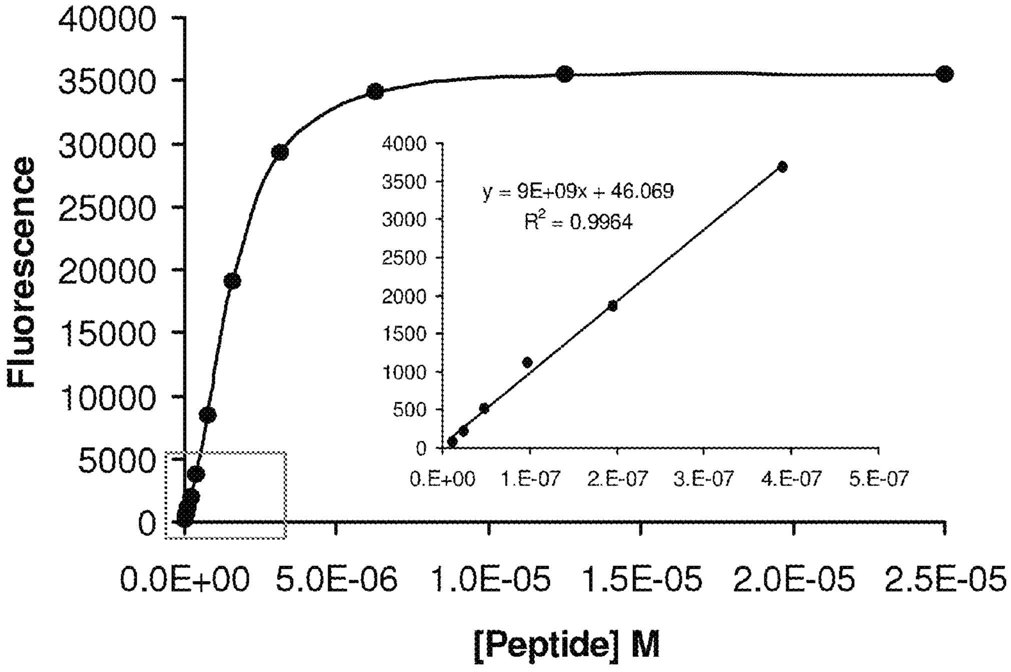

FIG. 16 shows the shows sensitivity of split GFP complementation using GFP S10-11 OPT tag fragment and GFP 1-9 OPT assay fragment. 20 μl aliquots containing sulfite reductase-GFP S10-11 OPT fusion protein were mixed with 180 μl aliquots containing 250 μM GFP 1-9 OPT to start complementation. Fluorescence measured for each solution 6 h after addition of GFP 1-10 OPT. Since the concentration of GFP 1-9 OPT is limiting, the fluorescence plateaus above ca. 250 μM sulfite reductase-GFP S10-11.

Figure 17:
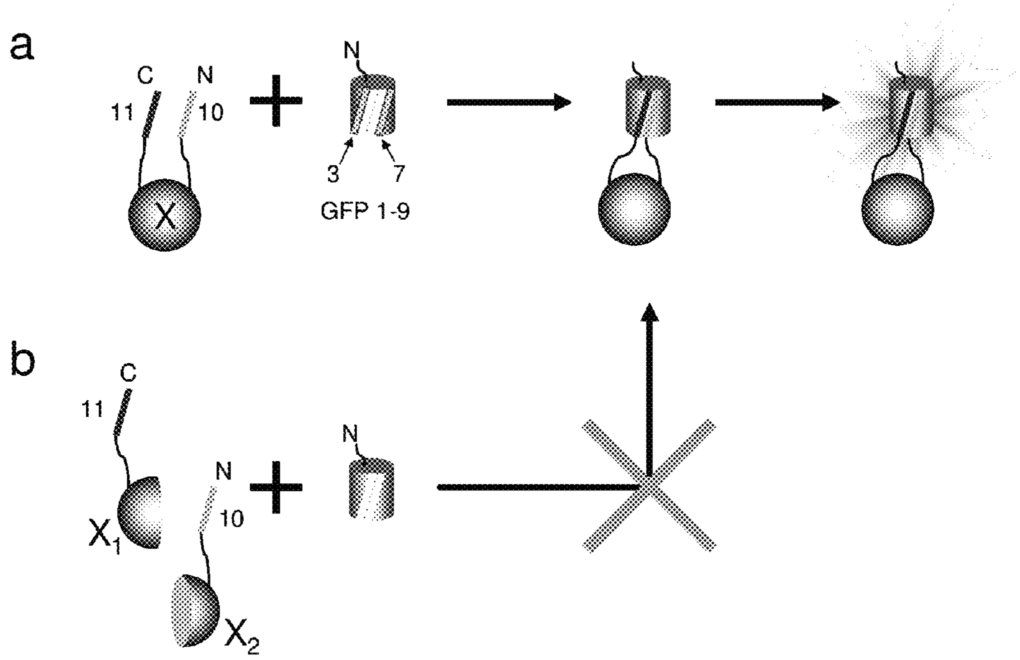

FIG. 17 shows the principle of a sandwich tag format in which a test protein X is expressed as a fusion between two domains of GFP (strand 10 and strand 11) and detected by a third domain of GFP (GFP 1-90PT). (a) complementation occurs efficiently when the tag strands are both linked by an intact target protein X. (b) complementation would be inefficient if the tag strands are separated.

FIG. 18(A) shows the sequences of six optima from evolution of (GFP S10)-L1-NdeI:GGGSGSGG::BamHI-L2-(GFP S11) using GFP 1-9 OPT as complementation target, followed by the starting sequence (bottom sequence). GFP S10 and GFP S11 are shown underlined and in blue highlight. Mutations in the six optima relative to the starting sequence are shown in yellow highlight. Fifth optimum is preferred, and called (GFP S10 SM5)-L1-Nde-1::X::BamH1-L2-(GFP S11 SM5), where X is the target protein of interest. Sequences shown in the figure are, from top to bottom, SEQ ID NO: 50, SEQ ID NO: 51, SEQ ID NO: 52, SEQ ID NO: 53, SEQ ID NO: 50, SEQ ID NO: 54, SEQ ID NO: 49.(B) shows the fourteen mutagenic degenerate primers used to introduce mutations at the target sites of GFP S10. Sequences shown in the figure are, from top to bottom SEQ ID NOs: 55-72.

FIG. 19 shows the reference sequence (GFP S10)-L1-NdeI:GGGSGSGG::BamHI-L2-(GFP S11), the optimum sequence from FIG. 18 A (GFP S10 SM5)-L1-Nde-1::X::BamH1-L2-(GFP S11 SM5), and the sequences of eight optima (GFP S10)-L1-Nde-1::HPS::BamH1-L2-(GFP S11 SM5). Mutations in the target strand GFP S10 which improve the solubility of the starting sequence (GFP S10 SM5)-L1-Nde-1::HPS::BamH1-L2-(GFP S11 SM5) are shown in red highlight. Each of the eight optima sequences continue through the HPS coding sequence and resume with the BamHI site, followed by the flexible linker sequence and GFP S11 SM5 (see the end of the second sequence in list). Sequences shown in the figure are, from top to bottom, SEQ ID NO: 49, SEQ ID NO: 50 and SEQ ID NOs: 73-80.

Figure 20:
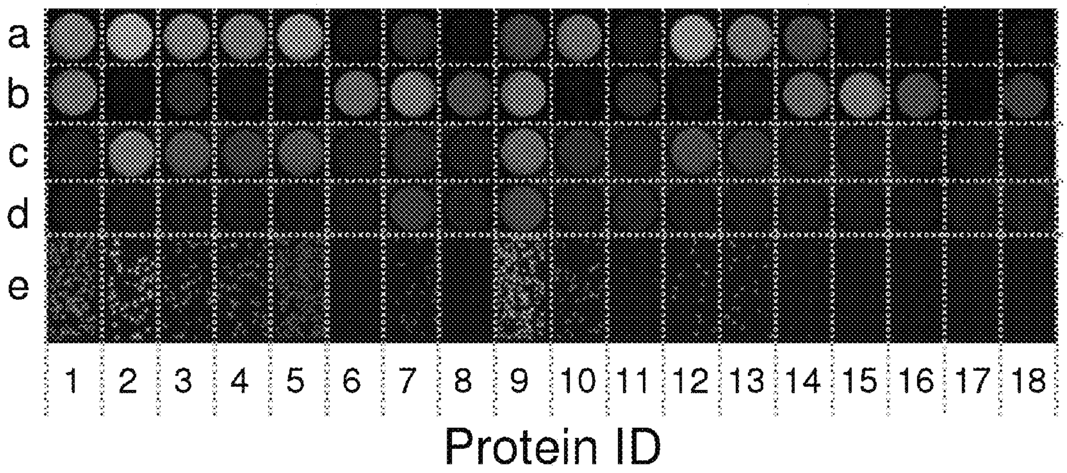

FIG. 20 shows in vitro and in vivo complementation assays of eighteen *Pyrobaculum* control proteins X cloned into the NdeI/BamHI cloning site of a pTET vector with (GFP S10 A10)-GGGS-NdeI-X-BamHI-GGGS-(GFP S11 SM5), and transformed into a BL21(DE3) strain containing GFP 1-9 OPT on a pET 28 vector with a p15 origin. For in vitro assay, liquid cultures were induced only with AnTET. (a) 20 μl soluble aliquot assayed with GFP 1-10 OPT (b) 10 μl urea-solubilized pellet aliquot assayed with GFP 1-10 OPT (c) 20 μl soluble aliquot assayed with GFP 1-9 OPT (d) 10 μl urea-solubilized pellet aliquot assayed with GFP 1-9 OPT. (e) Fluorescent images of *E. coli* after transient induction of sandwich tag construct from pTET using AnTET reagent, then induction of GFP 1-9 using IPTG.

Figure 21:
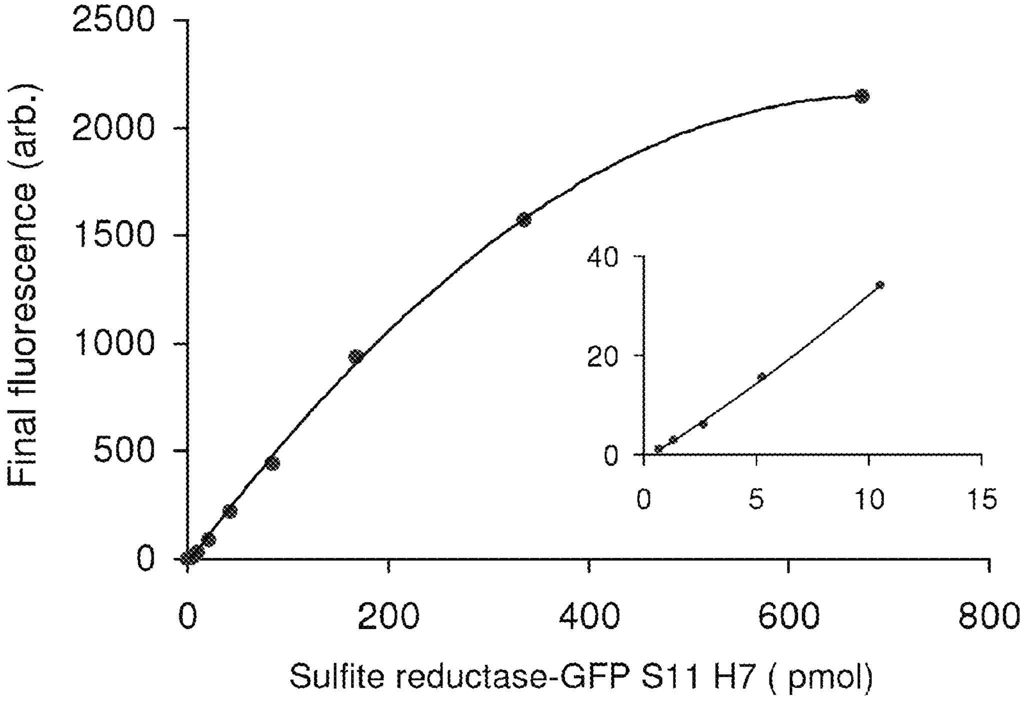

FIG. 21 shows the sensitivity profile of soluble sulfite reductase-S11 H7 fusion complemented with GFP 1-10 A4. The assay shows picomole sensitivity. In this experiment, the 96-well microplate was not blocked with a solution of 0.5% bovine serum albumin (BSA). The non linearity of the calibration curve at low concentrations (inset) is likely due to losses of the tagged protein by adsorption on the surface of the well.

Figure 22:
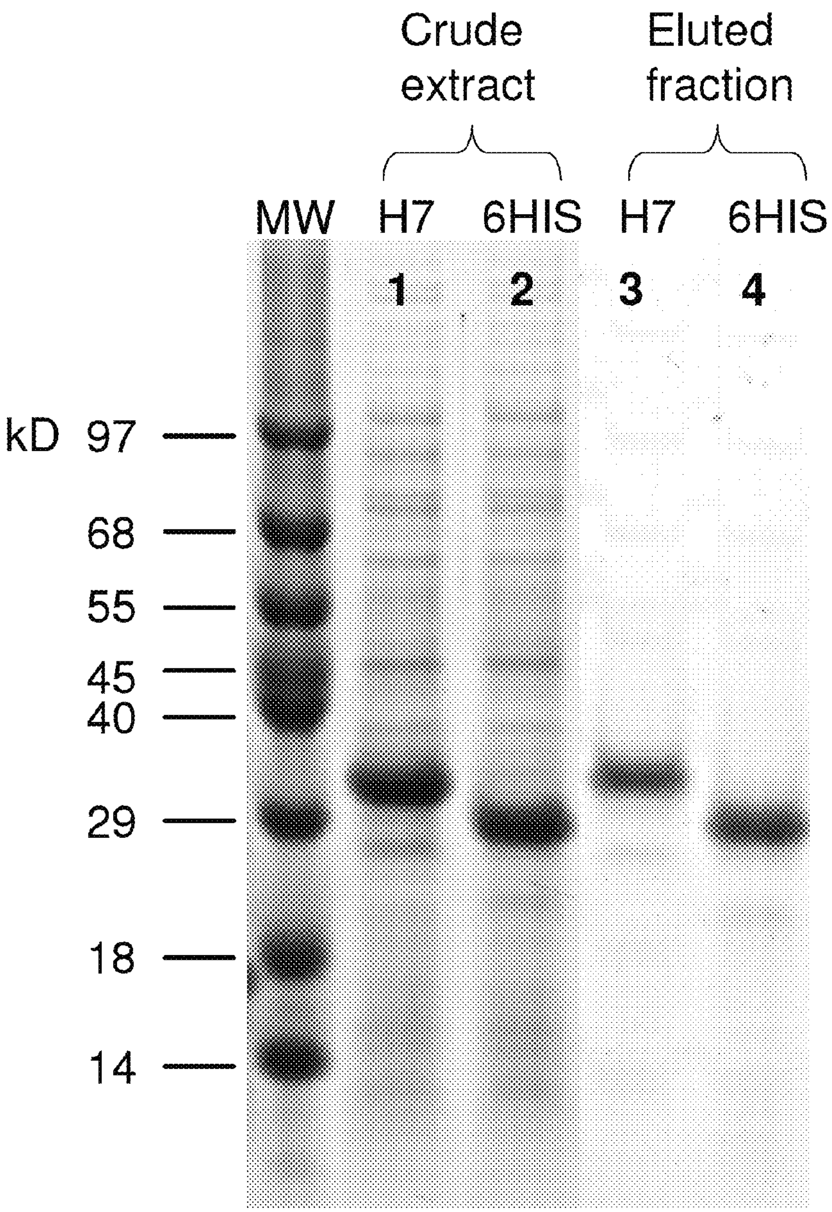

FIG. 22 shows the image of the stained SDS-PAGE gel of crude extract and purified fractions for folding reporter GFP-(GFP-S11 H7) fusion, and for N6HIS-folding reporter GFP fusion.

Figure 23:
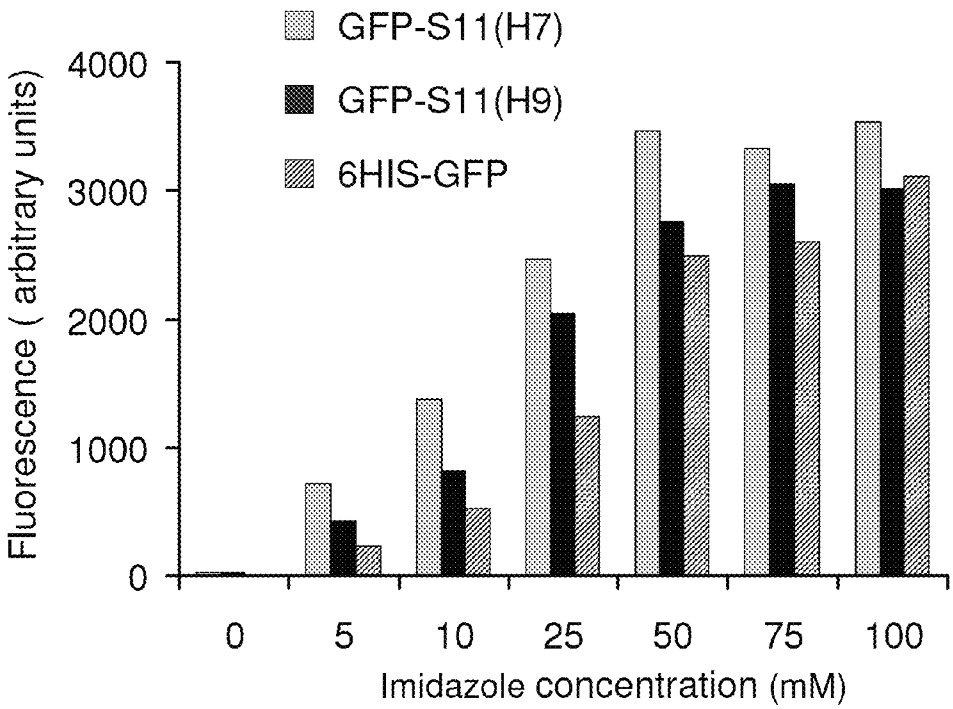

FIG. 23 is a bar graph showing the fluorescence of eluted fractions at different imidazole concentrations, for N6-HIS-GFP, folding reporter GFP-(GFP S11 H7) and folding reporter GFP-(GFP S11 H9) bound to TALON® resin beads. The (GFP S11 H7) tag begins to elute at lower concentrations of imidazole, relative to the more tightly-bound (GFP S11 H9). Since the signal corresponds to the amount of protein released to the supernatant, the brighter the signal, the less tightly-bound the species is at the indicated imidazole concentration.

Figure 24:
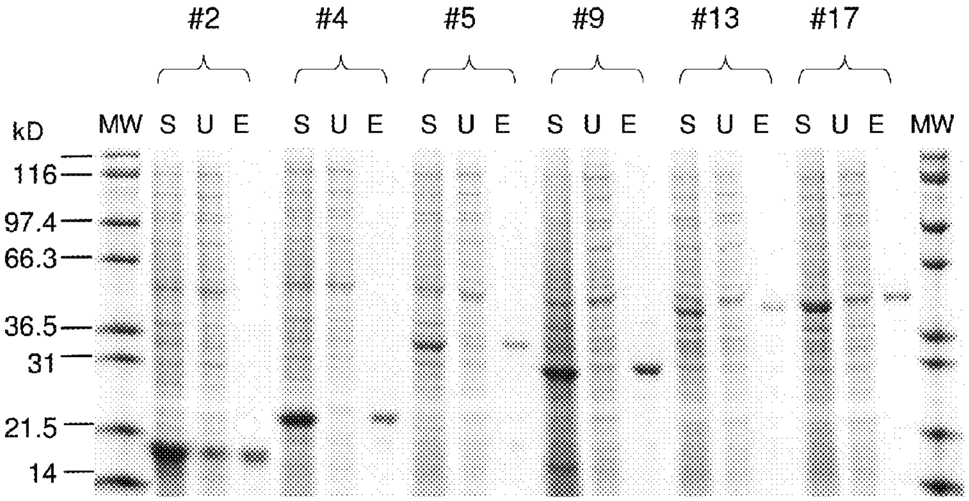

FIG. 24 shows small scale purification of several test proteins from *Pyrobaculum* with C-terminal (GFP S11 H9) tags using TALON® resin. SDS-PAGE of (S) soluble lysate, (U) unbound fraction, (E) eluted protein using 150 mM imidazole in TNG buffer.

SEQUENCES

The Sequence Listing is submitted as an ASCII text file called "87303_01_ST25.txt, " created on May 9, 2013, ~52 KB, which is incorporated by reference herein.

DETAILED DESCRIPTION OF THE INVENTION

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

A "fluorescent protein" as used herein is an *Aequorea victoria* green fluorescent protein (GFP), structural variants of GFP (i.e., circular permutants, monomeric versions), folding variants of GFP (i.e., more soluble versions, superfolder versions), spectral variants of GFP (i.e., YFP, CFP), and GFP-like fluorescent proteins (i.e., DsRed). The term "GFP-like fluorescent protein" is used to refer to members of the *Anthozoa* fluorescent proteins sharing the 11-beta strand "barrel" structure of GFP, as well as structural, folding and spectral variants thereof. The terms "GFP-like non-fluorescent protein" and "GFP-like chromophoric protein" (or, simply, "chromophoric protein" or "chromoprotein") are used to refer to the *Anthozoa* and *Hydrozoa* chromophoric proteins sharing the 11-beta strand "barrel" structure of GFP, as well as structural, folding and spectral variants thereof. GFP-like proteins all share common structural and functional characteristics, including without limitation, the capacity to form internal chromophores without requiring accessory co-factors, external enzymatic catalysis or substrates, other than molecular oxygen.

A "variant" of a fluorescent protein is derived from a "parent" fluorescent protein and retains the 11 beta-strand barrel structure as well as intrinsic fluorescence, and is meant to include structures with amino acid substitutions, deletions or insertions that may impart new or modified biological properties to the protein (i.e., greater stability, improved solubility, improved folding, shifts in emission or excitation spectra, reduced or eliminated capacity to form multimers, etc) as well as structures having modified N and C termini (i.e., circular permutants).

The term "complementing fragments" or "complementary fragments" when used in reference to a reporter polypeptide refer to fragments of a polypeptide that are individually inactive (i.e., do not express the reporter phenotype), wherein binding of the complementing fragments restores reporter activity. The terms "self-complementing", "self-assembling", and "spontaneously-associating", when used to describe two or more fluorescent (or chromophoric) protein fragments, mean that the fragments are capable of reconstituting into an intact, fluorescent (or chromophoric) protein when the individual fragments are soluble. The "MMDB Id: 5742 structure" as used herein refers to the GFP structure disclosed by Ormo & Remington, MMDB Id: 5742, in the Molecular Modeling Database (MMDB), PDB Id: 1 EMA PDB Authors: M. Ormo & S. J. Remington PDB Deposition: 1 Aug. 96 PDB Class: Fluorescent Protein PDB Title: Green Fluorescent Protein From *Aequorea Victoria*. The Protein Data Bank (PDB) reference is Id PDB Id: 1 EMA PDB Authors: M. Ormo & S. J. Remington PDB Deposition: 1 Aug. 96 PDB Class: Fluorescent Protein PDB Title: Green Fluorescent Protein From *Aequorea Victoria*. (see, e.g., Ormo et al. "Crystal structure of the *Aequorea victoria* green fluorescent protein." Science 1996 Sep. 6; 273(5280):1392-5; Yang et al, "The molecular structure of green fluorescent protein." *Nat. Biotechnol.* 1996 Oct. 14(10):1246-51).

"Root mean square deviation" ("RMSD") refers to the root mean square superposition residual in Angstroms. This number is calculated after optimal superposition of two structures, as the square root of the mean square distances between equivalent C-alpha-atoms.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively.

BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPS containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "as determined by maximal correspondence" in the context of referring to a reference SEQ ID NO means that a sequence is maximally aligned with the reference SEQ ID NO over the length of the reference sequence using an algorithm such as BLAST set to the default parameters. Such a determination is easily made by one of skill in the art.

The term "link" as used herein refers to a physical linkage as well as linkage that occurs by virtue of co-existence within a biological particle, e.g., phage, bacteria, yeast or other eukaryotic cell.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

"Fused" refers to linkage by covalent bonding.

As used herein, "linker" or "spacer" refers to a molecule or group of molecules that connects two molecules, such as a fluorescent binding ligand and a display protein or nucleic acid, and serves to place the two molecules in a preferred configuration.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell. Probes 8: 91-98). The term nucleic acid is used interchangeably with gene, cDNA, and mRNA encoded by a gene.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "isolated" and "purified" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

Split-Fluorescent and Chromophoric Protein Systems

One aspect of the present invention provides soluble self-complementing fragments of a fluorescent or chromophoric protein. Separately, the fragments do not display the fluorescent or chromophoric "reporter" phenotype. When physically proximate, the fragments spontaneously complement, thereby reconstituting the protein from which they were derived, restoring the reporter phenotype. Complementary sets of such fragments are termed "split-fluorescent" or "split-chromophoric" protein systems. These systems may be generated from GFP, GFP-like fluorescent proteins, GFP-like non-fluorescent proteins, and variants thereof, and are useful for tagging and detecting soluble or insoluble proteins in living cells, in cell lysates, or in other in vitro assay formats. Various other uses of the split-fluorescent and split-chromophoric systems of the invention are envisioned.

The split-fluorescent and split-chromophoric protein systems of the invention are simple to use and require no exogenous reagents for detecting the reporter phenotype. In some embodiments, the fragments do not change the solubility characteristics of the test proteins fused thereto. In other embodiments, a fragment may perturb the solubility of the test proteins fused thereto, and nevertheless be useful as a protein solubility screen.

To illustrate this aspect of the invention, several sets of self-complementing fragments of a solubility-enhanced GFP (U.S. patent application Ser. No. 10/423,688: WO 03/095610) were constructed and employed in a series of protein detection and quantification assays, and in purification methodologies, as further described in Examples 6, 9, 10 infra. These "split-GFP" protein detection systems demonstrate reliable quantification of soluble, insoluble and/or total protein content in vivo and in in vitro (i.e., soluble expressed protein from living cells, in crude lysates, and in any samples during purification and downstream manipulations).

Any of the GFP, GFP-like fluorescent proteins and GFP-like chromophoric proteins may be employed in the practice of the invention (see description of this family of proteins under the subheading FLUORESCENT AND CHROMOPHORIC PROTEINS, infra). Additionally, the concept of the invention may be extended to the generation of other split-reporter protein systems, employing any number of proteins with a detectable phenotype, such as the enzyme beta lactamase, beta galactosidase (Ullmann, Jacob et al. 1967; Welply, Fowler et al. 1981; Worrall and Goss 1989; Jappelli, Luzzago et al. 1992; Rossi, Blakely et al. 2000; Wigley, Stidham et al. 2001; Lopes Ferreira and Alix 2002), dihydrofolate reductase (Gegg, Bowers et al. 1997; Iwakura and Nakamura 1998; Pelletier, Campbell-Valois et al. 1998; Pelletier, Arndt et al. 1999; Iwakura, Nakamura et al. 2000; Smith and Matthews 2001; Arai, Maki et al. 2003), chloramphenicol resistance protein for example.

The split-fluorescent and split-chromophoric protein systems enable a number of protein detection and quantification assays, which assays provide major advantages over conventional techniques for protein detection and quantification, such as SDS-PAGE, dot-blots, and the like, which are time consuming and difficult to robotize. For example, protein detection and quantification using the split-GFP systems of the invention provide a high degree of sensitivity, enabling picomolar protein detection in either living cells or in crude cell lysates (see EXAMPLE 9 and EXAMPLE 10, infra). Additionally, the assay systems are robust (i.e., tolerant to denaturing agents, pH conditions and adjuvants, see Example 8, infra), permitting protein quantification from unfolded pellets, thereby providing a means for quantifying total protein expression, and a means for evaluating soluble protein recoveries in screening for protein refolding reagents.

The design of a split-fluorescent protein system of the invention may be briefly illustrated as follows. As will be appreciated by those skilled in the art, the design of a split-chromophoric protein detection system will involve the same steps and principles. First, the fluorescent protein of interest is structurally analyzed in order to determine appropriate splice points for generating individual fragments. As will be understood by those skilled in the art, this may be accomplished by reference to a known crystal structure of the fluorescent protein, either with or without superpositioning with the GFP crystal structure or another fluorescent protein crystal structure, by primary sequence alignment with GFP, by predictive structural modeling (with reference to a known fluorescent protein structure, i.e., GFP), etc.

Appropriate splice (or "split") points are found within the sequences between beta-sheets, specifically, the loop and turn motifs (see FIG. 3 A, 3 B). In the design of a simple, two-fragment system, a fluorescent protein may be split into two fragments at any point in the molecule between contiguous beta-strands (i.e., within the turn or loop motifs occurring between beta-strands), in order to generate a first fragment corresponding to a first set of contiguous beta-strands, and a second fragment corresponding to a second set of contiguous beta-strands, the total complement of beta-strands being contained within the combination of the two fragments. Thus, for example, one may split the fluorescent protein into fragments corresponding to strands 1-9 and 10-11, or to strands 1-10 and 11. All 11 beta-strands of the fluorescent (or chromophoric) protein are represented in the combination of fragments. It should be noted that circular permutants of a fluorescent protein may also be created, by ligating the native N and C termini and introducing new start and stop codons, and split into fragments corresponding to contiguous beta-strands (for example, into fragments corresponding to pre-permutant strands 9-1 and 2-8) (FIG. 3 C). Exemplary two-fragment split-GFP systems are described in Examples 2, 11, 13, infra.

Similarly, where a three-fragment system is to be generated, the fluorescent protein may be split into fragments corresponding to beta-strands 1-9, 10 and 11, for example. An exemplary three-fragment split-GFP system is described in Example 12, infra.

Once the design of the fragments has been realized, nucleic acid constructs encoding the fragments may be prepared using cloning methods well known in the art (for example, see Example 1 and Example 2, infra).

In an alternative approach, different fragment sets of the same or related fluorescent proteins may be evaluated empirically for complementation. For example, as described in Example 2, several pairs of GFP fragments can be co-expressed on compatible plasmids in *E. coli*, and evaluated for complementation and relative fluorescence. This approach may enable an initial rapid screen for promising fragment sets from a group of fluorescent protein variants (i.e., superfolder GFP and cycle 3 GFP, see Example 2). Subsequently, individual fragments selected from this screen may be evolved to improve solubility and attenuate test protein solubility perturbation (see subheading SPLIT-PROTEIN FRAGMENT ENGINEERING, infra, and Examples 3 and 4, infra).

Protein detection using the split-fluorescent or chromophoric protein systems of the invention follow essentially the principles for all applications. Briefly, one of the fragments (the "tag" fragment) of the fluorescent (or chromophoric) protein is expressed as a fusion with a test protein. If the test protein is soluble, the fusion will be soluble, and thus available for complementation with the other fragment of the reporter protein (the "assay fragment"), which is made available to the test protein-tag fusion protein by, for example, expressing it in the same cell, adding it to a lysate of the cell expressing the fusion protein, etc. In contrast, if the test protein is insoluble, or only partially soluble, the test protein will aggregate, thereby "burying" the fused tag fragment, thus rendering the test protein-tag fusion insoluble and inaccessible for complementation with the assay fragment. If complementation occurs, the detectable reporter phenotype will be activated. For example, where a fluorescent protein is used as the reporter, reconstitution of the characteristic beta-barrel structure following self-complementation of the individually expressed fragments permits the formation of the chromophore, thereby emitting detectable fluorescence. A schematic diagram of how the system works using a split-GFP system is shown in FIG. 2.

Split-fluorescent protein fragments should be capable of being folded and soluble in the environment of the particular assay in which they are to be employed. In preferred embodiments, the folding/solubility of individual fragments is tested, and typically evolved, in order to isolate a soluble "tag" fragment(s) and a soluble "assay" fragment(s). In preferred solubility assay applications, the tag fragment is between 1 and 3 beta-strands, and in most preferred applications, the tag is a single beta-strand. Test proteins are fused to the tag fragment, which preferably is substantially non-perturbing to fused test proteins. In other words, the solubility and folding of the test protein alone should be similar to the solubility and folding of the test protein when fused with the tag.

Based on experimental results using split-GFP systems (see Example 2), optimum performance in solubility assays are achieved by using a relatively large assay fragment (e.g., about 8 to 10 contiguous beta-strands) and a relatively small tag fragment (e.g., about 1 to 3 contiguous beta-strands) to which the test protein is fused, wherein the assay fragment is soluble and available for complementation to the tag fragment-test protein fusion, and wherein the tag fragment is non-perturbing to test protein solubility. Ideally, for most applications, the solubility of the test protein alone, and the solubility of the test protein in fusion with the tag fragment should be approximately the same. The assay fragment is ideally monomeric, and should not spontaneously aggregate or misfold.

Although in many applications, the use of a non-perturbing tag fragment is preferred, a tag fragment may nevertheless be perturbing to the solubility of the test protein and remain useful in solubility screening assays, provided that there is substantial proportionality between fluorescence and solubility (but not necessarily direct proportionality). In some embodiments, it may in fact be desirable to use a perturbing tag fragment or fragments (see description of Sandwich-Format Assays, infra), such as where the aim is to screen for highly soluble proteins. In this case, the use of a perturbing tag fragment may effectively select against all but the most soluble proteins or versions of a protein. Again, the assay fragment in such applications should be soluble, as insoluble versions will not be available for complementation to soluble test protein-tag fragment fusions.

Methods for evolving fluorescent protein fragments for optimal performance are also provided herein, as described in the subsection SPLIT-PROTEIN FRAGMENT ENGINEERING, infra, and as illustrated in Example 3 and Example 4, infra. These methods may be applied similarly to chromophoric proteins, and to any protein having a detectable phenotype, for the generation of split-protein systems having the characteristics herein described for split-fluorescent protein systems.

Various assay formats may be used to detect and quantify proteins using the split-fluorescent and split-chromophoric protein systems of the invention. Several exemplary assays for protein detection and quantification are further described below. In addition, most of these assays have been demonstrated experimentally, as described in the Example sections, infra.

The split-fluorescent and split-chromophoric protein systems of the invention have a variety of applications in protein solubility screening, protein detection and quantification, protein purification, protein folding and aggregation, directed evolution strategies for improving the solubility and yield of proteins, etc. These applications are now briefly described.

Examples of these applications are also found in the Examples sections which follow.

Protein Detection and Quantitation Assays

The split-fluorescent and split-chromophoric protein systems of the invention may be used to detect and quantify proteins in vitro or in vivo, as described below and as illustrated by the Examples, infra. This aspect of the invention provides assays for the detection of soluble or insoluble protein, and assays for the quantification of soluble, insoluble or total protein expression. In detection and quantification assays, the split-fluorescent or split-chromophoric protein systems are used as generally described, supra. Various embodiments of this aspect of the invention, utilizing split-fluorescent systems, are outlined below. However, it is to be understood that parallel embodiments exist for split-chromophoric protein systems.

In vitro Detection Assays

In one embodiment, a rapid in vitro assay for detecting soluble protein is provided, and comprises lysing bacterial (or other) cells expressing a fusion of a first fluorescent protein tag fragment and a test protein X (e.g. X-GFP S11 or GFP S11-X), contacting the lysate with a second complementary fluorescent protein assay fragment, and screening for detectable fluorescence. The presence of detectable fluorescence in the assay provides an indication that the test protein is soluble. This assay system is amenable to high-throughput screening for soluble variants of a protein from a library of variants, and provides rapid identification of those variants that exhibit improved solubility characteristics, permitting rapid discrimination of optima which may be further evolved. The assay may be performed directly from crude lysates of liquid cell cultures, as described in Example 9, infra.

The practice of an in vitro soluble protein detection assay using a two-fragment split-GFP system may be briefly illustrated as follows. A test protein is fused to the N-terminus of a GFP tag fragment (i.e., X-GFP S11) and expressed in *E. coli*, the cells lysed, and an excess amount of a complementary GFP assay fragment (i.e., GFP 1-10) is combined with the lysate or a sample of the lysate. Detectable fluorescence indicates complementation between the assay fragment and the test protein-tag fragment fusion, thus providing an indication that the test protein is soluble. Moreover, where the tag fragment used is substantially non-perturbing to test protein solubility, the intensity of the fluorescent signal obtained is directly proportional to the quantity of soluble test protein. Thus, in this system, the degree of fluorescence provides accurate quantification of the amount of soluble test protein present in the lysate sample (by reference to a calibrated protein quantity curve, see below, and Example 6, infra). Indeed, even where the tag fragment is perturbing to test protein solubility, there is a proportional relationship between the quantity of test protein and intensity of fluorescence. The complete, or substantial, absence of detectable fluorescence indicates that the tag fragment-test protein fusion was not soluble, or was substantially insoluble, and was therefore unable to complement with the soluble large fragment, thereby providing an indication that the test protein itself is not soluble in *E. coli*.

In the split-GFP systems described herein, the solubility of the test protein determines whether the tag GFP fragment component of the fusion is available for association with its complement. Where the test protein is correctly folded and soluble, the fusion will also soluble, and therefore available for complementation with the soluble assay fragment. However, where the test protein is insoluble, it will aggregate, obscuring or burying the tag domain, rendering the fusion insoluble. Generally, test proteins are fused to the N-terminus of the tag fragment (test protein-tag). C-terminal fusions (tag-test protein) may also be employed, but in such applications, the tag fragment is more likely to adversely affect the folding of the test protein. However, in applications where one desires to screen for only highly soluble proteins, the use of a C-terminal fusion (tag-test protein) may select against all but the most highly soluble proteins.

Various three-fragment systems are also envisioned. In one embodiment, GFP is split into three fragments, typically as one larger assay fragment and two smaller tag fragments. The test protein is inserted in-frame between the two tag fragments (i.e., S10-x-S11), and complementation with the assay fragment (in this case, GFP 1-9) reconstitutes GFP fluorescence if the test protein is soluble. Three fragment systems (i.e., S1-9+S10-x-S11 split-GFP system) are further described in the subsection entitled Engineering a (GFP S10)-X-(GFP S11) Sandwich Tag Format and Detection Using Assay Fragment GFP 1-9 OPT, Example 12 infra. These "sandwich" type soluble protein detection assay formats provide advantages in some applications, such as when a library of mutated proteins are to be screened for enhanced soluble protein yields. The sandwich format assures that only those test proteins that are full-length and intact will be detected. Reading-frame shifts or internal ribosome binding sites introduced into the test protein by mutation would not result in a full fused S10-x-S11, and thus complementation would not occur. Thus, the use of this system effectively screens out these aberrant clones in a directed evolution strategies.

In Vivo Protein Detection Assays

In related, in vivo embodiments, cells are engineered to express both (or, all) complementary fragments, one or two of which are fused to the test protein. The fragments may be expressed simultaneously or sequentially, depending upon whether the assay aims to detect (and quantify) total protein expression or only soluble and/or insoluble fractions. Sequential expression of the two fragments is generally preferred; as co-expression may mask otherwise insoluble test proteins (see above). Sequential expression (or addition) of the test protein-tag fragment fusion, followed by expression of the complementary assay fragment, provides time for an insoluble test protein-tag fusion to aggregate and prevent complementation.

More specifically, for example, the coding sequence of a test protein is fused in-frame (5'->3') to a soluble first tag fragment of a self-complementing pair of fragments of a reporter protein, and placed under the control of a first independently inducible promoter. The coding sequence of a soluble second assay fragment of the self-complementing pair of fragments is placed under the control of a second independently inducible promoter. The two resulting nucleic acid constructs may be incorporated into the same or different vectors (i.e., one or two plasmids), provided that the promoters remain separately inducible, and host cells are transformed or transfected with the vectors. Cells carrying the constructs(s) are initially cultured under baseline conditions permitting the repression of both of the independently inducible promoters. Cell are then induced to express the test protein-tag fragment fusion for a time sufficient to permit expression of the fusion protein e.g., in *E. coli*, typically about ½ to 3½ hours), followed by a "resting" period (approximately ½ to 1½ hours in *E. coli*) to allow inducing agent to diffuse out of the cells (or, in mammalian cells, by active repression of the promoter, using, for example, anti-sense polynucleotides to shut off the promoter). Cells are then induced to express the assay fragment, typically for about ½ to 4 hours in *E. coli*. An alternative embodiment, for mammalian cells, uses protein transfection to introduce assay fragment proteins after "resting" period or following active repression of the first inducible promoter (see, infra).

Systems of two independently controllable promoters have been described and are well known in the art. See, for example, Lutz and Bujard, 1997, *Independent and tight regulation of transcriptional units in Escherichia coli via the lacR/O, the TetR/O and AraC/I1-I2 regulatory elements*. Nucleic Acids Res. 25(6): 1203-1210).

In one example, a vector in which the promoter is under the repression of the LacIq protein and the arabinose inducer/repressor may be used for expression of the assay fragment (e.g., pPROLAR vector available from Clontech, Palo Alto, Calif.). Repression is relieved by supplying IPTG and arabinose to the growth media, resulting in the expression of the cloned assay fragment. In this system, the araC repressor is supplied by the genetic background of the host *E. coli* cell. For the controlled expression of the test protein-tag fusion construct, a vector in which the construct is under the repression of the tetracycline repressor protein may be used (e.g., pPROTET vector; Clontech). In this system, repression is relieved by supplying anhydrotetracycline to the growth media, resulting in the expression of the test protein-tag fusion construct. The tetR and LacIq repressor proteins may be supplied on a third vector, or may be incorporated into the fragment-carrying vectors (see, Example 1, infra).

In using the above system for sequential expression of the test protein-tag fusion, followed by the assay fragment, the addition of anhydrotetracycline to cells transformed with the above constructs displaces the tet repressor, and expression of the test protein-tag fusion is induced. Cells are then transferred to new plates with fresh media, and the anhydrotetracycline is allowed to diffuse into the media for approximately 1 hour, after which the tet repressor again binds to the promoter, shutting off expression. The separately inducible T7 promoter is then activated by the addition of IPTG, inducing the expression of the assay fragment. Expression of the assay fragment proceeds for a time sufficient to permit self-complementation with a soluble first fragment-test protein fusion. Detection of fluorescence (or color, where using a split-chromophoric protein system) detects soluble test protein-tag fusion. See Example 4, infra.

The in vivo solubility assays are amenable to high-throughput screens, as a large number of cells expressing variants of a test protein, fused to the tag fragment, can be assayed for solubility indicated by fluorescence generated from complementation with the assay fragment expressed in or provided to the cells. Cell sorting may be used to separate cells exhibiting detectable fluorescence, and thus expressing soluble variants of the test proteins from those cells that do not exhibit detectable fluorescence or exhibit only low level fluorescence.

Preferred in vivo solubility assay embodiments are those in which the individual fragments are sequentially expressed, i.e., expression of the test protein-tag fragment fusion followed by expression of the self-complementing fragment(s) of the reporter. Sequential expression permits insoluble test proteins to aggregate, thereby rendering the reporter fragment to which it is fused inaccessible for complementation with the other fragment(s) of the reporter. Thus, in general, for in vivo solubility assay applications of the invention, expression of the test protein-tag fragment fusion should precede expression of the self-complementing fragment(s) for a period of time sufficient to permit aggregation of insoluble fusions. In some embodiments (e.g., using mammalian cells), expression of the test protein-tag fragment fusion is turned off after the fusion has been expressed, then expression of the self-complementing fragment(s) is activated. In this way, the most accurate assay is performed. In contrast, co-expression of both the reporter fragment-test protein fusion and the self-complementing fragment(s) may compromise solubility assay results, as it permits transient solubility of otherwise insoluble test proteins immediately following expression, thereby permitting self-complementation.

Protein Quantification Assays

Both of the above solubility detection assays may be extended to the quantification of test proteins, and more specifically to the quantification of soluble fraction, insoluble fraction, as well as total protein expression. In one embodiment of an in vitro assay for quantifying soluble and insoluble protein fractions, cells expressing the test protein-tag fragment fusion (e.g., x-GFP s11) are lysed, and the insoluble fraction is pelleted. The supernatant, containing the soluble fraction, is then mixed with the complementary assay fragment (i.e., in a series of microtiter plate wells containing the complementary fragment), and fluorescence is monitored. Alternatively, the assay fragment may be added to the lysate, sequentially, to reaction volume. The degree of fluorescence is directly proportional to the quantity of soluble protein, and soluble protein quantity may be determined by reference to a standard calibration curve (generated as described in Example 6, infra). The insoluble protein fraction is quantified by denaturing and refolding the pellet protein, and combining this preparation with the complementary assay fragment. In a variation of this approach, total protein expression is measured and compared with the soluble quantity to determine insoluble quantity. In a related embodiment, total protein quantity (soluble and insoluble) may be quantified in vitro by co-refolding unfolded complementing fragments (methods of Example 9, infra).

In a related embodiment, total protein quantity (soluble and insoluble) may be assayed in vivo by co-expression of the test protein-tag fragment fusion and the complementary fragment. The degree of fluorescence is proportional to the quantity of total protein. See Example 10, infra.

Sandwich-Format Split-Fluorescent Protein Systems

Reporter fluorescent and chromophoric proteins may be split into three (or more) individual fragments capable of self-complementing to form a reconstituted reporter protein. In one embodiment of a sandwich-format protein detection assay, two tag fragments of the fluorescent or chromophoric protein are fused to a test protein, which fragments, together, are capable of complementing with a third fragment to reconstitute the fluorescent or chromophoric phenotype. For example, a test protein may be inserted between two contiguous beta strands of GFP, i.e., GFP S10-x-GFP S11. Soluble protein detection is accomplished by detectable complementation with GFP 1-9. In this embodiment, complementation of the three fragments identifies the test protein as soluble, and full-length, and indicate that the two fragments of GFP fused to x are functionally linked by x. Particularly in the context of directed evolution strategies, this approach provides the advantage of ensuring that the test protein x is actually full-length and intact (whereas X-GFP S11 would only complement GFP 1-10, not GFP 1-9) guarding against the appearance of truncated versions of the test protein, or versions incorporating internal ribosome binding sites, or proteolyzed versions.

A related, more stringent solubility assay embodiment utilizes two tag fragments fused to a test protein, wherein each of the fragments may be independently detected by functional reconstitution with an independent and distinguishable third complementing assay fragment. More specifically, for example, in a fusion of GFP S10-x-GFP S11, strand 10 would be detectable by circular permutant GFP 11-9 delta 10 (circular permutant 11-1-2-3-4-5-6-7-8-9, where 11 and 1 are linked and 10 is missing, and numbers refer to the strand, see FIG. 3), whereas strand 11 would be detectable by 1-10 delta 11 (1-2-3-4-5-6-7-8-9-10, where 11 is missing). Independent simultaneous detection of the two tags may be facilitated by utilizing color shift variants of GFP in one or both complementing pair(s) (i.e., GFP 11-9 delta 10 could be the cyan variant (Y66W) and GFP 1-10 delta 11 could be the yellow variant (T203Y). Alternatively, the tag fragments could be derived from fluorescent proteins with distinct amino acid sequences, and detected with the appropriate corresponding assay fragment. For example, strand 11 from GFP could be employed to tag the N-terminus of a test protein X and detected with strands 1-10 of GFP, while strand 11 from red fluorescent protein DsRed (Matz et al., 1999, Nat. Biotechnol. 17:969-973) could be simultaneously employed as a fusion to the C-terminus of the same test protein X and detected with strands 1-10 of DsRed.

An alternative embodiment utilizes FRET exhibited between the two reconstituted GFPs linked by the test protein. For example, CFP 11-9 delta 10::10-X-11::YFP 1-10 may be used. Such a construct would be functionally equivalent to CFP-x-YFP, previously shown to exhibit FRET from CFP donor to YFP acceptor as long as x is intact, loosing FRET if x is cleaved, freeing CFP and YFP from proximity, the efficiency of FRET dependent on ($1/r^6$) where r is the distance between the donor and acceptor.

Applications in Prokaryotic and Eukaryotic Cell Culture

The split-fluorescent and split-chromophoric protein systems of the invention may be applied to assays in virtually any cell type, including without limitation bacterial cells (e.g., *E. coli*') and mammalian cells (e.g., CHO cells). One limitation is that expression of GFP and GFP-like proteins is compromised in highly acidic environments (i.e., pH=4.0 or less). Likewise, complementation rates are generally inefficient under conditions of pH of 6.5 or lower (see Example 8, infra).

As will be appreciated by those skilled in the art, the vectors used to express the tag and/or assay fragments must be compatible with the host cell in which the vectors are to reside. Similarly, various promoter systems are available and should be selected for compatibility with cell type, strain, etc. Codon optimization techniques may be employed to adapt sequences for use in other cells, as is well known.

When using mammalian cells for complementation assays of the invention, an alternative to codon optimization is the use of chemical transfection reagents, such as the recently described "chariot" system (Morris et al., 2001, *A peptide carrier for the delivery of biologically active proteins into mammalian cells*. Nature Biotechnol. 19: 1173-1176). The Chariot™ reagent may be used to directly transfect a protein into the cytoplasm of a mammalian cell. Thus, this approach would be useful for an in vivo protein detection assay, wherein the assay fragment may be introduced into the cell, either before or after expression of the genetically-encoded test protein-tag fragment fusion by the cell.

Methods for Isolating Solubility Enhanced Protein Variants

The protein solubility assays described supra may be used in combination with directed evolution strategies aimed at isolating protein variants having improved solubility characteristics relative to a parent, un-evolved protein.

Any method known in the art for generating a library of mutated protein variants may be used to generate candidate test proteins which may be expressed as fusions with a tag fragment. The target protein or polypeptide is usually mutated by mutating the nucleic acid. Techniques for mutagenizing are well known in the art. These include, but are not limited to, such techniques as error-prone PCR, chemical mutagenesis, and cassette mutagenesis. Alternatively, mutator strains of host cells may be employed to add mutational frequency (Greener and Callahan (1995) *Strategies in Mol. Biol.* 7: 32). For example, error-prone PCR (see, e.g., Ausubel, supra) uses low-fidelity polymerization conditions to introduce a low level of point mutations randomly over a long sequence. Other mutagenesis methods include, for example, recombination (WO98/42727); oligonucleotide-directed mutagenesis (see, e.g., the review in Smith, *Ann. Rev. Genet.* 19: 423-462 (1985); Botstein and Shortle, Science 229: 1193-1201 (1985); Carter, *Biochem. J.* 237: 1-7 (1986); Kunkel, "The efficiency of oligonucleotide directed mutagenesis" in Nucleic acids & Molecular Biology, Eckstein and Lilley, eds., Springer Verlag, Berlin (1987), *Methods in Enzymol.* 100: 468-500 (1983), and *Methods in Enzymol.* 154: 329-350 (1987)); phosphothioate-modified DNA mutagenesis (Taylor et al., *Nucl. Acids Res.* 13: 8749-8764 (1985); Taylor et al., *Nucl. Acids Res.* 13: 8765-8787 (1985); Nakamaye and Eckstein, *Nucl. Acids Res.* 14: 9679-9698 (1986); Sayers et al., *Nucl. Acids Res.* 16:791-802 (1988); Sayers et al., *Nucl. Acids Res.* 16: 803-814 (1988)), mutagenesis using uracil-containing templates (Kunkel, *Proc. Nat'l. Acad. Sci. USA* 82: 488-492 (1985) and Kunkel et al., Methods in Enzymol. 154:367-382, 1987); mutagenesis using gapped duplex DNA (Kramer et al., *Nucl. Acids Res.* 12: 9441-9456 (1984); Kramer and Fritz, *Methods in Enzymol.* 154:350-367 (1987); Kramer et al., *Nucl. Acids Res.* 16: 7207 (1988)); and Fritz et al., *Nucl. Acids Res.* 16: 6987-6999 (1988)). Additional methods include point mismatch repair (Kramer et al., *Cell* 38: 879-887 (1984)), mutagenesis using repair-deficient host strains (Carter et al., *Nucl. Acids Res.* 13: 4431-4443 (1985); Carter, *Methods in Enzymol.* 154: 382-403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415-423 (1986)), mutagenesis by total gene synthesis (Nambiar et al., Science 223: 1299-1301 (1984); Sakamar and Khorana, *Nucl. Acids Res.* 14: 6361-6372 (1988); Wells et al., *Gene* 34:315-323 (1985); and Grundstrom et al., *Nucl. Acids Res.* 13: 3305-3316 (1985). Kits for mutagenesis are commercially available (e.g., Bio-Rad, Amersham International). More recent approaches include codon-based mutagenesis, in which entire codons are replaced, thereby increasing the diversity of mutants generated, as exemplified by the RID method described in Murakami et al., 2002, Nature Biotechnology, 20: 76-81.

In a bacterial expression system, clones expressing variants may be rapidly screened for solubility using the above-described in vivo or in vitro assays. Thus, in an in vivo embodiment, a library of clones is generated in *E. coli*, each clone harboring an expressible construct encoding an individual variant protein fused to the tag fragment, under the control of a first and independently inducible promoter. The cells may concurrently harbor an expressible construct encoding the complementary assay fragment, under the control of a second and separately inducible promoter, or the assay fragment polypeptide itself (introduced by protein transfection methods such as described in Morris et al., 2001, supra)

In one in vivo embodiment, cells are induced to express the tag fragment-protein variant fusion, followed by expression of the complementary fragment in the cells. In most preferred embodiments, expression of the fusion is repressed or shutdown for a time sufficient to permit aggregation of insoluble fusion (i.e., 1 h, see Example 4 and Example 10, infra), followed by the induction of complementary fragment expression. In a variation of this approach, the cells only harbor the fusion constructs, preferably under the control of an inducible/repressible promoter, and the complementary fragment is introduced by protein transfection methodologies.

Various in vitro embodiments are possible. Generally, these comprise the expression of the variant protein-tag fragment fusions in, for example, *E. coli*, followed by cell lysis and reaction with the complementary assay fragment polypeptide.

Protein Purification

Another aspect of the invention is the use of split-fluorescent and split-chromophoric protein systems to purify proteins identified as soluble in the solubility assays described, supra. Briefly, a split-fluorescent or split-chromophoric protein fragment is modified to contain a moiety or amino acid residues that functionalize the fragment to bind to a substrate, allowing the substrate with the attached fragment to be used to bind and purify polypeptides fused with the complementary split-fluorescent or split-chromophoric protein fragment using purification methods well known in the art. In one embodiment, the tag fragment is functionalized to bind to glass beads, using chemistries well known and commercially available (e.g., Molecular Probes Inc., Eugene, Oreg.). Alternatively, the assay fragment is functionalized to bind to glass beads, and used to specifically bind and thereby purify polypeptides of interest fused with the complementary tag polypeptide fragment. The polypeptide of interest can be specifically recovered by providing a means for cleaving the polypeptide of interest from the fused tag fragment using methods well-known in the art. For example, the cDNA nucleic acid encoding the polypeptide of interest fused with the tag fragment can be engineered to include a nucleotide sequence encoding the amino acids comprising a protease cleavage site between the polypeptide of interest and the tag fragment. The resulting expressed fusion polypeptide will contain the protease cleavage site between the protein of interest and the tag fragment (such as the sequence ENLYFQG (SEQ ID NO: 81) of the tobacco etch virus (TEV) protease (Parks, T.D., et. al., *Anal. Biochem.*, 216:413-417, (1994)). After the fusion has been bound to the assay fragment attached to the glass beads, and is purified, the protease is then admixed with the glass beads, contacting the protease recognition site, thereby cleaving the polypeptide of interest from the tag fragment and enabling the recovery of the polypeptide of interest. Such viral protease cleavage systems, and their uses for protein purification methods are well known in the art and are commercially available (for example, the AcTEV™ protease and associated protein purification system, Invitrogen Corporation, Carlsbad, Calif.).

Beads with attached assay fragments may be regenerated by mixing the beads with a suitable chemical denaturant such as 9 M urea, thereby unfolding the assay fragment and releasing the tag fragment. The assay fragment is then refolded by diluting away the 9 M urea using a suitable buffer such as TRIS or MOPS. The assay fragment remains attached to the glass beads throughout this procedure, due to the covalent linkage provided by the attachment chemistry. Alternatively, as described in Example 13, infra, the tag fragment is modified to incorporate histidine residues in order to functionalize the tag to bind to commercially available metal affinity resin beads (TALON® resin, Clontech, Palo Alto, Calif.). In a specific embodiment, a GFP s11 fragment was engineered so that all outside pointing residues in the β-strand were replaced with histidine residues. This HIS-modified tag fragment is non-perturbing to test proteins fused therewith, and is capable of detecting soluble protein upon complementation with the GFP 1-10 assay fragment (Example 13). The HIS-modified tag fragment can be used to purify proteins in metal affinity resin bead columns, and enables the quantification of soluble and insoluble protein as well as the purification and elution of protein to 95% purity without the need for any another purification tag system. See Examples 13-17, infra.

Precomplementation

The rate of fluorescence formation during complementation of GFP fragments can be vastly increased by using fragments of GFP in which the chromophore has been pre-formed in the fragment bearing the relevant chromophore amino acids, relative to fragments in which the chromophore cyclization has never occurred. Briefly, a non-fluorescent precomplemented GFP fragment bearing the chromophore amino acids can be formed by: (1) mixing the fragment with the complementary fragment(s) not containing the chromophore amino acids; (2) allowing the complementation reaction and formation of fluorescence to go to completion; (3) unfolding the fragments, for example by chemical means, to generate unfolded non-fluorescent GFP fragments; (4) recovering the fragment containing the chromophore amino acids and separating it from the other fragment(s); (5) renaturing the fragment bearing the chromophore amino acids. This fragment remains substantially non-fluorescent even though it contains the cyclized chromophore because it has been is substantially unfolded by chemical or other means so as to be non-fluorescent, and remains unfolded in the absence of the complementary fragment(s). Rapid restoration of fluorescence can be obtained without having to generate the covalent modifications associated with the chromophore simply by re-adding the complementary, non-chromophore-containing GFP fragment(s). By this approach, because the slow chromophore cyclization reaction is complete, formation of fluorescence during complementation is limited only by the rate of binding of the complementary fragments and formation of the folded beta-barrel native structure.

Split-Protein Fragment Engineering

Directed Evolution Strategy for Isolating Soluble Self-Complementing Fragments

Another aspect of the invention relates to methods for generating ideal split protein interactors by directed evolution and sequential induction of fragments. The incorporation of sequential induction contrasts with the existing published approaches specifying co-induction of split fragments. Briefly, in the sequential induction approach, fragment 1 is held constant and fragment 2 is evolved. When fragment 1 is held constant and fragment 2 is evolved, fragment 2 is first expressed, then expression is shut off. The fragment is allowed to aggregate or remain soluble. Next, fragment 1 is expressed. If both fragments are expressed simultaneously, this can lead to false positives because complementation can occur prior to aggregation. Sequential expression leads to the selection of true positives, i.e., soluble variants. Following the selection of an optimum fragment 2 variant, this variant is then held constant and fragment 1 is then evolved. The process may be continued using further sequential inductions until the desired fragment solubilities are attained. Using this approach, the resulting fragments can be engineered to be soluble on their own prior to complementation.

Attenuating Solubility Perturbation of Detectable Proteins

Soluble fragments may be further engineered to reduce their perturbing effect on the solubility of fused passenger domains (test proteins). Briefly, a test protein which is less soluble when fused to the fragment than when expressed alone is used as a 'bait' domain in a directed evolution approach aimed at engineering the fragment such that the fusion and non-fusion solubilities are similar thereby reducing the effect of the fragment on the solubility of the test protein. This strategy was employed in optimizing a small fragment of GFP, resulting in a variant with attenuated perturbing effect on fused passenger proteins (see, Example 4, infra).

Kits

Another aspect of the invention provides split-fluorescent and split-chromophoric protein system kits useful in conducting the various assays described, supra. Kits of the invention may facilitate the use of split-fluorescent and split-chromophoric systems of the invention. Various materials and reagents for practicing the assays of the invention may be provided. Kits may contain reagents including, without limitation, polypeptides or polynucleotides, cell transformation and transfection reagents, reagents and materials for purifying polypeptides, protein denaturing and refolding reagents, as well as other solutions or buffers useful in carrying out the assays and other methods of the invention. Kits may also include control samples, materials useful in calibrating the assays of the invention, and containers, tubes, microtiter plates and the like in which assay reactions may be conducted. Kits may be packaged in containers, which may comprise compartments for receiving the contents of the kits, instructions for conducting the assays, etc.

For example, kits may provide one or more split-fluorescent protein fragments of the invention, one or more polynucleotide vectors encoding one or more fluorescent protein fragments, bacterial cell strains suitable for propagating the vector, cells pretransformed or stably transfected with constructs encoding one or more fluorescent protein fragments, and reagents for purification of expressed fusion proteins.

In one embodiment of a kit which facilitates conducting the protein detection assays of the invention, the kit contains a recipient nucleic acid vector containing the coding sequence of a tag fluorescent or chromophoric protein fragment (i.e., GFP S11), which includes a multiple cloning site for inserting test protein in-frame at the N-terminus of the tag fragment coding sequences. Optionally, the insertion site may be followed by the coding sequence of a linker polypeptide in frame with the coding sequence of the downstream tag sequence. A specific embodiment is the pTET-SpecR plasmid, the engineering of which is described in Example 1 and which is illustrated in FIG. 1. The complete nucleotide sequence of the pTET-SpecR plasmid is shown in FIG. 1 B.

This recipient, or "tag vector" is used to produce test protein-tag fusions in suitable host cells. In an in vitro assay embodiment, the kit further contains a pre-purified assay fragment (i.e., GFP 1-10 polypeptide) used to detect the test protein-tag fragment fusions expressed by the tag vector. In an in vivo assay embodiment, the kit further contains an "assay vector" which is compatible with the tag vector and encodes the assay fragment under the control of an independently regulated promoter. In an alternate in vivo assay embodiment, cells containing an assay vector (i.e., vector encoding GFP 1-10 under the control of an inducible promoter) are provided in the kit, along with a compatible tag vector into which test proteins may be cloned, wherein expression in controlled by a separately inducible promoter. The cells containing the assay vector may be transformed with the tag vector, and cell fluorescence monitored.

Materials for calibrating the solubility assays of the invention may be provided. In one embodiment, the kit contains a purified sulfite reductase-GFP S11 fusion protein reagent.

Fluorescent and Chromophoric Proteins

The invention provides methods and principles for the design of split-fluorescent and split-chromophoric protein systems, and is herein exemplified by the generation and molecular evolution of optimal split-GFP systems for use in protein detection and quantification. However, other GFP-like proteins may be used in the practice of the invention.

One group of fluorescent proteins includes the Green Fluorescent Protein isolated from *Aequorea victoria* (GFP), as well as a number of GFP variants, such as cyan fluorescent protein, blue fluorescent protein, yellow fluorescent protein, etc. (Zimmer, 2002, Chem. Rev. 102: 759-781; Zhang et al., 2002, Nature Reviews 3: 906-918). Typically, these variants share about 80%, or greater sequence identity with SEQ ID NO:2 (or SEQ ID NO:8.) These color-shift GFP mutants have emission colors blue to yellow-green, increased brightness, and photostability (Tsien, 1998, Annual Review of Biochemistry 67: 509-544). One such GFP mutant, termed the Enhanced Yellow Fluorescent Protein, displays an emission maximum at 529 nm. Another recently described mutant, a gold variant, was generated by incorporating a non-natural variant of tryptophan into the cyan variant, and is characterized by a significantly red-shifted emission maximum of 574 nm (Bae et al., 2003, J. Mol. Biol. 328: 1071-1081).

Additional GFP-based variants having modified excitation and emission spectra (Tsien et al., U.S. Patent Appn. 20020123113A1), enhanced fluorescence intensity and thermal tolerance (Thastrup et al., U.S. Patent Appn. 20020107362A1; Bjorn et al., U.S. Patent Appn. 20020177189A1), and chromophore formation under reduced oxygen levels (Fisher, U.S. Pat. No. 6,414,119) have also been described. GFPs from the Anthozoans *Renilla reniformis* and *Renilla kollikeri* have also been described (Ward et al., U.S. Patent Appn. 20030013849).

Additionally, over 100 GFP-like fluorescent proteins and non-fluorescent chromoproteins from the class Anthozoa have now been identified (for review, see Verkusha et al., 2003, *GFP-like fluorescent proteins and chromoproteins of the class Anthozoa*, In: Protein Structures: Kaleidoscope of Structural Properties and Functions, pp. 405-439, Ed. V. Uversky. Research Signpost Press, Kereala, India). This group of *Anthozoa* proteins includes the red fluorescent protein isolated from *Discosoma* species of coral, DsRed (Matz et al., 1999, Nat. Biotechnol. 17:969-973), and various DsRed variants (e.g., DsRed1, DsRed2). DsRed and the other *Anthozoa* fluorescent proteins share only about 26-30% amino acid sequence identity to the wild-type GFP from *Aequorea victoria*, yet all the crucial motifs are conserved, indicating the formation of the 11-stranded beta-barrel structure characteristic of GFP. The crystal structure of DsRed has also been solved, and shows conservation of the 11-stranded beta-barrel structure of GFP MMDB Id: 5742.

A number of mutants of the longer wavelength red fluorescent protein DsRed have also been described. For example, recently described DsRed mutants with emission spectra shifted further to the red may be employed in the practice of the invention (Wiehler et al., 2001, FEBS Letters 487: 384-389; Terskikh et al., 2000, Science 290: 1585-1588; Baird et al., 2000, Proc. Natl. Acad. Sci. USA 97: 11984-11989). Recently, a monomeric variant of DsRed was described (Campell et al., 2002, Proc. Natl. Acad. Sci. USA 99: 7877-7882). This variant, termed "mRFP1", matures quickly (in comparison to wild type DsRed, which matures over a period of 30 hours), has no residual green fluorescence, and has excitation and emission wavelengths of about 25 nm longer than other DsRed variants.

An increasingly large number of other fluorescent proteins from a number of ocean life forms have recently been described, and the Protein Data Bank currently lists a number of GFP and GFP mutant crystal structures, as well as the crystal structures of various GFP analogs. Related fluorescent proteins with structures inferred to be similar to GFP from corals, sea pens, sea squirts, and sea anemones have been described, and may be used in the generation of the split-fluorescent protein systems of the invention (for reviews, see Zimmer, 2002, Chem. Rev. 102: 759-781; Zhang et al., 2002, Nature Reviews 3: 906-918).

Additionally, fluorescent proteins from *Anemonia majano*, *Zoanthus* sp., *Discosoma striata*, *Discosoma* sp. and *Clavularia* sp. have also been reported (Matz et al., supra). A fluorescent protein cloned from the stony coral species, *Trachyphyllia geoffroyi*, has been reported to emit green, yellow, and red light, and to convert from green light to red light emission upon exposure to UV light (Ando et al., 2002, Proc. Natl. Acad. Sci. USA 99: 12651-12656). Recently described fluorescent proteins from sea anemones include green and orange fluorescent proteins cloned from *Anemonia sulcata* (Wiedenmann et al., 2000, Proc. Natl. Acad. Sci. USA 97: 14091-14096), a naturally enhanced green fluorescent protein cloned from the tentacles of *Heteractis magnifica* (Hongbin et al., 2003, Biochem. Biophys. Res. Commun. 301: 879-885), and a generally non fluorescent purple chromoprotein displaying weak red fluorescence cloned from *Anemonia sulcata*, and a mutant thereof displaying far-red shift emission spectra (595 nm) (Lukyanov et al., 2000, J. Biol. Chem. 275: 25879-25882).

A recently described red fluorescent protein isolated from the sea anenome *Entacmaea quadricolor*, EqFP611, is a far-red, highly fluorescent protein with a unique co-planar and trans chromophore (Wiedenmann et al., 2002, Proc. Natl. Acad. Sci. USA 99: 11646-11651). The crystal structure of EqFP611 has been solved, and shows conservation of the 11-stranded beta-barrel structure of GFP MMDB Id: 5742 (Petersen et al., 2003, J. Biol. Chem., Aug. 8, 2003; M307896200).

Still further classes of GFP-like proteins having chromophoric and fluorescent properties have been described. One such group of coral-derived proteins, the pocilloporins, exhibit a broad range of spectral and fluorescent characteristics (Dove and Hoegh-Guldberg, 1999, PCT application WO 00/46233; Dove et al., 2001, Coral Reefs 19: 197-204). Recently, the purification and crystallization of the pocilloporin Rtms5 from the reef-building coral *Montipora efflorescens* has been described (Beddoe et al., 2003, Acta Cryst. D59: 597-599). Rtms5 is deep blue in color, yet is weakly fluorescent. However, it has been reported that Rtms5, as well as other chromoproteins with sequence homology to Rtms5, can be interconverted to a far-red fluorescent protein via single amino acid substitutions (Beddoe et al., 2003, supra; Bulina et al., 2002, BMC Biochem. 3: 7; Lukyanov et al., 2000, supra).

Various other coral-derived chromoproteins closely related to the pocilloporins are also known (see, for example, Lukyanov et al. 2000, J. Biol. Chem. 275: 25879-82; Gurskaya et al., 2001, FEBS Letters 507: 16-20). To the extent that these chromoproteins contain the conserved 11-stranded beta barrel structure of GFP and other fluorescent proteins, they may be split into self-complementing fragments and used in the assay systems as described herein.

Any fluorescent protein that has a structure with a root mean square deviation of less than 5 angstroms, often less than 3, or 4 angstroms, and preferably less than 2 angstroms from the 11-stranded beta-barrel structure of MMDB Id:5742 may be used in the development of self-complementing fragments. In some cases, fluorescent proteins exist in multimeric form. For example, DsRed is tetrameric (Cotlet et al., 2001, Proc. Natl. Acad. Sci. USA 98: 14398014403). As will be appreciated by those skilled in the art, structural deviation between such multimeric fluorescent proteins and GFP (a monomer) is evaluated on the basis of the monomeric unit of the structure of the fluorescent protein.

As appreciated by one of ordinary skill in the art, such a suitable fluorescent protein or chromoprotein structure can be identified using comparison methodology well known in the art. In identifying the protein, a crucial feature in the alignment and comparison to the MMDB ID:5742 structure is the conservation of the beta-barrel structure (i.e., typically comprising 11 beta strands, but in at least one case, fewer beta strands (see, Wiedenmann et al., 2000, supra), and the topology or connection order of the secondary structural elements (see, e.g., Ormo et al. "Crystal structure of the *Aequorea victoria* green fluorescent protein."Yang et al, 1996, Science 273: 5280,1392-5; Yang et al., 1996 Nat. Biotechnol. 10:1246-51). Typically, most of the deviations between a fluorescent protein and the GFP structure are in the length(s) of the connecting strands or linkers between the crucial beta strands (see, for example, the comparison of DsRed and GFP in Yarbrough et al., 2001, Proc Natl Acad Sci USA 98:462-7). In Yarbrough et al., alignment of GFP and DsRed is shown pictorially. From the stereo diagram, it is apparent that the 11 beta-strand barrel is rigorously conserved between the two structures. The c-alpha backbones are aligned to within 1 angstrom RMSD over 169 amino acids, although the sequence identity is only 23% comparing DsRed and GFP.

In comparing structure, the two structures to be compared are aligned using algorithms familiar to those in the art, using for example the CCP4 program suite. COLLABORATIVE COMPUTATIONAL PROJECT, NUMBER 4, 1994. "The CCP4 Suite: Programs for Protein Crystallography". Acta Cryst. D50, 760-763. In using such a program, the user inputs the PDB coordinate files of the two structures to be aligned, and the program generates output coordinates of the atoms of the aligned structures using a rigid body transformation (rotation and translation) to minimize the global differences in position of the atoms in the two structures. The output aligned coordinates for each structure can be visualized separately or as a superposition by readily-available molecular graphics programs such as RASMOL, Sayle and Milner-White, September 1995, Trends in Biochemical Science (TIBS), Vol. 20, No. 9, p. 374.), or Swiss PDB Viewer, Guex, N. and Peitsch, M. C., 1996 Swiss-PdbViewer: A Fast and Easy-to-use PDB Viewer for Macintosh and PC. Protein Data Bank Quarterly Newsletter 77, pp. 7.

In considering the RMSD, the RMSD value scales with the extent of the structural alignments and this size is taken into consideration when using the RMSD as a descriptor of overall structural similarity. The issue of scaling of RMSD is typically dealt with by including blocks of amino acids that are aligned within a certain threshold. The longer the unbroken block of aligned sequence that satisfies a specified criterion, the 'better' aligned the structures are. In the DsRed example, 164 of the c-alpha carbons can be aligned to within 1 angstrom of the GFP. Typically, users skilled in the art will select a program that can align the two trial structures based on rigid body transformations, for example, as described in Dali et al., Journal of Molecular Biology 1993, 233, 123-138. The output of the DALI algorithm are blocks of sequence that can be superimposed between two structures using rigid body transformations.

Regions with Z-scores at or above a threshold of Z=2 are reported as similar. For each such block, the overall RMSD is reported.

The RMSD of a fluorescent protein or chromoprotein for use in the invention is within 5 angstroms for at least 80% of the sequence within the 11 beta strands. Preferably, RMSD is within 2 angstroms for at least 90% of the sequence within the 11 beta strands (the beta strands determined by visual inspection of the two aligned structures graphically drawn as superpositions, and comparison with the aligned blocks reported by DALI program output). As appreciated by one of skill in the art, the linkers between the beta strands can vary considerably, and need not be superimposable between structures.

In preferred embodiments, the fluorescent protein or chromoprotein is a mutated version of the protein or a variant of the protein that has improved folding properties or solubility in comparison to the protein. Often, such proteins can be identified, for example, using methods described in WO0123602 and other methods to select for increased folding.

For example, to obtain a fluorescent protein with increased folding properties, a "bait" or "guest" peptide that decreases the folding yield of the fluorescent protein is linked to the fluorescent protein. The guest peptide can be any peptide that, when inserted, decreases the folding yield of the fluorescent protein. A library of mutated fluorescent proteins is created. The bait peptide is inserted into the fluorescent protein and the degree of fluorescence of the protein is assayed. Those clones exhibit increased fluorescence relative to a fusion protein comprising the bait peptide and parent fluorescent protein are selected (the fluorescent intensity reflects the amount of properly folded fluorescent protein). The guest peptide may be linked to the fluorescent protein at an end, or may be inserted at an internal site.

In a particular embodiment, wild-type and mutant fluorescent proteins and chromoproteins useful in the practice of the invention may be experimentally "evolved" to produce extremely stable, "superfolding" variants. The methods described in co-pending, co-owned U.S. patent application Ser. No. 10/423,688, filed Apr. 24, 2003, hereby incorporated by reference in its entirety, may be employed for the directed evolution of GFP, DsRed, and any number of related fluorescent proteins and chromoproteins. Such superfolding variants may be split into self-complementing fragments, which fragments may be further evolved to modulate solubility characteristics of the fragments alone or when fused to test protein.

Particular methods for the evolution of soluble and non-perturbing (to test protein solubility) variants of split-fluorescent or chromophoric protein fragments are provided under the subheading SPLIT-PROTEIN FRAGMENT ENGINEERING, supra.

EXAMPLES

Various aspects of the invention are further described and illustrated by way of the several examples which follow, none of which are intended to limit the scope of the invention.

Example 1

Constructing Plasmid pTET-SpecR

The commercial tet-promoter PRO Bacterial expression system (Clontech, Palo Alto, Calif.) has the regulatory protein tetR on a second plasmid separate from the expression plasmid, making the creation of large libraries inefficient. To overcome this limitation, we combined the tet promoter which controls the expression of target proteins, and regulatory protein tetR, on a single plasmid containing the tetracycline-inducible promoter tet, the tet promoter regulatory protein tetR, and the selectable antibiotic marker SpecR, which confers resistance to the antibiotic spectinomycin. The ColE1 origin of replication allows this plasmid to co-exist in cells carrying plasmids with a compatible origin such as the p15 origin. This allows one protein, such as a protein tagged with a fragment of GFP, to be expressed from the pTET plasmid, and another protein, such as the complementary GFP assay fragment, to be expressed from a second plasmid, such as a pET vector (Novagen, Madison, Wis.). The pTET-SpecR plasmid is pictured in FIG. 1 A, and the sequences of the plasmid and the genetic elements are shown in FIG. 1B.

The pTET-SpecR plasmid was engineered by overlap PCR, combining elements from the commercial pPROTet.6×HN vector, pPROLAR vector, and the autonomously-replicating plasmid carried by the BL21-PRO strain (Clontech, Palo Alto, Calif.). The chloramphenicol resistance gene was replaced by the spectinomycin resistance marker cloned from the autonomously-replicating plasmid carried by the BL21-PRO strain, and placed under the control of the promoter of the kanamycin resistance marker of the pPROLAR vector. We cloned the tetracycline repressor (tetR) protein from the spectinomycin-resistant, autonomously-replicating plasmid isolated from BL21-PRO strain, upstream of the T0 transcription termination sequence. The amount of translated tetR is regulated by a weak Shine-Delgarno sequence downstream of SacI, engineered by selecting a variant of the Shine-Delgarno from a small degeneracy library to minimize leakage and maximize induction after addition of anhydrotetracycline (see infra). The SpeI restriction site present in the commercial version was silenced. The new plasmid "pTET-SpecR" was digested with NcoI and XbaI restriction endonucleases (New England Biolabs, Beverly, Mass.) to receive the GFP S11 split GFP cloning cassette. The structure of the resulting cloning site is Nco-1::6HIS::thrombin cleavage site::Nde-1::frame shift stuffer::B amHI:(GGGS; residues 1-4 of SEQ ID NO: 37):SpeI::GFP S11 (TAA Stop)::KpnI. Sense strand of cloning cassette flanked by NcoI and KpnI:

```
                                          [SEQ ID NO: 23]
 NcoI
CCATGGGCAGCAGCCATCATCATCATCATCACAGCAGCGGCCTGGTGC

           NdeI              BamHI        SpeI
CGCGCGGCAGCCATATGGGTGGCGGTTCTGGATCCGGAGGCACTAGTG

           KpnI
GTGGCGGCTCAGGTACC
```

A frame shift stuffer is preferably added between NdeI and BamHI restriction sites, to avoid background expression due to religated vector.

Example 1 of frame-shift stuffer: FS0

```
Sequence  CATATGTGTTAACTGAGTAGGATCCG [SEQ ID NO: 24]

Frame 1    H  M  C  *  L  S  R  I

Frame 2     I  C  V  N  *  V  G  S

Frame 3      Y  V  L  T  E  *  D  P
```

Example 2 of frame-shift stuffer: FS1

```
Sequence: CATATGTAATTAATTAATTGGATCCG [SEQ ID NO: 25]

Frame 1    H  M  *  L  I  N  W  I

Frame 2     I  C  N  *  L  I  G  S

Frame 3      Y  V  I  N  *  L  D  P
```

The C-terminal split protein fragment, such as GFP strand 11 or GFP strands 10-11, is cloned between restriction sites SpeI and KpnI using specific oligonucleotide primers to provide the flanking restriction sites and the coding sequence for the desired fragment. The fragment can also be amplified from a template DNA source and the restriction sites incorporated using specific oligonucleotide primers and PCR, methods well-known in the art. It is clear to one with skill in the art that the completed NcoI/KpnI cassette can be transferred to other expression vectors or systems such as the pET vector by engineering the appropriate restriction sites into the destination vector, and other restriction sites can be employed.

The tetR gene was amplified using the plasmid isolated from BL21 (DE3) PRO cells (Clontech, Palo Alto, Calif.). Amplification of the entire gene was realized by using 5' and 3' specific primers of the tetR gene sequence. The sense primer contained a SacI restriction site followed by a Shine-Delgarno sequence optimized for optimal repression/induction of recombinant protein under the control of the tet promoter (see this example, infra). The downstream primer contained a region homologous to the TO transcription terminator sequence of the PROTet plasmid. The resulting PCR product was assembled with the TO terminator amplicon and the final product was cloned via the SacI/SpeI restriction sites of the PROTet™ 6×HN vector (Clontech, Palo Alto, Calif.), previously modified by silencing common restriction sites by PCR-mediated site-directed mutagenesis by methods well known in the art. The spectinomycin resistance gene was amplified from the plasmid isolated from BL21 DE3 PRO using gene-specific primers:

```
P1:
                                      [SEQ ID NO: 26]
CAGGATGAGGATCGTTTCGCATGGTAACGGCGCAGTGGCG,

P2:
                                      [SEQ ID NO: 27]
CGCCACTGCGCCGTTACCATGCGAAACGATCCTCATCCTG,

P3:
                                      [SEQ ID NO: 28]
GCATTATTTGCCGACTACCTTGGTGATCTCGCC,

P4:
                                      [SEQ ID NO: 29]
ACCCCAGAGTCCCGCATTATTTGCCGACTACCTT, .
```

P1 and P2 primers included the sequence of the kanamycin promoter from the pPROLar vector (Clontech, Palo Alto, Calif.) and P3 and P4 primers included the junction between the end of kanamycin site and SacI. The complete cassette was moved to the new pTET-SpecR plasmid via AatII/SacI restriction sites. The stuffers v1:

```
                                      [SEQ ID NO: 30]
CATATGGGTGGCGGTTCTGGATCCGGAGGCACTAGTGGTGGCGGCTCAG

GTACCTAACTCGAG
```

and v2:

```
                                      [SEQ ID NO: 31]
CATATGGGTGGCACTAGTGGTGGCGGCTCAGGTACCTAACTCGAG
```

were engineered from overlapping primers and cloned into the pTET-SpecR plasmid via NcoI and XbaI, to yield pTET-SpecR v1 and v2 plasmids. The Shine-Delgarno sequence that controls the translation of the tetR protein was optimized by mutagenesis and selection. Briefly, the folding reporter GFP gene was cloned into NdeI-BamHI of the stuffer v1 pTET-SpecR plasmid transformed into a DH10B strain. The tetR gene was amplified using degenerate primers for four nucleotides of the Shine-Delgarno sequence and the cassette was cloned SacI/SpeI into the GFP containing pTET-SpecR receiving vector. The resulting library was transformed into a BL21 DE3 strain. Optimal variants were screened by calculating the induction ratio (GFP fluorescence of cells after induction divided by GFP fluorescence of cells before induction) and selecting the variants with the maximal induction ratio upon addition of 0.25 μg/ml anhydrotetracycline (AnTET) (Table 1). The Shine-Delgarno sequence for the optimal tetR sequence showing the largest induction ratio is:

```
AATAAACATTAATG.        [SEQ ID NO: 32]
```

TABLE 1

Whole cell fluorescence of GFP expressed in optimum pTET-SpecR vector and in PROTet Cm$^R$ commercial vector.

| | Whole-cell fluorescence | |
|---|---|---|
| | [a]Pre-induction | [b]Post-induction |
| GFP- pTET-Spec$^R$::GFP | 28 | 1540 |
| GFP-PROTet-Cm$^R$::GFP (Clontech) | 10 | 1930 |

[a]Fluorescence before induction.

[b]Fluorescence after 3 h induction at 37° C. at 250 ng/ml anhydrotetracycline.

Example 2

Finding Feasible Pairs of Split GFP

To achieve the split GFP protein tagging and detection scheme outlined in FIG. 2, we first tested several pairs of fragments from either folding reporter GFP, which bears the mutations F99S, M153T, V163A (Crameri, Whitehorn et al. 1996), F64L, and S65T (Patterson, Knobel et al. 1997), or the exceptionally stable "superfolder" GFP, containing the folding reporter GFP mutations and S30R, Y39N, N105T, Y145F, I171V, and A206V. We separately co-expressed several pairs of GFP fragments on compatible plasmids in *E. coli*, including amino acids 1-145+145-238, 1-155+156-238, 1-171+171-238, 1-195+196-238, 1-214+214-238. The junction points corresponded to loops or turns between β-strands (Tsien 1998; Baird, Zacharias et al. 1999) (see FIG. 3). Fragment pairs from superfolder GFP consistently gave much brighter colonies than the same pairs from folding reporter GFP. For example, superfolder GFP fragments from split at 156 and 172 were brighter than fragments derived from folding reporter GFP (see FIG. 4). Our objective was to minimize the size of one of the fragments for use as a protein tag, so we focused on the feasible pair with the smallest fragment (1-214+214-238). To further reduce the size of the tagging domain, we also tested 1-214 (GFP 1-10) for complementation with 214-230 (GFP S11), eliminating the disordered residues 231-238 (Tsien 1998) from the small fragment. Table 2 shows the sequences of the GFP S11 constructs including the wild type and engineered mutants.

TABLE 2

Sequences of GFP S11 variants.

| Fragment | [a,b]Amino acid sequence |
|---|---|
| | 215 220 225 230 |
| GFP S11 wild type [SEQ ID NO: 10] | [c]KRDHMVLLEFVTAAGITGT |
| GFP S11 M1 (L221H) [SEQ ID NO: 12] | [c]KRDHMVL**H**EFVTAAGITGT |
| [d]GFP S11 M2 (L221H, F223S, T225N) [SEQ ID NO: 14] | [c]KRDHMVL**H**E**S**V**N**AAGGT |
| GFP S11 M3 (L221H, F223Y, T225N) [SEQ ID NO: 16] | [e]RDHMVLHEYVNAAGIT |

[a]Point mutations found by directed evolution in bold. Unless otherwise noted, sequences stop at amino acid 230 in GFP, additional C-terminal GT amino acid motif coded by KpnI site.
[b]Numbering corresponds to position in full-length GFP.
[c]C-terminal GT amino acid motif comes from KpnI site, followed by TAA stop codon.
[d]Sequence stops at amino acid 228 in GFP, followed by GT from KpnI site.
[e]Sequence starts at amino acid 215 in GFP sequence. Stop codon after amino acid 230.

Co-expression of the superfolder GFP fragments 1-214 (GFP 1-10) and 214-230 (GFP S11 wild type) from pET vectors with compatible origins (Novagen, Madison, Wis.) gave fluorescent *Escherichia coli* (*E. coli*) colonies (FIG. 5, inset). No detectable complementation occurred with the corresponding folding reporter GFP fragments (FIG. 5, inset). Superfolder GFP 1-10 was insoluble, but incubation of refolded inclusion bodies (see EXAMPLE 9, infra) with soluble sulfite reductase from *Pyrobaculum aerophilum* (Fitz-Gibbon, Choi et al. 1997) C-terminally tagged with wild type GFP S11 wild type to yield the fusion protein sulfite reductase-GFP S11 wild type, gave a time-dependent increase in fluorescence (FIG. 5, graph).

Example 3

Engineering the GFP Assay Fragment GFP 1-10

We evolved superfolder GFP 1-10 by DNA shuffling (Stemmer 1994) to improve its solubility and increase its complementation with sulfite reductase-GFP 11. Superfolder GFP 1-10 PCR amplicons were subjected to DNA fragmentation and shuffling using published protocols (Stemmer 1994). The GFP 1-10 cDNA library plasmid was transformed into an *E. coli* BL21 (DE3) PRO expression strain (Clontech, Palo Alto, Calif.) containing the sulfite reductase-GFP S11 wild type tagged protein on a pPROTET vector (Clontech, Palo Alto, Calif.). The expression library was plated on nitrocellulose membrane using two successive 400-fold dilutions of a 1.0 $OD_{600}$ nm frozen 20% glycerol/Luria-Bertani (LB) stock. After overnight growth at 37° C., the membrane was transferred to an LB/Agar plate containing 50 μg kanamycin, 35 μg chloramphenicol, and 50 μg spectinomycin per ml of media, plus 1 mM IPTG for 3 h at 37° C., and then moved onto a new plate containing the above antibiotics plus 600 ng/ml anhydrotetracycline (AnTET). Clones exhibiting the most rapid development of fluorescence were picked and frozen as −80° C. 20% glycerol freezer stocks. The clones were grown and induced with 1 mM isopropylthiogalactoside (IPTG), and the soluble lysates were screened for complementation efficiency in an in vitro assay (see infra, EXAMPLE 9) with an excess of purified sulfite reductase-GFP S11 wild type fusion protein. The best candidates were pooled and subjected to another round of evolution. Mutations were confirmed by fluorescent dye terminator DNA sequencing. After three rounds of shuffling and selection of the brightest clones, in vitro complementation of the soluble lysate of the best variant, termed GFP 1-10 OPT, improved 80-fold (FIG. 5, graph) relative to the same amount of refolded superfolder GFP 1-10. In addition to the folding reporter GFP mutations (see supra), GFP 1-10 OPT contains S30R, Y145F, I171 V, A206V from superfolder GFP, and seven new mutations N391, T105K, E111 V, I128T, K166T, I167V, S205T, and is ca. 50% soluble expressed in *E. coli* at 37° C. Ultraviolet-visible spectra of 10 mg/ml solutions of the non-fluorescent GFP 1-10 OPT lacked the 480 nm absorption band of the red-shifted GFP (Tsien 1998) suggesting that the addition of GFP 11 triggers a folding step required to generate the cyclized chromophore (Tsien 1998). Purified GFP 1-10 OPT, superfolder GFP, and folding reporter GFP were each studied by analytical gel filtration loaded at 10 mg/ml. GFP 1-10 OPT eluted as 60% dimer, 35% monomer, and 5% higher-order aggregates, while full-length folding reporter GFP and superfolder GFP both eluted as >95% monomer, with a trace of dimer and higher-order aggregates.

Example 4

Engineering GFP S11

The C-terminal wild type GFP S11 fusion tag dramatically reduced the solubility of several *Pyrobaculum aerophilum* (Fitz-Gibbon, Choi et al. 1997) test proteins (Table 3). 3-hexulose 6-phosphate synthase (HPS) alone was 60% soluble, but insoluble when fused to wild type GFP 11 (FIG. 6, Table 3). Protein solubility was determined by SDS-PAGE and gel densitometry analysis as previously described (Waldo, Standish et al. 1999; Waldo 2003). Briefly, for high-throughput screens, 1 ml cell cultures were pelleted by centrifugation and resuspended in 110 μl of buffer containing 100 mM TRIS, pH 7.5, 150 mM NaCl, and 10% v:v glycerol (TNG buffer). In other cases, 3 ml cell cultures were pelleted by centrifugation and resuspended in 300 10 μl of TNG buffer. After sonication samples were centrifuged to furnish soluble and pellet fractions. Pellets were resuspended in a volume of TNG equal to the sonicant supernatant. 15 μl of the soluble and pellet fractions were mixed with 15 μl of 2×SDS denaturing buffer containing 100 mM TRIS, 200 mM dithiothreitol, 4% SDS, 0.2% bromophenol blue, and 20% glycerol, and were heated for 15 min at 100° C. The denatured samples were resolved on a 4-20% gradient Criterion SDS-PAGE (Biorad, Hercules, Calif.). The protein samples were stained using Gel Code Blue stain reagent (Pierce, Rockford, Ill.) and imaged using a GS-800 Calibrated Densitometer (Biorad, Hercules, Calif.). The calibrated scanner furnished the integrated optical density D of the protein spots. The total expressed protein content was estimated by adding the protein spot optical densities of the soluble ($D_s$) and the pellet fraction ($D_p$) and the solubility was defined as $S=D_s/(D_s+D_p)$. We used HPS as "bait" in a directed evolution schema in *E. coli* to discover mutants of GFP S11 for which the HPS-GFP S11 fusion solubility matched the HPS non-fusion solubility.

TABLE 3

Effect of GFP S11 tags on the solubility of eighteen test proteins from *Pyrobaculum aerophilum.*

| # | [a]Protein | [b]MW | [c]Fraction soluble [d]NF | [e]WT | [f]M1 | [f]M2 | [f]M3 |
|---|---|---|---|---|---|---|---|
| 1 | DNA-directed RNA polymerase | 12.5 | 0.05 | 0.00 | 0.00 | 0.35 | 0.10 |
| 2 | Sulfite reductase | 12.7 | 1.00 | 1.00 | 1.00 | 1.00 | 1.00 |
| 3 | c-type cytochrome biogenesis factor | 14.4 | 0.77 | 0.28 | 0.59 | 0.86 | 0.65 |
| 4 | Translation initiation factor | 15.4 | 0.40 | 0.30 | 0.80 | 0.70 | 0.45 |
| 5 | Ribosomal protein S9p | 16.4 | 0.70 | 0.50 | 0.75 | 0.80 | 0.75 |
| 6 | Polysulfide reductase subunit | 21.0 | 0.00 | 0.00 | 0.00 | 0.00 | 0.00 |
| 7 | Nucleoside diphosphate kinase | 21.6 | 0.00 | 0.00 | 0.00 | 0.15 | 0.10 |
| 8 | Tartrate dehydratase β-subunit | 23.8 | 0.00 | 0.00 | 0.00 | 0.00 | 0.00 |
| 9 | 3-hexulose 6-phosphate synthase | 23.1 | 0.65 | 0.00 | 0.30 | 0.85 | 0.60 |
| 10 | Hydrogenase formation protein hypE | 26.8 | 0.35 | 0.05 | 0.40 | 0.70 | 0.55 |
| 11 | Methyltransferase | 29.3 | 0.00 | 0.00 | 0.00 | 0.05 | 0.05 |
| 12 | Chorismate mutase | 29.3 | 0.70 | 0.00 | 0.35 | 0.65 | 0.70 |
| 13 | Tyrosine t-RNA synthetase | 36.0 | 0.95 | 0.70 | 0.90 | 0.90 | 0.95 |
| 14 | nirD protein | 36.7 | 0.70 | 0.15 | 0.40 | 0.65 | 0.45 |
| 15 | Soluble hydrogenase | 37.3 | 0.00 | 0.00 | 0.00 | 0.05 | 0.00 |
| 16 | Aspartate-semialdehyde. Dehydrog. | 37.4 | 0.00 | 0.00 | 0.00 | 0.05 | 0.00 |
| 17 | Phosphate cyclase | 37.4 | 0.80 | 0.30 | 0.85 | 0.95 | 0.90 |
| 18 | Purine-nucleoside phosphorylase | 41.7 | 0.05 | 0.00 | 0.00 | 0.10 | 0.00 |

[a]Eighteen proteins from the hyperthermophilic archaeon *Pyrobaculum aerophilum* (*Fitz-Gibbon, Choi* et al. 1997), expressed in *E. coli* BL21(DE3) at 37° C.

[b]Theoretical molecular weight in kD calculated from amino acid sequence.

[c]Fraction soluble as determined by SDS-PAGE densitometry. Relative uncertainty is ca. 5%, average of three replicates.

[d]Non-fusion (NF) solubility.

[e]C-terminal fusions with wild-type GFP 11 (WT).

[f]C-terminal fusions with GFP 11 optima (M1, M2, M3).

Libraries of HPS-GFP 11 variants and the GFP 1-10 OPT were expressed in sequence from the pTET-SpecR vector (see EXAMPLE 1, supra) and pET 28 vectors, respectively. This sequential induction protocol using independently-inducible compatible plasmids helped to avoid false-positives caused by co-translational folding and complementation of insoluble variants of HPS-GFP S11 with GFP 1-10 OPT. Hexulose phosphate synthase-GFP 11 (HPS-GFP S11) fusions were amplified by PCR and shuffled using published protocols (Stemmer 1994). The GFP S11 mutant library was expressed as a C-terminal fusion with the bait protein HPS bearing an N-terminal 6-HIS tag, from the pTET plasmid with an AnTET-inducible tet promoter (Lutz and Bujard 1997) (see FIG. 1 and EXAMPLE 1, supra) and transformed into a BL21(DE3) strain expressing GFP 1-10 OPT on a modified pET vector containing a p15 origin of replication. Optima were screened using a sequential induction protocol as follows. After overnight growth at 37° C., the nitrocellulose membrane bearing colonies was moved onto a selective LB/agar Bauer plate containing 300 ng/ml AnTet for 3 h at 37° C. to express the HPS-GFP S11 library, transferred to a fresh "resting" plate for 1 h to allow the AnTet to diffuse out of the colonies to shut off expression of the HPS-GFP S11, and finally moved to an LB/agar plate containing 1 mM IPTG for 2 h to induce expression of the complementary GFP 1-10 OPT from the pET plasmid. Since the HPS-GFP S11 wild type construct was entirely insoluble, colonies expressing the HPS-GFP S11 wild type and GFP 1-10 OPT according to the sequential expression protocol were only faintly fluorescent. Brighter clones, associated with more soluble HPS-GFP 11 optima, were picked into selective liquid culture 96-well tissue culture plates, and saved as −80° C. 20% glycerol stocks. The clones were grown in 1 ml liquid cultures and were induced with 300 ng/ml AnTET. The soluble fractions were screened for complementation efficiency in an in vitro assay with an excess of purified GFP 1-10 OPT (see infra, EXAMPLE 9). Clones with the fastest complementation rates were selected and pooled for an additional round of evolution and screening. Two rounds of evolution yielded two separate GFP S11 mutants, L221 H and T225N.

We initially focused on the L221 H variant, termed GFP 11 M1. This mutation complemented GFP 1-10 OPT efficiently in vivo, and had improved solubility relative to HPS GFP S11 wild type, but did not entirely eliminate the deleterious effect of GFP S11 on fusion protein solubility (FIG. 6, and Table 3). GFP 11 M2 was engineered by combining F223S, a mutation that substantially increased the solubility of a different split GFP fragment (see EXAMPLE 11, infra) with T225N (see Table 3, supra). HPS-GFP 11 M2 solubility was greatly improved relative to either HPS-GFP 11 M1 or HPS-GFP 11 wild type (FIG. 6, Table 3). The complementation rate of HPS-GFP 11 M2 with GFP 1-10 OPT had decreased ca. 5-fold relative to HPS-GFP 11 M1 for comparable amounts of soluble fusion protein (FIG. 7) We removed K214 from GFP S11 M2, a duplicate of the C-terminal residue of GFP 1-10 OPT, and screened a 64-fold degeneracy library at the hotspot position 223 using a degenerate primer set, (methods well known in the art), and cloned the resulting variants of GFP 11 M2 as C-terminal fusions with HPS to search for more conservative mutations. The soluble fractions of ca. 200 clones were screened in an in vitro assay (see EXAMPLE 9, infra) with GFP 1-10 OPT. The best GFP S11 construct (L221 H, F223Y, T225N) (termed GFP S11 M3, amino acid sequence RDHMVLHEYVNAAGIT [SEQ ID NO: 16], see Table 2 supra) balanced reduced perturbation of fusion protein solubility (FIG. 6, Table 2 supra) with good complementation (FIG. 7). We also attempted to improved the complementation of GFP 1-10 OPT by directed evolution following the methods outlined in EXAMPLE 3, supra, using the GFP S11 M2 tag as the complementation target. This produced a variant termed GFP 1-10 A4, which exhibited ca. 5-fold faster complementation with GFP S11 M2 relative to GFP 1-10 OPT. GFP 1-10 A4 contained the superfolder mutations and the additional mutations R80Q, S99Y, T105N, E111 V, 1128T, K166T, E172V, and 5205T. The A4 variant is expressed predominantly as inclusion bodies in *E. coli* and is less useful for in vivo assays relative to the GFP 1-10 OPT. However, variant A4 is useful for in vitro assays since it can be refolded from inclusion bodies simply by dilution of urea-solubilized pellets in fresh TNG buffer, and complements GFP S11 M2 or GFP S11 M3 ca. four-fold faster than does GFP 1-10 OPT.

Example 5

Comparing Effect of Sequential Induction or Co-Induction Using Soluble or Insoluble Versions of GFP 1-10

To test the hypothesis that co-induction could lead to complementation of the insoluble and aggregated superfolder GFP 1-10, we compared sequential and co-induction protocols. BL21(DE3) *E. coli* cells co-transformed with the large GFP 1-10 fragment (folding reporter GFP 1-10, superfolder GFP 1-10, or GFP 1-100PT) on vector pTET with a ColE1 origin, and sulfite reductase-GFP S11 wild type on a pET plasmid with a p15 origin were plated on duplicate nitrocellulose membranes on nutrient agar plates, and grown until ca. 1 mm in diameter overnight. One membrane was processed using the sequential induction protocol (see EXAMPLE 4, supra). Briefly, GFP 1-10 was expressed first using AnTET, followed by resting on a fresh plate to remove the AnTET, followed by expression of sulfite reductase-GFP S11 wild type on a fresh plate containing 1 mM IPTG. A duplicate plate was separately co-induced (plate containing both AnTET and IPTG). The fluorescent colonies were illuminated with 488 nm light using an IllumaTool (LightTools Research, Encinitas, Calif.), and imaged through a 520 nm long-pass filter using a Kodak DC290 digital camera. When superfolder GFP 1-10 is expressed transiently, and allowed to aggregate in vivo prior to induction of the sulfite reductase-GFP S11 wild type, the cells are faint (FIG. 8). In contrast, cells expressing the partially soluble GFP 1-10 OPT and sulfite reductase-GFP S11 constructs are bright whether co-expressed or sequentially expressed, as expected (FIG. 8).

Example 6

Sensitivity of Split GFP Assay Performed In Vitro

We measured fluorescence progress curves for complementation of several different amounts of purified sulfite reductase-GFP S11 M3 in 200 μl reactions in a microtiter plate (FIG. 9). We avoided potential higher-order kinetic effects by initiating the complementation using a high concentration and large molar-excess of GFP 1-10 OPT (800 pmol). For these sensitivity experiments, a 96-well microplate was first blocked with a solution of 0.5% bovine serum albumin (BSA) in buffer TNG (100 mM TRIS pH 7.5, 150 mM NaCl, 10% v:v glycerol) for 10 minutes. 2-fold serial dilutions of TALON® resin-purified (Clontech, Palo Alto, Calif.) 6HIS-sulfite reductase-GFP S11 M3 fusion protein were performed in the same buffer. The dilutions spanned the range 200 to 0.1 pmol per 20 μl aliquot, the aliquots were added to the wells of a 96-well plate, and then complementation was performed using a large excess (800 pmol) of GFP 1-10 OPT (ca. 0.5 mg/ml) added in a 180 μl aliquot such that the concentration of the large fragment was not limiting. To test the effect of crude *E. coli* lysate on the sensitivity of the reaction, in a separate experiment, samples were also spiked by addition of 20 μl of lysate from *E. coli* BL21 (DE3) expressing an irrelevant non-tagged protein prior to the addition of the GFP 1-10 OPT. Fluorescence kinetics ($\lambda_{exc}$=488 nm, $\lambda_{em}$=530 nm) were monitored with a FL600 microplate fluorescence reader (Bio-Tek, Winooski, Vt.), recorded at 3 min intervals, for 15 h. The background fluorescence of a blank sample (20 μl of *E. coli* lysate expressing an irrelevant protein, 100 μl of 0.5 mg/ml GFP 1-10 OPT, and 100 μl of 0.5% BSA in TNG buffer) was subtracted from final fluorescence values. The blank was less than 30% the signal from the lowest target concentration (0.1 pmol sulfite reductase-GFP S11 M3). Complementation fluorescence was a linear function of analyte concentration (FIGS. 9). 10 to 200 pmol amounts of sulfite reductase-GFP S11 M3 could be accurately quantified within 15 min after the addition of GFP 1-10 OPT (FIG. 9A), and 0.1 to 10 pmol required ca. 1 h (FIG. 9B). Progress curves over a wide concentration range could be superimposed by simple linear scaling (FIG. 10), indicating that the kinetics of the reaction was not limited by the concentration of GFP 1-10 OPT. Smooth lines fitted to the curves shown in FIG. 9 can compromise calibration curves for determining the amount of protein in a test sample tagged with the GFP tagging domain, as long as the test sample is measured under the same conditions as employed in measuring the samples of known concentration (for example, the calibration curve exemplified of FIG. 9 A for sulfite reductase-GFP S11 M3, using the same assay reagent concentration of GFP 1-10 OPT, and same volumes of sample). Thus, in FIG. 9 A, the linear fit of fluorescence (Y) to pmol is given by Y=2.46×(pmol)+22.8. Suppose we measure an unknown concentration of tagged protein under the same conditions as the calibration curve, yielding a measured fluorescence of 200 units. Solving for pmol=(Y−22.8)/2.46, and substituting Y=200, we can calculate pmol=(200−22.8)/2.46=72.0 pmol, in agreement with FIG. 9 A.

Example 7

Rapid Binding of the Split GFP Fragments

To distinguish between the binding kinetics of the split GFP fragments and the kinetics of chromophore formation, we performed complementation of TALON® resin-bound 6HIS GFP 1-10 OPT by GFP S11 M3 tagged with N-terminal folding reporter GFP. A 100 μl aliquot of 50% v/v slurry of TALON® resin was saturated with GFP 1-10 OPT bearing an N-terminal 6HIS affinity tag (200 μl of 2 mg/ml protein). The beads (50 μl bed volume) were washed 3 times with 300 μl of TNG buffer to remove unbound GFP 1-10 OPT, the remaining buffer aspirated and discarded, and the fluorescence measured in a 96 well microtiter plate (FIG. 11, Step 1). Excess folding reporter GFP-GFP S11 M3 fusion protein (200 μl of 5 mg/ml protein) was added to the beads, mixed by pipetting for 15 s, rapidly transferred to a small 0.2μ spin filtration column, and washed 3 times with 0.5 ml aliquots of TNG to remove unbound folding reporter GFP-GFP S11 M3 protein. This procedure required approximately 5 min. Beads were transferred to a fresh well of the microtiter plate (FIG. 11, Step 2) and the fluorescence measured at 3 min intervals for 12 h (FIG. 11, Step 3). Fluorescence of the beads showed that folding reporter GFP-GFP S11 M3 protein rapidly bound to 6HIS-GFP 1-10 OPT (FIG. 11, Step 2). The washed beads gained additional fluorescence at a rate comparable to that observed in solution (FIG. 11, Step 3), indicating that the kinetics of fluorescence formation was not limited by the rate of association of the GFP fragments.

Example 8

Robustness of the Complementation Assay and Effect of Adjuvants and pH

We tested the effect of common chemical adjuvants and pH on the complementation reaction. Ten sequential 2-fold sequential dilutions of 9 M urea were performed with TNG. 100 μl aliquots of the ten solutions, ranging in concentration from 9 M down to 0.019 M urea, were combined with 10 μl of sulfite reductase-GFP 11 M3, 10 μl of the assay fragment GFP 1-10 OPT, and 80 μl of TNG buffer. Fluorescence data was collected for 12 h at 3 minute intervals with a FL-600 plate reader (BIOTEK, Winooski, Vt.). The reaction was quenched above 2.0 M urea (FIG. 12). In a separate experiment, the complementation rate improved ca. 30% by 5 mM dithiothreitol, but quenched by 0.1% w/v SDS. We next tested the effect of different pH solutions on the efficiency of the complementation reaction. 10 μl of equimolar solutions of sulfite reductase-GFP S11 M3 fusion protein or S11 wild type peptide were added to 180 μl of an 0.1 M solution containing the appropriate buffer MES (pH 5-6.5), HEPES (pH 6.5-7.5), TRIS (pH 7.5-8.5), BICINE (pH 8.5-9.0), over the pH range 5.0 to 9.0 in 0.5 pH unit intervals. Complementation was initiated by adding 10 μl of GFP 1-10 OPT (4 mg/ml) and complementation kinetics were monitored overnight at 3 min intervals with a FL-600 plate reader (BIOTEK, Winooski, Vt.). Complementation was inefficient below pH 6.5 with an apparent pKa of ca. pH 7.3 (FIG. 13). After complementation the fluorescent GFP moiety displayed a slow time-dependent decrease in fluorescence above 5 M urea ($t_{1/2}\approx 20$ h), and a pKa of ca. 5.5 similar to "enhanced" GFP (Patterson, Knobel et al. 1997).

Example 9

In Vitro Protein Quantification

To test whether the split GFP system could accurately quantify different proteins in vitro, we expressed eighteen *Pyrobaculum* proteins as pET vector constructs with C-terminal GFP S11 M3 tags in liquid culture, and then analyzed the soluble and pellet fractions using SDS-PAGE and the split GFP complementation system (FIG. 14). To assay soluble fractions of the eighteen *Pyrobaculum* proteins for pET-expressed protein quantification tests, and to perform assays on optima during directed evolution of the GFP S11 and GFP 1-10 variants, 20 μl of target protein soluble fractions of cell lysates were mixed with 180 μl of 0.35 mg/ml refolded GFP 1-10 OPT (ca. 600 pmol) in a 96 well microplate (Nunc-Immuno™ plate, Nunc, Rochester, N.Y.). To assay insoluble pellets, 50 μl of each resuspended insoluble fraction was centrifuged, the dried pellets were dissolved by addition of 50 μl of 9 M urea, and then 10 μl of the unfolded samples were assayed by rapid addition of 190 μl of 0.35 mg/ml GFP 1-10 OPT in TNG. The fluorescence values of the pellet assays were scaled by a factor of two to compensate for the lower volume relative to the soluble assays, allowing direct comparison with the soluble fraction assays. The final concentration of urea in the assay was ca. 0.4 M (see EXAMPLE 8, supra and FIG. 12). To quantify the samples by SDS-PAGE, 15 μl of the soluble and pellet fractions were mixed with 15 μl of 2×SDS denaturing buffer containing 100 mM TRIS, 200 mM dithiothreitol, 4% SDS, 0.2% bromophenol blue, and 20% glycerol, and were heated for 15 min at 100° C. The denatured samples were resolved on a 4-20% gradient Criterion SDS-PAGE (Biorad, Hercules, Calif.). The protein spots on gels were stained using Gel Code Blue stain reagent (Pierce, Rockford, Ill.) and imaged and optical density of protein spots quantified using a GS-800 calibrated scanning densitometer (Biorad, Hercules, Calif.). Even though Coomassie dye exhibits protein-dependent variations in staining efficiency (Tal, Silberstein et al. 1985), after the completion of complementation and folding (ca. 6 h), there was a strong correlation between the measured fluorescence values and the amount of protein as visualized by SDS-PAGE (FIG. 14). Insoluble proteins dissolved in 9 M urea (see this example, supra) and diluted 20-fold with buffer containing excess GFP 1-10 OPT gave fluorescence well correlated with the amount of insoluble protein visualized by SDS-PAGE (FIG. 14). In contrast, when solubilized pellets were diluted with fresh buffer prior to the addition of an aliquot of concentrated GFP 1-10 OPT, several of the well-expressed insoluble proteins (i.e., polysulfide reductase and nucleotide diphosphate kinase, Table 3 and FIG. 14) gave no detectable complementation. Likely these proteins had misfolded and aggregated upon dilution, making the GFP 11 M3 tag inaccessible prior to the subsequent addition of the GFP 1-10 OPT moiety.

Example 10

Estimating In Vivo Soluble and Total Protein Using Split GFP Assay System

A practical split protein tagging system could be used in vivo to label and detect either soluble or insoluble proteins. We theorized that soluble protein could be assayed in living *E. coli* cells by first expressing the tagged protein for a limited time, and then shutting off the expression to allow the tagged protein to develop its intrinsic solubility phenotype prior to the subsequent expression of the complementary GFP fragment in the same cellular compartment. From the results of our co-refolding in vitro pellet assays (see EXAMPLE 9, supra), we expected that co-expressing the GFP S11 M3 tagged protein and GFP 1-10 OPT would lead to structural complementation and commitment to the development of GFP fluorescence prior to the aggregation of the test protein in vivo, enabling an estimate of the total expressed protein. *E. coli* BL21 (DE3) cells co-expressing *Pyrobaculum* test proteins with an N-terminal 6HIS and a C-terminal GFP S11 M3 tag from pTET-SpecR plasmids (FIG. 1, see supra), and GFP 1-10 OPT from a pET vector (Novagen, Madison, Wis.), were grown to saturation in LB containing 50 μg/ml kanamycin and 70 μg/ml spectinomycin and diluted in 20% glycerol at OD 600 nm=1.0 for −80° C. freezer stocks. Cells were diluted successively with two 400-fold dilutions in LB and plated on nitrocellulose membranes. After overnight growth at 32° C., the cells were induced sequentially (see EXAMPLE 4, Engineering GFP S11, supra) or co-induced. For the sequential induction, cells on membranes bearing the overnight colonies were incubated for 1.5 h on a plate containing 250 ng/ml AnTet, 1 h on a resting plate, and finally 1 h on 1 mM IPTG plate (note shorter induction times relative to those used for engineering GFP S11, EXAMPLE 4, supra). For the co-induction protocol, membranes bearing the overnight colonies were moved to plates containing both 600 ng/ml AnTET and 1 mM IPTG and incubated for 4 h at 37° C. to co-express both the GFP S11 fusions and the large GFP fragment 1-10. The induced colonies on the plates were illuminated using an Illumatool Lighting System® (LightTools Research, Encinitas, Calif.) equipped with a 488 nm excitation filter, and photographed with a DC290 digital camera (Kodak) through a colored glass filter (520 nm long pass, LightTools Research, Encinitas, Calif.). The fluorescent colonies were imaged after co-expression or after sequential expression, and soluble and pellet fractions of the same constructs were analyzed by SDS-PAGE (FIG. 15) after sequential induction in liquid culture. We assessed the amount of useful, non-aggregated 6HIS-tagged protein by binding soluble fractions to excess TALON® resin (Novagen, Madison, Wis.) prior to the SDS-PAGE analyses. Briefly, to analyze soluble and pellet fractions of the same clones used for the in vivo whole-cell plate complementation assays, the clones were separately grown at 37° C. in a 1 ml 96-well culture plate. Cells were induced in the exponential phase with 250 ng/ml AnTET for 1 h, washed three times with fresh LB, and then induced with 1 mM IPTG for 1.5 h. After induction, the culture pellets were resuspended with 110 μl of TNG buffer, and disrupted by sonication. The lysate was fractionated by centrifugation to yield the soluble and the pellet fractions. 40 μl of the soluble extract of sequentially induced liquid cultures was mixed with an equal volume of 50% v/v slurry of metal affinity resin beads (TALON® resin, Clontech, Palo Alto, Calif.) in TNG buffer and centrifuged briefly. The unbound fraction was removed by pipetting, and the beads were washed successively two times with an excess of TNG buffer. After the last centrifugation step, the buffer was discarded. 40 μl of 2×SDS denaturing buffer were added and heated for 15 min at 100° C. The insoluble fraction was denatured as described (see EXAMPLE 4, supra). The TALON®-bound and denatured samples were each resolved on a 4-20% gradient Criterion SDS-PAGE gel (Bio-Rad, Hercules, Calif.). The protein samples were stained using Gel Code Blue stain reagent (Pierce, Rockford, Ill.) and imaged using a GS-800 Calibrated Densitometer (Biorad, Hercules, Calif.). Co-induction in vivo colony fluorescence reported total protein in agreement with SDS-PAGE, while sequential induction colony fluorescence agreed with SDS-PAGE of TALON®-bound soluble protein (FIG. 15). Colonies expressing highly soluble proteins were bright whether the GFP 1-10 was co-induced or sequentially induced (proteins 2, 4, and 5, FIG. 15). Colonies expressing insoluble proteins were much brighter when the GFP 1-10 was co-induced (proteins 8, 11, 15, 16, and 18, FIG. 15). Proteins 1, 4, 5, 7, 9, 12 and 14 were each less soluble when expressed from the very strong T7 promoter (Studier, Rosenberg et al. 1990) of the pET system (Table 3 and FIG. 14, supra), than from the weaker tet promoter (Lutz and Bujard 1997) of the pTET plasmid (FIG. 15). The influence of promoter strength on protein expression levels and solubility has been noted previously (Makrides 1996; Baneyx 1999; Gerstein, Edwards et al. 2003; Yokoyama 2003; Fahnert, Lilie et al. 2004).

Example 11

Engineering a Split GFP Complementation Pair Consisting of a GFP S10-11 Tag Fragment and GFP 1-9 Assay Fragment Following method of EXAMPLE 2, supra, we identified a feasible split GFP pair comprised of a tag domain consisting of superfolder GFP amino acids 198-238, (GFP S10-11), and a complementary assay fragment consisting of superfolder GFP amino acids 1-198, (GFP 1-9), which produced fluorescent cells when the two fragments were co-expressed in *E. coli*. GFP 1-9 was insoluble expressed alone in *E. coli*. Neither fragment expressed alone was fluorescent. Following the prescription of EXAMPLE 3, supra, and using the sulfite reductase-GFP S10-11 fusion protein as the complementation target, we improved the folding and solubility of the GFP 1-9 by directed evolution to yield the new variant GFP 1-9 OPT, which contained the mutations of superfolder GFP (see EXAMPLE 2, supra) and the additional mutations S2R, T43S, A87V, F114S, and K166T. This fragment was ca. 50% soluble expressed at 37° C. in *E. coli* from a pET 28 vector (Novagen, Madison, Wis.). Next we improved the solubility of GFP S10-11 and reduced its perturbation of fusion protein folding and solubility following the prescription of EXAMPLE 4, supra, using the evolved GFP 1-9 OPT as the complementation target. Superfolder GFP S10-11 tag has the sequence NHYLSTQSVLSKDPNEKRDHMVLLEFVTAAGITHGMDELYK [SEQ ID NO: 35], while the optimized GFP S10-11 has the sequence DHYLSTQTILSKDPNEERDHMVLLESVTAAGITHGMDELYK [SEQ ID NO: 36] (mutations N198D, 5205T, V2061, K214E, F223S). The sensitivity of the in vitro split GFP assay using these fragments was tested according to EXAMPLE 6, supra, but with a limiting amount of GFP 1-9 OPT (2.5 μM GFP 1-90PT). Under these conditions, fluorescence reached a plateau at or above 2.5 uM tagged fragment concentration, as expected (FIG. 16).

Example 12

Engineering A (GFP S10)-X-(GFP 511) Sandwich Tag Format and Detection Using Assay Fragment GFP 1-9 OPT To stringently test when both ends of a target protein were covalently attached, and to reduce potential artifacts associated with tagging only one end of a target protein, such as short fragments caused by proteolysis or internal ribosome binding sites, we engineered a sandwich format where test proteins are expressed as fusions between two small domains of GFP, which are then complemented by a third domain of GFP. In this embodiment, test protein X is expressed as a sandwich between GFP strands 10 and 11 as (GFP S10)-X-(GFP S11) (FIG. 17). This species complements a third domain of GFP, GFP 1-9 OPT to produce intact GFP. We engineered the construct (GFP S10)-L1-X-L2-(GFP S11) using methods well-known in the art, where L1 and L2 are linkers each consisting of amino acids GGGS (residues 1-4 of SEQ ID NO: 37) by inserting test proteins between GFP S10 and GFP S11 in the superfolder GFP S10-11 tag (FIG. 18 A). We successfully detected (GFP S10)-L1-sulfite reductase-L2-(GFP S11) using GFP 1-9 OPT, although the complementation was only ca. 1/30 as efficient as the C-terminal GFP S11 M3+GFP 1-10 OPT format. We also discovered that other partially soluble proteins became insoluble when expressed in this sandwich format. First we improved the complementation efficiency without regard to solubility. We started with a DNA construct coding for (GFP S10)-L1-NdeI: GGGSGSGG::BamHI-L2-(GFP S11), where the strands GFP S10 and GFP S11 are derived from superfolder GFP (FIG. 18 A), and the short amino acid sequence GGGSGSGG [SEQ ID NO: 37] provides a flexible linker between the two GFP strands. This was mutated by DNA shuffling and libraries of variants with improved complementation with GFP 1-10 OPT were screened in-vivo by sequential induction of the library from the pTET vector, followed by expression of the GFP 1-9 OPT from the pET vector within *E. coli* cells as colonies on plates (following methods outlined in EXAMPLE 4, supra). Six of the brightest clones were sequenced after three rounds of evolution (FIG. 18 A). We focused on the fifth mutant of the set of six, and this construct was termed (GFP S10 SM5)-L1-X-L2-(GFP S11 SM5) (SM5=sandwich mutant number 5). This optimum has the sequence YTMDLPDNHYLSTQTILLKDLNGTG-VGSGGGSHMGGGSGSGGGSGGGSTSEK RDHMVLLEYVTAAGITDAS*, [SEQ ID NO: 38], where the GFP S10 and GFP S11 strands are underlined, and the asterisk is the stop codon. The first italic sequence is derived from the NdeI cloning site CATATG, coding for amino acids HM. The second italic sequence is derived from the BamHI restriction site GGATCC, coding for the amino acids GS. Test proteins with in-frame NdeI and BamHI restriction sites are cloned into a vector containing the construct previously digested by NdeI and BamHI restriction enzymes using methods well-known in the art. Typically the in-frame region between the NdeI and BamHI site in a cloning cassette containing the construct would be replaced by a frame-shift stuffer with stop codons, to prevent false-positives caused by undigested vector or relegated vector (see EXAMPLE 1, supra, for representative frame-shift stuffer sequences). Such approaches are well-known in the art. The cassette is flanked by NcoI and XhoI restriction sites for cloning into the pTET vector. Although the complementation rate had increased ca. 20-fold with soluble sulfite reductase cloned into the Nde-1/BamH-1 site compared to the starting strand construct, the deleterious effect on protein solubility had also increased when tested with partially soluble HPS protein (as in EXAMPLE 4, supra). Next, to simultaneously select for improved complementation and decreased perturbation of fusion protein solubility, we used the same bait protein hexulose phosphate synthase, HPS, that we had used to improve the solubility and complementation of GFP S11 (EXAMPLE 4, supra). HPS was ca. 60% soluble expressed alone from the pTET vector (protein #9, FIG. 15), but insoluble expressed as (GFP S10 SM5)-L1-HPS-L2-(GFP S11 SM5) fusion protein. We focused on the upstream (GFP S10 SM5) domain, using shuffling and primer doping mutagenesis where a pool of fourteen synthetic oligonucleotide primers (FIG. 18 B). Each primer was centered at one of the fourteen amino acids of the GFP S10 SM5 domain, containing an NNN coding degeneracy the central target amino acid and flanking homology to the GFP S10 SM5 in the context of the cloning vector (target sequence shown in FIG. 18 B and FIG. 19). The pool of degenerate primers was added to the fragmented DNA during the reassembly reaction (reassembly performed as in EXAMPLE 4, supra). Such primer-doping mutagenesis techniques are well-known in the art. We shuffled and amplified the domain flanked by NcoI upstream and BamHI downstream, Nco1:(GFP S10 SM5)-L1-Nde-1::HPS::BamH1-L2-(GFP S11 SM5), adding the degenerate primer mix during reassembly of the fragments by polymerase chain reaction (PCR). We reamplified the domain from the reassembled mutated construct by PCR, then digested out the Nco1/Nde-1 fragment containing the mutated (GFP S10) pool, gel purified it using standard techniques, and cloned it into the receiving vector containing Nco1//Nde1::HPS::BamH1-L2-(GFP S11 SM5). After three rounds of selection using the sequential induction format from the pTET and pET plasmids (this example, supra, and following the methods outlined in EXAMPLE 4, supra for in vitro complementation assays using the immediate fragments in this example) the sequence of each of the best eight clones was determined by fluorescent dye terminator sequencing (FIG. 19). The best-performing clone, termed (GFP S10 A10)-L1-Nde1::HPS::BamH1-L2-(GFP S11 SM5) was ca. 45% soluble expressed in E. coli, a marked improvement relative to the starting construct which was insoluble, and complementation signal was now ca. ⅕ to ¼ that of the complementation using GFP 1-10 OPT to detect only the GFP S11 SM5 tag in the sandwich construct (supra). Next we tested the assay using the eighteen Pyrobaculum test proteins (see Table 3 supra, for identity and non-fusion solubility). Soluble and pellet fractions were assayed as previously described (EXAMPLE 9, supra) using the immediate fragments of the current example. We assayed these sandwich-format tagged proteins using GFP 1-10 OPT to specifically detect only the (GFP S11 SM5) tag as a reference, and also used GFP 1-9 OPT, which required the binding of both (GFP S10 A10) and (GFP S11 SM5) strands of the sandwich format tagged proteins. As expected, complementation was more efficient when only one strand was needed for detection (GFP 1-10 OPT case), and the detection of the pellet fraction using the urea-solubilized pellets was most efficient for the GFP 1-10 OPT detection case (FIG. 20). Nonetheless, soluble fraction fluorescence for the sandwich detected using GFP 1-9 OPT was well-correlated with the signal using the GFP 1-10 detection, reporting soluble protein as expected. Similarly, in vivo sequential induction was correlated with soluble pTET expression with GFP S11 M3 fusions (FIG. 20, see also EXAMPLE 9 supra and FIG. 15). The preferred optimum has the amino acid sequence YTMDLP DDHYLSTQTILSKDLNGTDVGSGGGSHMGGGSGSG-GGSGGGSTSEKRDHMVLLEYVTAAGITDAS*, [SEQ ID NO: 39], where the GFP S10 and GFP S11 strands are underlined, and the asterisk is the stop codon. The first italic sequence is derived from the NdeI cloning site CATATG, coding for amino acids HM. The second italic sequence is derived from the BamHI restriction site GGATCC, coding for the amino acids GS. Test proteins with in-frame NdeI and BamHI restriction sites are cloned into a vector containing the construct previously digested by NdeI and BamHI restriction enzymes using methods well-known in the art. The cassette is flanked by NcoI and XhoI restriction sites for cloning into the pTET vector. Typically the in-frame region between the NdeI and BamHI site in a cloning cassette containing the construct would be replaced by a frame-shift stuffer with stop codons, to prevent false-positives caused by undigested vector (see EXAMPLE 1, supra, for representative frame-shift stuffer sequences).

Example 13

Engineering Histidine-Enriched Mutants of GFP S11 Tags for Use in Detection and Purification We engineered GFP S11 to have a strong affinity for metal affinity protein purification beads in order to combine in one single tag the dual functions of protein detection and protein purification. We surmised that residues of GFP strand 11 that are exposed to solvent environment and whose side chain is not buried in the GFP structure (Ormö, Cubitt et al. 1996; Tsien 1998) could be changed to another amino-acid, without destroying the complementation of the GFP S11 tag with the large GFP 1-10 assay fragment. Four outside-pointing residues were mutated to histidine by PCR using specific primers: P1, GATATAACTAGTCATGACCACATGCAC-CTTCATGAG [SEQ ID NO: 40]; P2, CACATGCACCTTCATGAGCATGTACATGCTCAT [SEQ ID NO: 41]; and P3, GATATAGGTACCCCCATGAGCATG-TACATGCTCATGAAGGTGCA [SEQ ID NO: 42]. The resulting GFP 11 H7 fragment KHDHMHLHEH-VHAHGGT [SEQ ID NO: 18] was cloned as a C-terminal with the soluble control protein sulfite reductase. Examination of the GFP x-ray crystallographic structure (Ormo, Cubitt et al. 1996; Tsien 1998) (PDB ID REF: 1GFL) (Yang, Moss et al. 1996) showed that two additional residues at the end of GFP 11 H7 made no specific contacts with other amino-acids in the GFP 1-10 These additional residues were mutated to histidine in the GFP S11 H7 tag, to produce GFP S11 H9, HDHMHLHEHVHAHHHT [SEQ ID NO: 20]. The eighteen Pyrobaculum control proteins (see Table 3, supra) were fused to GFP S11 H7 or GFP S11 H9 and expressed from the pET vector (see EXAMPLE 9, supra) to test whether these tags could be used for a novel detection and purification system could to accurately quantify and purify fusion proteins in vitro. Overnight liquid cultures were diluted in fresh LB, grown to 0.5 OD 600 nm, and induced with 1 mM IPTG for 4 h at 37° C. The soluble and pellet fractions were fractionated by sonication and centrifugation. SDS-PAGE solubility of the eighteen Pyrobaculum control proteins with C-terminal GFP S11 H7 or GFP S11 H9 fusion tags was assessed as described earlier (EXAMPLE 9, supra) (See Table 4). Non-fusion solubility was previously determined for the proteins (EXAMPLE 9, supra). The GFP S11 H7 and GFP S11 H9 tags have minimal effect on protein solubility.

TABLE 4

Effect of GFP S11 H7 or H9 tags on solubility of eighteen proteins from *Pyrobaculum aerophilum*.

| # | [a]Protein | [b]MW | [c]Fraction soluble [d]NF | [e]WT | [f]H7 | [f]H9 |
|---|---|---|---|---|---|---|
| 1 | DNA-directed RNA polymerase | 12.5 | 0.05 | 0.00 | 0.00 | 0.07 |
| 2 | Sulfite reductase (dissimilatory subunit) | 12.7 | 1.00 | 1.00 | 0.95 | 0.94 |
| 3 | c-type cytochrome biogenesis factor | 14.4 | 0.77 | 0.28 | 0.75 | 0.57 |
| 4 | Translation initiation factor | 15.4 | 0.40 | 0.30 | 0.65 | 0.60 |
| 5 | Ribosomal protein S9p | 16.4 | 0.70 | 0.50 | 0.8 | 0.55 |
| 6 | Polysulfide reductase subunit | 21.0 | 0.00 | 0.00 | 0.00 | 0.00 |
| 7 | Nucleoside diphosphate kinase | 21.6 | 0.00 | 0.00 | 0.03 | 0.01 |
| 8 | Tartrate dehydratase β-subunit | 23.8 | 0.00 | 0.00 | 0.00 | 0.00 |
| 9 | 3-hexulose 6-phosphate synthase | 23.1 | 0.65 | 0.00 | 0.80 | 0.75 |
| 10 | Hydrogenase formation protein hypE | 26.8 | 0.35 | 0.05 | 0.40 | 0.30 |
| 11 | Methyltransferase | 29.3 | 0.00 | 0.00 | 0.05 | 0.00 |
| 12 | Chorismate mutase | 29.3 | 0.70 | 0.00 | 0.55 | 0.55 |
| 13 | Tyrosine t-RNA synthetase | 36.0 | 0.95 | 0.70 | 0.85 | 0.70 |
| 14 | nirD protein | 36.7 | 0.70 | 0.15 | 0.50 | 0.38 |
| 15 | Soluble hydrogenase | 37.3 | 0.00 | 0.00 | 0.00 | 0.00 |
| 16 | Aspartate-semialdehyde dehydrogenase | 37.4 | 0.00 | 0.00 | 0.00 | 0.00 |
| 17 | Phosphate cyclase | 37.4 | 0.80 | 0.30 | 0.90 | 0.80 |
| 18 | Purine-nucleoside phosphorylase | 41.7 | 0.05 | 0.00 | 0.02 | 0.01 |

[a]Eighteen proteins from the hyperthermophilic archaeon *Pyrobaculum aerophilum* (*Fitz-Gibbon*, *Choi* et al. 1997).
[b]Theoretical molecular weight in kD calculated from amino acid sequence.
[c]Fraction soluble as determined by SDS-PAGE densitometry (Experimental). Relative uncertainty is ca. 5%, average of three replicates.
[d]Non-fusion (NF) solubility and.
[e]C-terminal fusions with wild-type GFP S11 (WT) as determined in example 4.
[f]C-terminal fusions with GFP S11 histidine mutants (H7, H9).

Example 14

Sensitivity of the Complementation Reaction between S11 H7Fusion and GFP 1-10 A4

Purified sulfite reductase-GFP S11 H7 fusion dilutions were performed as described earlier (EXAMPLE 6, supra). The dilutions spanned the range 670 to 0.7 pmol per 100 μl aliquot, the aliquots were added to the wells of a 96-well plate, and then complementation was performed using a large excess (800 pmol) of GFP 1-10 A4 (ca. 0.5 mg/ml) added in a 100 μl aliquots. The GFP 1-10 A4 assay fragment was used due to the higher complementation rate relative to GFP 1-10 OPT for detection of GFP S11 H7. Fluorescence complementation kinetic traces (λexc=488 nm, λem=520 nm) were monitored overnight with a FL600 microplate fluorescence reader (Bio-Tek, Winooski, Vt.). The final fluorescence values were plotted versus the sulfite reductase-GFP S11 H7 fusion protein quantity (FIG. 21).

Example 15

Comparison of Purification of GFP Using Either an N-6HIS Tag or a C-Terminal GFP S11 H7 Tag Folding reporter GFP was cloned in an N-6HIS pET 28 vector (Novagen, Madison, Wis.), or into a pET vector with a C-terminal GFP S11 H7 TAG (no N-6HIS tag). 200 ml cultures of BL21(DE3) expressing each fusion were grown to OD600~0.5, and induced with 1 mM IPTG for 4 h at 37° C. The culture pellets were resuspended in 2 ml TNG and sonicated. The soluble fractions were loaded onto TALON® resin purification beads (TALON®, Clontech, Palo Alto, Calif.). After two washes with excess TNG buffer and one wash in TNG supplemented with 5 mM imidazole, the protein was eluted with 150 mM imidazole in TNG buffer. The crude extract and the purified fraction (150 mM Imidazole elution) were mixed with SDS-denaturing buffer and heated for 15 min at 100° C., and resolved on a 4-20% gradient Criterion SDS-PAGE (Biorad, Hercules, Calif.). The protein samples were stained using Gel Blue Code reagent (Pierce, Rockford, Ill.), and imaged using a GS-800 calibrated scanning densitometer (Biorad, Hercules, Calif.) (FIG. 22).

Example 16

Imidazole Elution Profile of Folding Reporter GFP Fused to S11 H7, S11 H9, or with an N-6HIS Tag, Bound to TALON® Resin To ascertain the relative affinity of the 6HIS, GFP S11 H7, and GFP S11 H9 tags for TALON® purification resin (TALON® Resin, Clontech, Palo Alto, Calif.), green fluorescent protein (GFP) was cloned in N-terminal fusion with GFP S11 H7 or S11 H9 non-6HIS-tagged pET vectors and in an N-6HIS pET vector. 3 ml cultures of each fusion in *E. coli* was grown to OD600~0.5, and induced with 1 mM IPTG for 4 h at 37° C. The culture pellets were resuspended in 150 μl TNG and sonicated. 50 μl of the soluble fractions were loaded onto 200 μl of TALON® resin beads (TALON®, Clontech, Palo Alto, Calif.) pre-incubated with TNG buffer. After three 1 ml washes in TNG, 20 μl of a 50% v:v slurry of beads was transferred to each of seven PCR tubes containing 50 μl TNG with 0, 5, 10, 25, 50, 75, and 100 mM imidazole, vortexed to mix, centrifuged to pellet the beads, and then 10 μl of the eluted fraction was diluted with 190 μl of TNG buffer in a 96 well microplate (Nunc-Immuno™ plate, Nunc, Rochester, N.Y.). The fluorescence (λex=488 nm, λem=530 nm) was measured using a FL600 microplate fluorescence reader (Bio-Tek, Winooski, Vt.) (FIG. 23). The results show that the GFP S11 H9 tag has a higher affinity for TALON® resin compared to the GFP S11 H7 tag, and should be suitable for protein purification using high stringency imidazole washes after protein binding.

Example 17

Metal Affinity Resin Purification of Several Test Proteins Fused to GFP S11 H9 Tag Seven partially soluble (*Pyrobaculum* test protein)-GFP S11 H9 fusions were selected for purification on TALON® resin beads using the affinity of the GFP S11 H9 mutant for the resin. 3 ml cultures of each fusion in *E. coli* BL21(DE3) were grown to OD600~0.5, and induced with 1 mM IPTG for 4 h at 37° C. The culture pellets were resuspended in 150 μl TNG and sonicated. 50 μl of the soluble fractions were mixed with 50 μl of TNG-washed TALON® resin beads (TALON®, Clontech, Palo Alto, Calif.) in a 300 μl eppendorf tube. After 10 min incubation at ambient temperature of ca. 25° C., the suspension was centrifuged and the supernatant was removed, and saved as the unbound fraction. The beads were washed with 1 ml TNG containing 5 mM imidazole, then 1 ml TNG containing 10 mM imidazole to remove adventitiously-bound proteins. Excess supernatant was removed by spinning the beads in a 0.2 u filter cartridge (Pierce, Rockford, Ill.). The bound proteins were eluted by incubating for 10 min with 75 μl of TNG containing 150 mM imidazole, and the suspension was centrifuged through 0.2μ filter cartridges and the filtrate supernatant was saved as the eluted fraction. TALON® resin with bound crude extract (S), the unbound fraction (U), and the eluted fraction (E) for each protein were denatured with 2×SDS buffer, and loaded on 4-20% Criterion SDS-PAGE (Biorad, Hercules, Calif.) (FIG. 24).

LITERATURE CITED

Adams, S. R., R. E. Campbell, et al. (2002). "New biarsenical ligands and tetracysteine motifs for protein labeling in vitro and in vivo: synthesis and biological applications." *J Am Chem Soc* 124(21): 6063-76.

Arai, M., K. Maki, et al. (2003). "Testing the relationship between foldability and the early folding events of dihydrofolate reductase from *Escherichia coli.*" *J Mol Biol* 328(1): 273-88.

Armstrong, N., A. de Lencastre, et al. (1999). "A new protein folding screen: application to the ligand binding domains of a glutamate and kainate receptor and to lysozyme and carbonic anhydrase." *Protein Sci* 8(7): 1475-83.

Baird, G. S., D. A. Zacharias, et al. (1999). "Circular permutation and receptor insertion within green fluorescent proteins." *Proc Natl Acad Sci USA* 96(20): 11241-6.

Baneyx, F. (1999). "Recombinant protein expression in *Escherichia coli.*" *Curr Opin Biotechnol* 10(5): 411-21.

Bertens, P., W. Heijne, et al. (2003). "Studies on the C-terminus of the Cowpea mosaic virus movement protein." *Arch Virol* 148(2): 265-79.

Crameri, A., E. A. Whitehorn, et al. (1996). "Improved green fluorescent protein by molecular evolution using DNA shuffling." *Nat Biotechnol* 14(3): 315-9.

Fahnert, B., H. Lilie, et al. (2004). "Inclusion bodies: formation and utilisation." *Adv Biochem Eng Biotechnol* 89: 93-142.

Fitz-Gibbon, S., A. J. Choi, et al. (1997). "A fosmid-based genomic map and identification of 474 genes of the hyperthermophilic archaeon *Pyrobaculum aerophilum.*" *Extremophiles* 1(1): 36-51.

Fox, J. D., R. B. Kapust, et al. (2001). "Single amino acid substitutions on the surface of *Escherichia coli* maltose-binding protein can have a profound impact on the solubility of fusion proteins." *Protein Sci* 10(3): 622-30.

Gegg, C. V., K. E. Bowers, et al. (1997). "Probing minimal independent folding units in dihydrofolate reductase by molecular dissection." *Protein Sci* 6(9): 1885-92.

Gerstein, M., A. Edwards, et al. (2003). "Structural genomics: current progress." *Science* 299(5613): 1663.

Goh, C. S., N. Lan, et al. (2004). "Mining the structural genomics pipeline: identification of protein properties that affect high-throughput experimental analysis." *J Mol Biol* 336(1): 115-30.

Iwakura, M. and T. Nakamura (1998). "Effects of the length of a glycine linker connecting the N- and C-termini of a circularly permuted dihydrofolate reductase." *Protein Eng* 11(8): 707-13.

Iwakura, M., T. Nakamura, et al. (2000). "Systematic circular permutation of an entire protein reveals essential folding elements." *Nat Struct Biol* 7(7): 580-5.

Jappelli, R., A. Luzzago, et al. (1992). "Loop mutations can cause a substantial conformational change in the carboxy terminus of the ferritin protein." *J Mol Biol* 227(2): 532-43.

Kelemen, B. R., T. A. Klink, et al. (1999). "Hypersensitive substrate for ribonucleases." *Nucleic Acids Res* 27(18): 3696-701.

Kim, J. S, and R. T. Raines (1993). "Ribonuclease S-peptide as a carrier in fusion proteins." *Protein Sci* 2(3): 348-56.

Knaust, R. K. and P. Nordlund (2001). "Screening for soluble expression of recombinant proteins in a 96-well format." *Anal Biochem* 297(1): 79-85.

Lopes Ferreira, N. and J. H. Alix (2002). "The DnaK chaperone is necessary for alpha-complementation of beta-galactosidase in *Escherichia coli.*" *J Bacteriol* 184(24): 7047-54.

Lutz, R. and H. Bujard (1997). "Independent and tight regulation of transcriptional units in *Escherichia coli* via the LacR/O, the TetR/O and AraC/I1-I2 regulatory elements." *Nucleic Acids Res* 25(6): 1203-10.

Makrides, S. C. (1996). "Strategies for achieving high-level expression of genes in *Escherichia coli.*" *Microbiol Rev* 60(3): 512-38.

Nixon, A. E. and S. J. Benkovic (2000). "Improvement in the efficiency of formyl transfer of a GAR transformylase hybrid enzyme." *Protein Eng* 13(5): 323-7.

Ormö, M., A. B. Cubitt, et al. (1996). "Crystal structure of the *Aequorea victoria* green fluorescent protein." Science 273 (5280): 1392-1395.

Patterson, G. H., S. M. Knobel, et al. (1997). "Use of the green fluorescent protein and its mutants in quantitative fluorescence microscopy." *Biophys J* 73(5): 2782-90.

Pelletier, J. N., K. M. Arndt, et al. (1999). "An in vivo library-versus-library selection of optimized protein-protein interactions." *Nat Biotechnol* 17(7): 683-90.

Pelletier, J. N., F. X. Campbell-Valois, et al. (1998). "Oligomerization domain-directed reassembly of active dihydrofolate reductase from rationally designed fragments." *Proc Natl Acad Sci USA* 95(21): 12141-6.

Richards, F. M. and P. J. Vithayathil (1959). "The preparation of subtilisn-modified ribonuclease and the separation of the peptide and protein components." *J Biol Chem* 234(6): 1459-65.

Rossi, F. M., B. T. Blakely, et al. (2000). "Monitoring protein-protein interactions in live mammalian cells by beta-galactosidase complementation." *Methods Enzymol* 328: 231-51.

Smith, V. F. and C. R. Matthews (2001). "Testing the role of chain connectivity on the stability and structure of dihydrofolate reductase from *E. coli*: fragment complementation and circular permutation reveal stable, alternatively folded forms." *Protein Sci* 10(1): 116-28.

Stemmer, W. P. (1994). "DNA shuffling by random fragmentation and reassembly: in vitro recombination for molecular evolution." Proc Natl Acad Sci USA 91(22): 10747-51.

Studier, F. W., A. H. Rosenberg, et al. (1990). "Use of T7 RNA polymerase to direct expression of cloned genes." *Methods Enzymol* 185: 60-89.

Tal, M., A. Silberstein, et al. (1985). "Why does Coomassie Brilliant Blue R interact differently with different proteins? A partial answer." *J Biol Chem* 260(18): 9976-80.

Terwilliger, T. C. (2004). "Structures and technology for biologists." *Nat Struct Mol Biol* 11(4): 296-7.

Tsien, R. Y. (1998). "The green fluorescent protein." *Annu Rev Biochem* 67: 509-44.

Ullmann, A., F. Jacob, et al. (1967). "Characterization by in vitro complementation of a peptide corresponding to an operator-proximal segment of the beta-galactosidase structural gene of *Escherichia coli.*" *J Mol Biol* 24(2): 339-43.

Waldo, G. S. (2003). "Genetic screens and directed evolution for protein solubility." *Curr Opin Chem Biol* 7(1): 33-8.

Waldo, G. S. (2003). "Improving protein folding efficiency by directed evolution using the GFP folding reporter." *Methods Mol Biol* 230: 343-59.

Waldo, G. S., B. M. Standish, et al. (1999). "Rapid protein-folding assay using green fluorescent protein." *Nature Biotechnology* 17(#7): 691-695.

Wehrman, T., B. Kleaveland, et al. (2002). "Protein-protein interactions monitored in mammalian cells via complementation of beta-lactamase enzyme fragments." *Proc Natl Acad Sci USA* 99(6): 3469-74.

Welply, J. K., A. V. Fowler, et al. (1981). "beta-Galactosidase alpha-complementation. Effect of single amino acid substitutions." *J Biol Chem* 256(13): 6811-6.

Wigley, W. C., R. D. Stidham, et al. (2001). "Protein solubility and folding monitored in vivo by structural complementation of a genetic marker protein." *Nat Biotechnol* 19(2): 131-6.

Worrall, D. M. and N. H. Goss (1989). "The formation of biologically active beta-galactosidase inclusion bodies in *Escherichia coli*." *Aust J Biotechnol* 3(1): 28-32.

Yang, F., L. G. Moss, et al. (1996). "The molecular structure of green fluorescent protein." *Nature Biotechnology* 14(10): 1246-1251.

Yokoyama, S. (2003). "Protein expression systems for structural genomics and proteomics." *Curr Opin Chem Biol* 7(1): 39-43.

We claim:

1. An isolated nucleic acid molecule comprising a polynucleotide sequence encoding beta strands 1-10 of a fluorescent protein comprising a polypeptide sequence at least 95% identical to:

the sequence set forth as SEQ ID NO: 4, wherein residue 39 is I, residue 105 is K, residue 111 is V, residue 128 is T, residue 166 is T, residue 167 is V and residue 205 is T; or the sequence set forth as SEQ ID NO: 6, wherein residue 80 is Q, residue 99 is Y, residue 105 is N, residue 111 is V, residue 128 is T, residue 166 is T, residue 172 is V and residue 205 is T; and wherein the beta strands 1-10 of the fluorescent protein are capable of self-complementation with a polypeptide corresponding to a beta strand 11 of the fluorescent protein.

2. The nucleic acid molecule of claim 1, wherein the beta strands 1-10 of the fluorescent protein comprise the amino acid sequence set forth as SEQ ID NO: 4.

3. The nucleic acid molecule of claim 1, wherein the beta strands 1-10 of the fluorescent protein consist of the amino acid sequence set forth as SEQ ID NO: 4.

4. The nucleic acid molecule of claim 1, wherein the beta strands 1-10 of the fluorescent protein comprise the amino acid sequence set forth as SEQ ID NO: 6.

5. The nucleic acid molecule of claim 1, wherein the beta strands 1-10 of the fluorescent protein consist of the amino acid sequence set forth as SEQ ID NO: 4.

6. The nucleic acid molecule of claim 1, wherein the polynucleotide sequence encoding beta strands 1-10 of the fluorescent protein comprises a nucleic acid sequence at least 95% identical to the nucleic acid sequence set forth as SEQ ID NO: 3.

7. The nucleic acid molecule of claim 6, wherein the polynucleotide sequence encoding beta strands 1-10 of the fluorescent protein comprises the nucleic acid sequence set forth as SEQ ID NO: 3.

8. The nucleic acid molecule of claim 6, wherein the polynucleotide sequence encoding beta strands 1-10 of the fluorescent protein consists of the nucleic acid sequence set forth as SEQ ID NO: 3.

9. The nucleic acid molecule of claim 1, wherein the polynucleotide sequence encoding beta strands 1-10 of the fluorescent protein comprises a nucleic acid sequence at least 95% identical to SEQ ID NO: 5.

10. The nucleic acid molecule of claim 9, wherein the polynucleotide sequence encoding beta strands 1-10 of the fluorescent protein comprises the nucleic acid sequence set forth as SEQ ID NO: 5.

11. The nucleic acid molecule of claim 6, wherein the polynucleotide sequence encoding beta strands 1-10 of the fluorescent protein consists of the nucleic acid sequence set forth as SEQ ID NO: 5.

12. The nucleic acid molecule of claim 1, wherein the fluorescent protein is a Green Fluorescent Protein (GFP).

13. The nucleic acid molecule of claim 1, operably linked to a promoter.

14. The nucleic acid molecule of claim 13, wherein the promoter is an inducible promoter.

15. An expression vector comprising the nucleic acid molecule of claim 1.

16. A host cell comprising the expression vector of claim 15.

17. The host cell of claim 16, wherein the host cell is an *Escherichia coli* cell.

18. The host cell of claim 16, wherein the host cell is a eukaryotic cell.

19. The host cell of claim 16, wherein the host cell is a mammalian cell.

* * * * *

UNITED STATES PATENT AND TRADEMARK OFFICE

CERTIFICATE OF CORRECTION

PATENT NO. : 8,685,667 B2
APPLICATION NO. : 13/118174
DATED : April 1, 2014
INVENTOR(S) : Geoffrey S. Waldo et al.

It is certified that error appears in the above-identified patent and that said Letters Patent is hereby corrected as shown below:

In the Claims:

Col. 95, line 54, Claim 5, line 3: "SEQ ID NO: 4" should read – SEQ ID NO: 6 –

Signed and Sealed this
Eighteenth Day of August, 2015

Michelle K. Lee
*Director of the United States Patent and Trademark Office*